US007935500B2

(12) United States Patent
Gerber et al.

(10) Patent No.: US 7,935,500 B2
(45) Date of Patent: May 3, 2011

(54) IDENTIFYING CALCINEURIN ACTIVATORS FOR TREATMENT OF SCHIZOPHRENIA

(75) Inventors: David J. Gerber, Somerville, MA (US); Maria Karayiorgou, Riverdale, NY (US); Tsuyoshi Miyakawa, Aichi (JP); Susumu Tonegawa, Chestnut Hill, MA (US)

(73) Assignees: Massachusetts Institute of Technology, Cambridge, MA (US); Rockefeller University, New York, NY (US)

( * ) Notice: Subject to any disclaimer, the term of this patent is extended or adjusted under 35 U.S.C. 154(b) by 1558 days.

(21) Appl. No.: 10/400,348

(22) Filed: Mar. 26, 2003

(65) Prior Publication Data

US 2004/0014095 A1 Jan. 22, 2004

Related U.S. Application Data

(60) Provisional application No. 60/367,944, filed on Mar. 26, 2002, provisional application No. 60/452,813, filed on Mar. 7, 2003.

(51) Int. Cl.
*C12Q 1/34* (2006.01)
*C12Q 1/68* (2006.01)
*C12Q 1/02* (2006.01)
*G01N 33/53* (2006.01)
*G01N 33/15* (2006.01)

(52) U.S. Cl. ............... 435/18; 435/6; 435/7.1; 435/29; 800/3

(58) Field of Classification Search .................... None
See application file for complete search history.

(56) References Cited

U.S. PATENT DOCUMENTS

| | | | |
|---|---|---|---|
| 4,522,811 A | 6/1985 | Eppstein et al. | |
| 4,683,202 A | 7/1987 | Mullis | |
| 5,143,854 A | 9/1992 | Pirrung et al. | |
| 5,288,644 A | 2/1994 | Beavis et al. | |
| 5,384,261 A | 1/1995 | Winkler et al. | |
| 5,424,186 A | 6/1995 | Fodor et al. | |
| 5,837,832 A | 11/1998 | Chee et al. | |
| 5,858,659 A | 1/1999 | Sapolsky et al. | |
| 6,013,621 A * | 1/2000 | Nishi et al. ................. | 514/2 |
| 6,316,003 B1 | 11/2001 | Frankel et al. | |
| 6,326,166 B1 | 12/2001 | Pomerantz et al. | |
| 6,448,443 B1 | 9/2002 | Schreiber et al. | |
| 2003/0171255 A1* | 9/2003 | Greengard et al. .......... | 514/1 |
| 2006/0172295 A1* | 8/2006 | Bilbe et al. .................. | 435/6 |
| 2006/0241042 A1* | 10/2006 | Kitamoto et al. ........... | 514/12 |

FOREIGN PATENT DOCUMENTS

| | | |
|---|---|---|
| WO | WO-9015070 | 12/1990 |
| WO | WO-9210092 | 6/1992 |
| WO | WO-9511995 | 5/1995 |
| WO | WO-9964379 | 12/1999 |
| WO | WO-0382210 | 10/2003 |

OTHER PUBLICATIONS

Leykin et al. Short and long-term immunosuppressive effects of clozapine and haloperidol. Immunopharmacology, vol. 37, pp. 75-86, 1997.*
Seeman. Comment on "Diverse Psychotomimetics Act Through a Common Signaling Pathway." Science vol. 305, No. 5681, p. 180, Jul. 2004.*
Sato et al. Impact of cyclosporine on emotional and social behavior in mice. Transplantation, vol. 83, No. 10, pp. 1365-1370, May 2007.*
Parsons et al. Altered skeletal muscle phenotypes in clcineurin Aalpha and Abeta gene-targeted mice. Molecular and Cellular Biology, vol. 23, No. 12, pp. 4331-4343, Jun. 2003.*
Cohen, PTW. Protein phosphatase 1-targeted in many directions. Journal of Cell Science, vol. 115, pp. 241-256, 2002.*
Abi-Dargham, et al., "Increased Baseline Occupancy of $D_2$ Receptors by Dopamine in Schizophrenia" *Proc. Natl. Acad. Sci. USA* 97: 8104-8109, 2000.
Ahn, et al., "The B"/PR72 subunit mediates CA2+-dependent dephosphorylation of DARPP-32 by protein phosphatase 2A" *PNAS*, 104(23):9876-9881, 2007.
Alberts, et al., "Expression of a Peptide Inhibitor of Protein Phosphate 1 Increase Phosphorylation and Activity of CREB in NIH 3T3 Fibroblasts." *Mol Cell Biol* 14(7): 4398-407, 1994.
Alderborn, et al., "Determination of Single-Nucleotide Polymorphisms by Real-time Pyrophosphate DNA Sequencing" *Genome Research*, 10(8): 1249-1258, 2000.
Allen, et al., "Ligand-Targeted Therapeutics in Anticancer Therapy" *Nature Reviews Cancer* 2: 750-765, 2002.
Altchul, SF, et al., "Methods Enzymol" 266:460-80, 1996.
Altschul, et al., "Basic Local Alignment Search Tool." *J. Mol. Biol.* 215(3): 403-410, 1990.
Altschul, et al., "Gapped BLAST and PSI-BLAST: a new generation of protein database search programs" *Nucleic Acids Res* 25: 3389-3402, 1997.
Amital, H. and Y. Shoenfeld, "Autoimmunity and schizophrenia: an epiphenomenon or an etiology?" *ISR J Med Sci*, 1993. 29(9): p. 593-7.
An, et al., "Efficient Lentiviral Vectors for Short Hairpin RNA Delivery Into Human Cells." *Hum. Gene Ther*. 14: 1207-1212, 2003.
Badner, et al., "Meta-Analysis of Whole-Genome Linkage Scans of Bipolar Disorder and Schizophrenia" *Mol Psychiatry* 7: 405-411, 2002.
Bailer, et al., "Genome Scan for Susceptibility Loci for Schizophrenia" *Neuropsychobiology* 42: 175-82, 2000.
Baker, et al., "Novel Mechanisms for Antisense-Mediated Regulation of Gene Expression" *Biochim. Biophys. Acta* 1489:3, 1999.

(Continued)

*Primary Examiner* — Jennifer Dunston
(74) *Attorney, Agent, or Firm* — Choate Hall & Stewart LLP; Fangli Chen

(57) ABSTRACT

The present invention provides targets, methods, and reagents for the diagnosis and treatment of schizophrenia and related conditions. The invention provides methods for the diagnosis of schizophrenia and susceptibility to schizophrenia by detection of polymorphisms, mutations, variations, alterations in expression, etc., in calcineurin genes or calcineurin interacting genes, or polymorphisms linked to such genes. The invention provides oligonucleotides, arrays, and antibodies for detection of polymorphisms and variants. The invention provides transgenic mice having alterations in such genes. The invention also provides methods of treating schizophrenia by administering compounds that target these genes. The invention further provides screening methods for identifying such compounds and compounds obtained by performing the screens.

5 Claims, 11 Drawing Sheets

OTHER PUBLICATIONS

Balschun, D., et al., "Deletion of the ryanodine receptor type 3 (RyR3) impairs forms of synaptic plasticity and spatial learning", *Embo J*, 18 (1999) 5264-73.

Banerji, et al., "A Lymphocyte-Specific Cellular Enhancer Is Located Downstream of the Joining Region in Immunoglobulin Heavy Chain Genes." *Cell* 33: 729, 1983.

Baughman, G., et al., "FKBP51, a novel T-cell-specific immunophilin capable of calcineurin inhibition". *Mol Cell Biol*, 1995. 15(8): p. 4395-402.

Baughman, G., et al., "Tissue distribution and abundance of human FKBP51, and FK506-binding protein that can mediate calcineurin inhibition". *Biochem Biophys Res Commun*, 1997. 232(2): p. 437-43.

Baumgrass, R., et al., Reversible inhibition of calcineurin by the polyphenolic aldehyde gossypol. J Biol Chem, 2001. 276(51): p. 47914-21.

Beaudry, et al., "Contrasting patterns and cellular specificity of transcriptional regulation of the nuclear receptor nerve growth factor-inducible B by haloperidol and clozapine in the rat forebrain" *Journal of Neurochemistry*, 75: 1694-1702, 2000.

Beckmann, et al., "EGR Transcription Factors in the Nervous System." *Neurochem Int*. 31(4): 477-510; discussion 517-6. Review 1993.

Bernstein et al., Nature 409:363, 2001.

Blouin, et al., "Schizophrenia Susceptibility Loci on Chromosomes 13q32 and 8p21" *Nat Genet* 20: 70-3, 1998.

Bockamp, et al., "Of Mice and Models: Improved Animal Models for Biomedical Research" *Physiol Genomics* 11(3): 115-32, 2002.

Boss, et al., "Induction of NFAT-Mediated Transcription by GQ-Coupled Receptors in Lymphoid and Non-Lymphoid Cells." *J Biol Chem*. 271(18): 10429-32, 1996.

Boute, et al., "The Use of Resonance Energy Transfer in High-Throughput Screen: BRET Versus FRET." *Trends Pharmacol Sci*. 23(8): 351-4. Review 2002.

Bram, R.J. and G.R. Crabtree, Calcium signalling in T cells stimulated by a cyclophilin B-binding protein. Nature, 1994. 371(6495): p. 355-8.

Breier, et al., "Schizophrenia Is Associated With Elevated Amphetamine-Induced Synaptic Dopamine Concentrations: Evidence from a Novel Positron Emission Tomography Method." *Proc. Natl. Acad. Sci. USA* 94: 2569-2574, 1997.

Brummelkamp, et al., "A System for Stable Expression of Short Interfering RNAs in Mammalian Cells" *Science* 296: 550-553, 2002.

Brzustowicz, Location of a Major Susceptibility Locus for Familial Schizophrenia on Chromosome 1q21-q22, *Science* 288: 678-82, 2000.

Byrne, et al., "Multiplex Gene Regulation: A Two-Tiered Approach to Transgene Regulation in Transgenic Mice" *Proc. Natl. Acad. Sci. USA* 86: 5473, 1989.

Calame, et al., "Transcriptional Controlling Elements in the Immunoglobulin and T Cell Receptor Loci" *Adv. Immunol*. 43: 235, 1988.

Cameron, A.M., et al., Calcineurin associated with the inositol 1,4,5-trisphosphate receptor-FKBP12 complex modulates Ca2+ flux. Cell, 1995. 83(3): p. 463-72.

Camp, et al., "Genomewide Multipoint Linkage Analysis of Seven Extended Palauan Pedigrees with Schizophrenia, by a Markov-Chain Monte Carlo Method" *Am J Hum Genet* 69: 1278-89, 2001.

Camper, et al., "Postnatal Repression of the α-Fetoprotein Gene is Enhancer Independent" *Genes Dev*. 3: 537, 1989.

Cardon, et al., "Association Study Designs for Complex Diseases" *Nature Reviews Genetics*, 2: 91-99, 2001.

Carlsson, et al., "Neurotransmitter Aberrations in Schizophrenia: New Perspectives and Therapeutic Implications" *Life Sci* 61: 75-94, 1997.

Chang, H., et al., *Nature* 376, 686-690, 1995.

Chen, et al., "Fluorescence Polarization in Homogenous Nucleic Acid Analysis" Genome Research 9(5): 492-498, 1999.

Chowdari, et al., "Immune related Genetic Polymorphism and Schizophrenia Among the Chinese" *Hum Immunol* 62: 714-24, 2001.

Chumakov, et al., "Genetic and Physiological Data Implicating the New Human Gene G72 and the Gene for D-Amino Acid Oxidase in Schizophrenia" *Proc Natl Acad Sci USA* 99(21): 13675-80, 2002.

Church, et al., "Genomic Sequencing" *Proc. Natl. Acad. Sci. USA* 81: 1991-1995, 1988.

Clayton, et al., "A Generalization of the Transmission/Disequilibrium Test for Uncertain Haplotype Transmission" *Am J Hum Genet* 65(4): 1170-7, 1999.

Coghlan, V.M., et al., Association of protein kinase A and protein phosphatase 2B with a common anchoring protein. Science, 1995. 267(5194): p. 108-11.

Coon, et al., "Evidence for a Chromosome 2p13-14 Schizophrenia Susceptibility Locus in Families from Palau, Micronesia" *Mol Psychiatry* 3: 521-7, 1998.

Corbett, et al., "Antipsychotic agents antagonize non-competitive N-methyl-D-aspartate antagonist-induced behaviours" *Psychopharmacology*, 120: 67-74, 1995.

Cotton, et al., "Reactivity of Cytosine and Thymine in Single-Base Pair Mismatches with Hydroxylamine and Osmium Tetroxide and its Application to the Study of Mutations." *Proc Natl Acad Sci. USA* 85: 4397-4401, 1985.

Cotton, et al., "Ribozyme Mediated Destruction of RNA I Vivo" *EMBO J*. 8:3861-3866, 1989.

Crabtree, G. R. & Olson, E. N., Cell 109 Suppl, S67-79, 2002.

Crabtree, G., *J. Biol. Chem*., 276(4): 2313-2316, 2001.

Craddock, et al., "Chromosome Workshop: Chromosomes 11, 14, and 15", *Am J Med Genet* 88: 244-54, 1999.

Craven, "Cyclosporine-associated organic mental disorders in liver transplant recipients" *Psychotomatics*, at http://psy.psychiatryonline.org.exp-prod1.hul.harvard.edu/cgi/content/abstract/32/1/94, printed Feb. 10, 2009.

Crawley, et al., "Explanatory Behavior Models of Anxiety in Mice" *Nerosci Biobehav Rev* 9(1985): 37-44, 1985.

Crowe, et al., "Report of the Chromosome 5 Workshop of the Sixth World Congress on Psychiatric Genetics" *Am J Med Genet* 88: 229-32, 1999.

*Current Protocols in Molecular Biology*, John Wiley & Sons, N.Y., 6.3.1-6.3.6., 1989.

Czernick, et al., "Production of Phosphorylation State-Specific Antibodies" *Methods Enzymol* 201: 264-83, 1991.

Database SNP (DBSNP) [Online], "SNP in the CNB gene included in the refSNP rs1868402", Database accession No. ss2743991, Jan. 2001 & Database NCBI (DBSNP) [Online], "Entry for reference (refSNP) cluster report", Database accession No. rs1868402, Feb. 2001.

Day, M., et al., J Neurophysiol 87, 2490-504, 2002.

Denhardt, et al., "Mechanism of Action of Antisense RNA" *Acad. Sci*. 660: 70, 1992.

Dorsett, et al., "siRNAs: Applications in Functional Genomics and Potential as Therapeutics" *Nature Reviews Drug Discovery*, 3: 318-329, 2004.

Eckert, et al. "DNA Polymerase Fidelity and the Polymerase Chain Reaction", *PCR Methods and Applications* 1: 17, 1991.

Ehrengruber, et al., "Modulation of Early Growth Response (EGR) Transcription Factor-Dependent Gene Expression by Using Recombinant Adenovirus" *Gene* 258: 63-69, 2000.

Fanger, C., et al., *J. Cell. Biol*., 131, 655-667, 1995.

Faraone, et al., "Genome Scan of European-American Schizophrenia Pedigrees: Results of the NIMH Genetics Initiative and Millennium Consortium" *Am J Med Genet* 81: 290-5, 1998.

Flanagan, W.M., Nature, 352: 803-7, 1991.

Flavell, et al., "Analysis of the β-δ-Globin Gene Loci in Normal and Hb Lepore DNA: Direct Determination of Gene Linkage and Intergene Distance" *Cell* 15: 25, 1978.

Floyd, et al., "Combinatorial Chemistry as a Tool for Drug Discovery" *Prog Med Chem* 36: 91-168, 1999.

Fodor, et al., "Light-Directed, Spatially Addressable Parallel Chemical Synthesis" *Science* 251: 767-777, 1991.

Franch, et al., "U-Turns and Regulatory RNAs" *Curr. Opin. Microbiol* 3: 159, 2000.

Freedman, et al., "Evidence for the Multigenic Inheritance of Schizophrenia" *Am J Med Genet* 105: 794-800, 2001.

Frey, N., J.A. Richardson, and E.N. Olson, "Calsarcins, a novel family of sarcomeric calcineurin-binding proteins". Proc Natl Acad Sci U S A, 2000. 97(26): p. 14632-7.

Futatsugi, A., et al., :Facilitation of NMDAR-independent LTP and spatial learning in mutant mice lacking ryanodine receptor type 3 , *Neuron*, 24 (1999) 701-13.

Gainetdinov, et al., "Genetic Animal Models: Focus on Schizophrenia" *Trends in Neurosciences* 24(9), 2001.

Ganguli, R., et al., "Autoimmunity in schizophrenia: a review of recent findings". Ann Med, 1993. 25(5): p. 489-96.

Ganguli, R., J.S. Brar, and B.S. Rabin, "Immune abnormalities in schizophrenia: evidence for the autoimmune hypothesis". Harv Rev Psychiatry, 1994. 2(2): p. 70-83.

Geever, et al., "Direct Identification of Sickle Cell Anemia by Blot Hybridization" *Proc Natl. Acad. Sci. USA* 78: 5081, 1981.

Genazzani, A.A.,, et al., "Calcineurin controls inositol 1,4,5-trisphosphate type 1 receptor expression in neurons". Proc Natl Acad Sci U S A, 1999. 96(10): p. 5797-801.

Gerber, et al., "Evidence for Association of Schizophrenia with Genetic Variation in the 8p21.3 Gene, PPP3CC, Encoding the Calcineurin Gamma Subunit" *Proc Natl Acad Sci. USA* 100(15): 8993-8998, 2003.

Goodman, A.B., "Elevated risks for amyotrophic lateral sclerosis and blood disorders in Ashkenazi schizophrenic pedigrees suggest new candidate genes in schizophrenia", *Am J Med Genet*, 54 (1994) 271-8.

Graef, I.A., et al., "NFAT signaling in vertebrate development". Curr Opin Genet Dev, 2001. 11(5): p. 505-12.

Greengard, et al., "Phosphorylation of DARPP-32 by CdkS modulates dopamine signalling in neurons" *Nature*, 402, 1999.

Greengard, P., Science 294, 1024-30, 2001.

Griffith, JP, et al., "X-ray structure of calcineurin inhibited by the immunophilin-immunosuppressant FKBP12-FK506 complex", Cell Aug. 11, 1995;82(3):507-22.

Grishok, et al., "Genes and Mechanisms Related to RNA Interference Regulate Expression of the Small Temporal RNAs that Control *C. elegans* Developmental Timing" *Cell* 106: 23-24, 2001.

Guatelli, et al., "Isotheral, in vitro Amplification of Nucleic Acids by a Multienzyme Reaction Modeled After Retroviral Replication" *Proc. Natl. Acad. Sci. USA* 87: 1874, 1990.

Guerini, et al., "Isolation and Sequence of a CDNA Clone for Human Calcineurin B, the CA2+-Binding Subunit of the CA2+/Calmodulin-Stimulated Protein Phosphatase" *DNA*, 8:(9):675-682, 1989, Abstract Only.

Gurling, et al., "Genomewide Genetic Linkage Analysis Confirms the Presence of Susceptibility Loci for Schizophrenia, on Chromosomes 1q32.2, 5q33.2, and 8p21-22 and Provides Support for Linkage to Schizophrenia, on Chromosomes 11q23.3-24 and 20q12.1-11.23" *Am J Hum Genet* 68: 661-73, 2001.

Hakak, et al., "Genome-wide expression analysis reveals dysregulation of myelination-related genes in chronic schzoprenia" *Proceedings of the National Academy of Sciences of USA*, 98(8): 4746-4751, 2001.

Hanes, et al., "In Vitro Selection and Evolution of Functional Proteins by Using Ribosome Display" *Proc Natl. Acad. Sci. USA* 94: 4937-4942, 1997.

Hashimoto, H., et al., "Altered psychomotor behaviors in mice lacking pituitary adenylate cyclase-activating polypeptide (PACAP)". Proc Natl Acad Sci U S A, 2001. 98(23): p. 13355-60.

Hasuwa, et al., "Small Interfering RNA and Gene Silencing in Transgenic Mice and Rats" *FEBS Lett* 532(1-2): 227 30, 2002.

Haucke, V., *Nat Neurosci* 3, 1230-2, 2000.

Hippenmeyer, et al., "A Role for Neuregulin1 Signaling in Muscle Spindle Differentiation" *Neuron* 36: 1035-49, 2002.

Hodgkiss, J.P. and J.S. Kelly, "Only 'de novo' long-term depression (LTD) in the rat hippocampus in vitro is blocked by the same low concentration of FK506 that blocks LTD in the visual cortex". Brain Res, 1995. 705(1-2): p. 241-46.

Hommel, et al., "Local Gene Knockdown in the Brain Using Viral-Mediated RNA Interference" *Nature Medicine*, 9(12): 1539-1544, 2003.

Horsley, V. and G.K. Pavlath, "Nfat: ubiquitous regulator of cell differentiation and adaptation". J Cell Biol, 2002. 156(5): p. 771-4.

Hovatta, et al., "Linkage Analysis of Putative Schizophrenia Gene Candidate Regions on Chromosomes 3p, 5q, 6p, 8p, 20p, and 22q in a Population-Based Sampled Finnish Family Set." *Mol Psychiatry* 3(5): 452-7, 1998.

Hutvagner, et al., "A Cellular Function for the RNA-Interference Enzyme Dicer in the Maturation of the Let-7 Small Temporal RNA" *Science*, 293: 834-838, 2001.

Ikegami, S., et al., "A facilitatory effect on the induction of long-term potentiation in vivo by chronic administration of antisense oligodeoxynucleotides against catalytic subunits of calcineurin". Brain Res Mol Brain Res, 1996. 41(1-2): p. 183-91.

International Preliminary Examination Report for PCT/US03/09578 (Aug. 17, 2007).

International Search Report for PCT/US03/09578 (Oct. 26, 2006).

International Search Report for PCT/US04/21030 (Nov. 1, 2005).

Isaac, J., Protein Phosphatase 1 and LTD. "Synapses Are the Architects of Depression. Neuron", 2001. 32(6): p. 963-6.

Javitt, et al., "Recent Advances in the Phencyclidine Model of Schizophrenia" *Am J Psychiatry* 148(10): 1301-8, 1991.

Jorde, et al., "Linkage Disequilibrium and the Search for Complex Disease Genes" *Genome Research* 10: 1435-1444, 2000.

Kao, P.N., et al., "Cloning and expression of cyclosporin A- and FK506-sensitive nuclear factor of activated T-cells: NF45 and NF90". J Biol Chem, 1994. 269(32): p. 20691-9.

Karayiorgou, et al., "A Turning Point in Schizophrenia Genetics." *Neuron* 19: 967-79, 1997.

Karayiorgou, M., Morris, et al., "Schizophrenia susceptibility associated with interstitial deletions of chromosome 22q11", *Proc Natl Acad Sci U S A*, 92 (1995) 7612-6.

Kashishian, A., et al., "AKAP79 inhibits calcineurin through a site distinct from the immunophilin-binding region". J Biol Chem, 1998. 273(42): p. 27412-9.

Kato, K., "The role of calcineurin on the induction of synaptic plasticity". Nihon Shinkei Seishin Yakurigaku Zasshi, 2000. 20(5): p. 189-98, Abstract Only.

Kendler, et al., "Evidence for a Schizophrenia Vulnerability Locus on Chromosome 8p in the Irish Study of High-Density Schizophrenia Families" *Am J Psychiatry* 153: 1534-40, 1996.

Kennedy, et al., "Chromosome 4 Workshop Summary: Sixth World Congress on Psychiatric Genetics", Bonn, Germany, Oct. 6-10, 1998 *Am J Genet* 88: 224-8, 1999.

Kessel, et al., "Murine Developmental Control Genes" *Science* 249: 374, 1990.

Ketting, et al., "Dicer Functions in RNA Interference and in Synthesis of Small RNA Involved in Development Timing in *C. elegans*" *Genes Dev.* 15: 2654-2659, 2001.

Kincaid, et al., "Cloning and Characterization of Molecular Isoforms of the Catalytic Subumit of Calcineurin Using Nonisotopic Methods" *The Jornal of Biological Chemistry*, 265(19): 11312-11319, 1990.

Kinoshita, et al., "No Association with the Clacineurin A. Gammna Subunit Gene (PPP3CC) Heplotype to Japanese Schizophrenia" *The Jorurnal of Neural Transmission*, 112: 1255-1262, 2005.

Kirch, D.G., "Infection and autoimmunity as etiologic factors in schizophrenia: a review and reappraisal". Schizophr Bull, 1993. 19(2): p. 355-70.

Kirov, et al., "Finding Schizophrenia Genes" *The Journal of Clinical Invenstigation*, 115(6): 1440-1448, 2005.

Kissinger, CR, et al., "Crystal structures of human calcineurin and the human FKBP12-FK506-calcineurin complex", Nature, 1995. 378(6557):641-4.

Klauck, T.M., et al., "Coordination of three signaling enzymes by AKAP79, a mammalian scaffold protein". Science, 1996. 271(5255): p. 1589-92.

Klee, et al., "Regulation of the Calmodulin-Stimulated Protein Phosphatase, Calcineurin" *J Biol Chem* 273: 13367-70, 1998.

Klinger, M., et al., "Suramin and the suramin analogue NF307 discriminate among calmodulin-binding sites". Biochem J, 2001. 355(Pt 3): p. 827-33.

Kolanus, W., *Curr Top Microbiol Immunol*; 243:37-54, 1999.

Kouzu, Y., et al., "Mutant mice lacking ryanodine receptor type 3 exhibit deficits of contextual fear conditioning and activation of calcium/calmodulin-dependent protein kinase II in the hippocampus", *Brain Res Mol Brain Res*, 76 (2000) 142-50.

Kruglyak, et al., "High-Resolution Genetic Mapping of Complex Traits" *Am. J. Hum. Genet.* 56: 1212-1223, 1995.

Kwan, et al., "Conditionla Alleles in mice: Practical Considerations for Tissue-Specific Knockouts." *Genesis*, 32(2): 49-62, 2002.

Kwoh, et al., "Transcription-Based Amplification System and Detection of Amplified Human Immunodeficiency Virus Type 1 with a Bead-Based Sandwich Hybridization Format" *Proc. Natl. Acad. Sci. USA* 86: 1173, 1989.

Lagos-Quintana, et al., "Identification of Novel Genes Coding for Small Expressed RNAs" *Science* 294: 853-858, 2001.

Lai, et al., "Cain, a Novel Physiologic Protein Inhibitor of Calcineurin." *J Biol* 273(29): 18325-31, 1998.

Lai, M.M., et al., *J Biol Chem* 274, 25963-6, 1999.

Landergren, et al., "A Ligase-Mediated Gene Detection Technique" *Science* 241: 1077, 1988.

Laruelle, et al., "Single Photon Emission Computerized Tomography Imaging of Amphetamine Induced Dopamine Release in Drug-Free Schizophrenia Subjects" *Proc. Natl. Acad. Sci. USA* 93: 9235-9240, 1996.

Lee, H.W., et al., "Pituitary adenylate cyclase-activating polypeptide regulation of vasoactive intestinal polypeptide transcription requires Ca2+ influx and activation of the serine/threonine phosphatase calcineurin". J Neurochem, 1999. 73(4): p. 1769-72.

Lefebvre, et al., "Protein Phosphates 1 and 2A Regulate the Transcriptional and DNA Binding Activities of Retinoic Acid Receptors." *J Biol Chem* 270(18): 10806-16, 1995.

Levinson, et al., "Genome Scan of Schizophrenia" *Am J Psychiatry* 155: 741-50, 1998.

Lewandowski, et al., "Conditional Control of Gene Expression in the Mouse" 2(10): 743-55, 2001.

Lewis, et al., "Catching Up on Schizophrenia: Natural History and Neurobiology" *Neuron* 28: 325, 2000.

Lewis, et al., "Genome Scan Meta-Analysis of Schizophrenia and Bipolar Disorder, Part II: Schizophrenia" *Am J Hum Genet.* 73(1): 34-48, 2003.

Lewontin, et al., "On Measures of Gametic Disequilibrium." *Genetics* 120: 849-852, 1988.

Li, H. and Stark, G., $NF_\kappa B$-dependent signaling pathways, *Exp. Hematol.*, 30 (2002) 285-296.

Li, T.K., et al., "Calcium- and FK506-independent interaction between the immunophilin FKBP51 and calcineurin". J Cell Biochem, 2002. 84(3): p. 460-71.

Lin, et al., "Highly polymorphic sequence variation in calcinerin B coding region (PP3R1)" *Human Molecular Genetics*, 3:(3):520, 1994.

Lin, et al., "Inhibition of Calcineurin Phosphate Activity by a Calcineurin B Homologous Protein" J Biol Chem 274(51): 36125-31, 1999.

Liu, et al., "Genetic Variation and Susceptibility to Schizophrenia" *Proc Natl Acad Sci USA* 99(26): 16859-64, 2002.

Liu, et al., "Genetic Variation at the 22q11 PRODH2/DGCR6 Locus Presents an Unusual Pattern and Increases Susceptibility to Schizophrenia" *Proc Natl Acad Sci USA.* 99(6): 3717-22, 2002.

Liu, J., et al., *Cell*, 66: 807-15, 1991.

Madden, et al., "Positive and Negative Regulation of Transcription and Cell Growth Mediated by the EGR Family of Zinc-Finger Gene Products." *Ann NY Acad Sci* 684: 75-84, 1993.

Manfroid, I., J.A. Martial, and M. Muller, "Inhibition of protein phosphatase PP1 in GH3B6, but not in GH3 cells, activates the MEK/ERK/c-fos pathway and the human prolactin promoter, involving the coactivator CPB/p300". Mol Endocrinol, 2001. 15(4): p. 625-37.

Manji, et al., "Signal Transduction and Genes-to-Behaviours Pathways in Psychiatric Diseases" *Science's STKE*, 207(49): 1-7, 2003.

Marcoulatos, P., et al., "Mapping interleukin enhancer binding factor 2 gene (ILF2) to human chromosome 1 (1q11-qter and 1p11-p12) by polymerase chain reaction amplification of human-rodent somatic cell hybrid DNA templates". *J Interferon Cytokine Res*, 1996. 16(12): p. 1035-8.

Mattila, et al., "Fidelity of DNA Sythesis by the *Thermococcus litoralis* DNA Polymerase—an Extremely Heat Stable Enzyme with Proofreading Activity" *Nucleic Acid Res* 19: 4967, 1991.

McCarthy, et al. "The Use of Single-Nucleotide Polymorphism Maps in Pharmacogenomics" *Nature Biotechnology*, Nature Pub. Co, 18:505-508, 2000.

McInnes, L.A., et al., "Fine-scale mapping of a locus for severe bipolar mood disorder on chromosome 18p11.3 in the Costa Rican population", *Proc Natl Acad Sci USA*, 98 (2001) 11485-90.

McKerchar, et al., "Chronic PCP-induced 1-79 changes in zif268 mRNA expression; modulation by clozapine and haloperidol" *Society for Neuroscience Abstracts*, 27(2):1760, 2001.

McManus, M.T., et al., RNA, 8:842-850, 2002.

Misra, U.K., et al., "Chloroquine, quinine and quinidine inhibit calcium release from macrophage intracellular stores by blocking inositol 1,4,5- trisphosphate binding to its receptor". J Cell Biochem, 1997. 64(2): p. 225-32.

Misra, U.K., et al., "Cyclosporin A inhibits inositol 1,4,5-trisphosphate binding to its receptors and release of calcium from intracellular stores in peritoneal macrophages". J Immunol, 1998. 161(11): p. 6122-7.

Mittlestadt, et al., "Cyclosporin A-Sensitive Transcription Factor Egr-3 Regulates Fas Ligand Expression" *Mol Cell Biol* 18:3744-51, 1998.

Miyagashi, et al., "U6 Promoter-Driven siRNAs with Four Uridine 3' Overhangs Efficiently Suppress Targeted Gene Expression in Mammalian Cells" *Nat. Biotech* 20: 497-500, 2002.

Miyakawa, et al., "Conditional Calcineurin Knockout Mice Exhibit Multiple Abnormal Behaviors Related to Schizophrenia." *Proc Natl Acad Sci USA* , 100(15): 8987-8992, 2003.

Mohn, et al., "Mice with Reduced NMDA Receptor Expression Display Behaviors Related to Schizophrenia." *Cell* 98(4): 427-36, 1999.

Mondragon, A., et al., *Biochemistry* Apr. 22, 1997;36(16):4934-42.

Mulkey, R.M., et al., "Involvement of a calcineurin/inhibitor-1 phosphatase cascade in hippocampal long-term depression". Nature, 1994. 369(6480): p. 486-8.

Myers, et al., "Detection of Single Base Substitutions by Ribonuclease Cleavage at Mismatches in RNA:DNA Duplexes." *Science* 230: 1242, 1985.

Nakki, et al.. "Effects of phenyclidine on immediate early gene expression in the brain" *Journal of Neuroscience Research*, 45(1):13-27, 1996.

Nellen, *Trends Biochem. Sci.*, 18:419, 1993.

Nicolson, et al., "Premorbid Speech and Language Impairments in Childhood-Onset Schizophrenia: Association With Risk Factors" *Am. J. Psychiatry* 157: 794-800, 2000.

Nielsen, et al., "Applications of Peptide Nucleic Acids" *Curr. Opin. Biotech.* 10: 71, 1999.

Nielsen, et al., "Sequence-Selective Recognition of DNA by Strand Displacement with a Thymine-Substituted Polyamide" *Science* 245: 1597-1500, 1991.

Nielsen, P. E. et al., Bioconjugate Chemistry, 1994, 5, American Chemical Society, p. 1 (1994).

Nishi, et al., "Regulation of DARPP-32 dephosphorylation at PKA- and CdkS-sites by NMDA and AMPA receptors: distinct roles of calcineuring and protein phosphatase-2A" *Journal of Neurochemistry*, 81:832-841, 2002.

Nowotny, et al., "SNP Analysis to Dissect Human Traits" *Curr. Op. Neurobiol.* 11: 637-641, 2001.

Noy, S., et al., "Schizophrenia and autoimmunity—a possible etiological mechanism?" Neuropsychobiology, 1994. 30(4): p. 157-9.

Nurnberger, et al., "Diagnostic Interview for Genetic Studies". *Arch. Gen. Psychiatry* 51: 849-859, 1994.

O'Donovan, et al., "The EGR Family of Transcription-Regulatory Factors: Progress at the Interface of Molecular and Systems Neuroscience." *Trends Neurosci.* 22(4): 167-73, Review1999.

Orita, et al., "Detection of Polymorphism of Human DNA by Gel Electrophoresis as Single-Strand Conformation Polymorphisms" *Proc. Natl. Acad. Sci. USA* 86: 2766-2270, 1989.

Otto, C., et al., "Altered emotional behavior in PACAP-type-I-receptor-deficient mice". Brain Res Mol Brain Res, 2001. 92(1-2): p. 78-84.

Paddison, et al., "Short hairpin RNAs (shRNAs) Induce Sequence-Specific Silencing in Mammalian Cells" *Genes and Dev* 16: 948-958, 2002.

Pasquinelli, et al., "MicroRNAs: Deviants no Longer" *Trends in Genetics* 18(4): 171-173, 2002.
Paul, et al., "Effective Expression of Small Interfering RNA in Human Cells." *Nat. Biotech.* 20: 505-508, 2002.
Paunio, et al., "Genome-Wide Scan in a Nationwide Study Sample of Schizophrenia Families in Finland Reveals Susceptibility Loci on Chromosomes 2q and 5q" *Hum Mol Genet* 10: 3037-48, 2001.
Plyte, S., et al., "Identification and characterization of a novel nuclear factor of activated T-cells-1 isoform expressed in mouse brain". J Biol Chem, 2001. 276(17): p. 14350-8.
Pritchard, et al., "Linkage Disequilibrium in Humans: Models and Data" *Am. J. Hum. Genet.* 69: 1-14, 2001.
Pulver, et al., "Schizophrenia: A Genome Scan Targets Chromosomes 3p and 8p as Potential Sites of Susceptibility Genes" *Am J Med Genet* 60: 252-60, 1995.
Queen, et al. "Immunoglobulin Gene Transcription Is Activated by Downstream Sequence Elements" Cell 33:741, 1983.
Robertson, et al., "Induction patterns of Fos-like immunoreactivity in the forebrain as predictors of atypical antipsychotic activity" *The Journal of Pharmacology and Experimental Therapeutics*, 271(2): 1058-1066, 1994.
Rothermundt, et al., "Review of Immunological and Immunopathological Findings in Schizophrenia." *Brain Behav Immun* 15(4):319-39, 2001.
Rubinson, et al., "A Lentivirus-Based System to Functionally Silence genes in Primary Mammalian Cells, Stem Cells and Transgenic Mice by RNA Interference" *Nature Genet*. 33: 401-406, 2003.
Rubinstein, G., "Schizophrenia, rheumatoid arthritis and natural resistance genes". Schizophr Res, 1997. 25(3): p. 177-81.
Rusnak, et al., "Calcineurin: Form and Function" *Physiological Reviews* 80(4): 1483-1522, 2000.
Saiki, et al., "Analysis of Enzymatically Amplified β-Globin and HLA-DQα DNA with Allele-Specific Oligonucleotide Probes" *Nature* 324: 163-166, 1986.
Sakic, B., H. Szechtman, and J.A. Denburg, *Neurobehavioral alterations in autoimmune mice.* Neurosci Biobehav Rev, 1997. 21(3): p. 327-40.
Sambasivarao, D., et al., A novel immunosuppressive factor in bovine colostrum blocks activation of the interleukin 2 gene enhancer at the NFAT site. Biochem Cell Biol, 1996. 74(4): p. 585-93.
Sanger, et al., "DNA Sequencing with Chain-Terminating Inhibitors" *Proc. Natl. Acad. Sci.* 74: 5463-5467, 1977.
Schwab, et al., "Evidence Suggestive of a Locus on Chromosome 5q31 Contributing to Susceptibility for Schizophrenia in German and Israeli Families by Multipoint Affected Sib-Pair Linkage Analysis" *Mol Psychiatry* 2: 156-60, 1997.
Schwartz, M. and H. Silver, "Lymphocytes, autoantibodies and psychosis—coincidence versus etiological factor: an update". Isr J Psychiatry Relat Sci, 2000. 37(1): p. 32-6.
Seeman, et al., "Dopamine receptors and the Dopamine Hypothesis of Schizophrenia" *Synapse* 1: 133-52, 1987.
Serafini, T., et al., *Immunity*, 3, 239-250, 1995; Fanger, C., et al., *J. Cell. Biol.*, 131, 655-667, 1995.
Serebriiskii, I.G. et al.,*Methods Mol Biol*;175:415-54, 2001.
Sevetson, et al., "A Novel Activation Function for NAB Proteins in EGR-Dependent Transcription of the Luteinizing Hormone b Gene" *J Biol. Chem* 275(13): 9749-9757, 2000.
Shaw, J.P., et al., *Science*, 241: 202-205, 1988.
Sheffield, et al., "Attachment of a 40-Base-Pair G+C-Rich Sequence (GC-clamp) to Genomic DNA Fragments by the Polymerase Chain Reaction Results in Improved Detection of Single-Base Changes" *Proc. Natl. Acad. Sci. USA* 86: 232-236, 1989.
Shibasaki, et al., "Calcineurin as a Multifunctional Regulator" *J Biochem* 131: 1-15, 2002.
Snyder, G.L., et al., "Phosphorylation of DARPP-32 and protein phosphatase inhibitor-1 in rat choroid plexus: regulation by factors other than dopamine". J Neurosci, 1992. 12(8): p. 3071-83.
Snyder, et al., "Immunophilins in the nervous system", *Neuron*, 21 (1998) 283-94.
Snyder, S.H., et al., "Neural actions of immunophilin ligands", *Trends Pharmacol Sci*, 19 (1998) 21-6.

Sobin, et al., "Early, Non-Psychotic Deviant Behavior in Schizophrenia: a Possible Endophenotypic Marker for Genetic Studies" *Psychiatry Res.* 101: 101-113, 2001.
Stefansson, et al., "Neuregulin 1 and Susceptibility to Schizophrenia" *Am J Hum Genet* 71: 877-92, 2002.
Stober, et al., "Splitting Schizophrenia: Periodic Catatonia-Susceptibility Locus on Chromosome 15q15" *Am J Hum Genet* 67: 1201-7, 2000.
Straub, et al., "Genetic Variation in the 6p22.3 Gene DTNBP1, the Human Ortholog of the Mouse Dysbindin Gene, Is Associated with Schizophrenia" *Am. J. Hum. Genet*. 71: 337-348, 2002.
Straub, et al., "Genome-Wide Scans of Three Independent Sets of 90 Irish Multiplex Schizophrenia Families and Follow-up of Selected Regions in All Families Provides Evidence for Multiple Susceptible Genes." *Mol Psychiatry* 7: 542-59, 2002.
Straub, et al., "Support for a Possible Schizophrenia Vulnerablility Locus in Region 5q22-31 in Irish Families." *Mol Psychiatry* 2(2):148-55, 1997.
Suarez, et al., "Genomewide Linkage Scan of 409 European-Ancestry and African American Families with Schizophrenia: Suggestive Evidence of Linkage at 8p23.2-p21-1 and 11p13.1-q14.1 in the Combined Sample " *The American Journal of Human Genetics*, 78: 315-333, 2006.
Sui, et al., "A DNA Vector-Based RNAi Technology to Suppress Gene Expression in Mammalian Cells" *Proc Natl Acad Sci.* 99(8): 5515-5520, 2002.
Sun , et al., "Cabin 1, a Negative Regulator for Calcineurin Signaling in T Lymphocytes." *Immunity* 8(6): 703-11, 1998.
Supplementary European Search Report for EP 03728301 (Feb. 2008).
Supplementary European Search Report for EP 04777309 (Oct. 2007).
Svaren, et al., NAB2, "A Corepressor of NGF1OA (Egr-1) and Krox20, Is Induced by Proliferative and Differentiative Stimuli" *Mol. Cell. Biol*, 16(7): 3545-3553, 1996.
Svenningsson, et al., "Diverse Psychotomimetics Act Through a Common Signaling Pathway" *Science*, 302: 1412-1415, 2003.
Swirnoff, et al., "A Corepressor of NGRI-A (Egr-1) Contains an Active Transcriptional Repression Domain" *Mol Cell Biol.* 18(1): 512-524, 1998.
Takeshima, H., et al., "Generation and characterization of mutant mice lacking ryanodine receptor type 3", J Biol Chem, 271 (1996) 19649-52.
Tan, et al., "Stereoselective Sythesis of Over Two Million Compounds Having Structural Features Both Reminiscent of Natural Products and Compatible with Miniaturized Cell-Based Assays." *Am. Chem Soc.* 120: 8565-8566, 1998.
Terryn, et al., "The Sense of Naturally Transcribed Antisense RNAs in Plants" *Trends Plant Sci* 5: 1360, 2000.
Thaker, et al., "Advances in Schizophrenia" *Nat Med* 7: 667-71, 2001.
Timmerman, L., et al., *Nature*, 383, 837-40, 1996.
Torii, N., et al., "An inhibitor for calcineurin, FK506, blocks induction of long-term depression in rat visual cortex". Neurosci Lett, 1995. 185(1): p. 1-4.
Tsai, et al., "Glutamatergic Mechanisms in Schizophrenia" *Annu Rev Pharmacol Toxicol* 42: 165-79, 2002.
Tuschl, et al., "Expanding Small RNA Inteferference" *Nat. Biotechnol.* 20: 446-448, 2002.
Underhill, et al., "Detection of Numerous Y Chromosome Biallelic Polymorphisms by Denaturing High-Performance Liquid Chromatography" *Genome Research*, 7(10): 996-1005, 1997.
Usiskin, et al., "Velocardiofacial Syndrome in Childhood-Onset Schizophrenia" *J. Am. Acad. Child Adolesc. Psychiatry* 38: 1536-1543, 1999.
Usman, et al., "Design, Synthesis, and Function of Therapeautic Hammerhead Ribozymes" *Nucl. Acids Mol. Biol.* 10: 243,1996.
Usman, et al., "Hammerhead Ribozyme Engineering" *Curr. Opin. Struct. Biol.* 1: 527, 1996.
Varga, et al., "Antisense Strategies: Functions and Applications in Immunology" *Immun. Lett.* 69: 217, 1999.
Vaughan, et al., "Human Antibodies by Design" *Nature Biotechnology* 16: 535-539, 1998.

Velculesco, et al., "Serial Analysis of Gene Expression" *Science* 270: 484-487, 1995.

Vidal, M. and Endoh, H. Trends Biotechnol;17(9):374-81, 1999.

Wagner, et al., The State of the Art in Antisense Research *Nat. Medicine* 1:1116, 1995.

Wall, et al., "Insights from Linked Single Nucleotide Polymorphisms: What We can Learn from Linkage Disequilibrium" 11: 647-651, 2001.

Watanabe, T., et al., Proc Natl Acad Sci U S A; 98(6):3080-5, 2001.

White et al., "Phencyclidine treatment 1-79 in newborn rats: Behavioral and neurochemical effects" *Society for Neuroscience Abstracts*, 27(1):1112, 2001.

Winoto, et al., "A Novel, Inducible and T cell-Specific Enhancer Located at the 3' End of the T Cell Receptor α locus" *EMBO J.* 8: 729, 1989.

Winter, et al., "Making Antibodies by Phage Display Technology" *Annu. Rev. Immunol.* 12: 433-455, 1994.

Woolf, et al.,"The Stability, Toxicity, and Effectiveness of Unmodified and Phosporothioate Antisense Oligodeoxynucleotides in Xenopus Oocytes and Embryos" *Nucleic Acids Res.* 18: 1763, 1990.

Wright, et al., "Genetic Association of the HLA DRB1 Gene Locus on Chromosome 6p21.3 with Schizophrenia" *Am J Psychiatry* 153: 1530-3, 1996.

Written Opinion for PCT/US04/21030 (Nov. 1, 2005).

Wu, et al., "The Ligation Amplification Reaction (LAR)-Amplification of Specific DNA Sequences Using Sequential Rounds of Template-Dependent Ligation" *Genomics* 4: 560, 1989.

Xu, et al., "Beta Globin Gene Inhibition by Antisense RNA Transcripts" *Gene Therapy* 7: 438, 2000.

Yakel, J., Trends in Pharmacological Science, 18: 124-134, 1997.

Yamada, et al., *Proc. Natl. Acad. Sci. USA*, 104(8):2815-2820, 2007.

Yamagata, et al., "Egr3/Pilot, a Zinc Finger Transcription Factor, is Rapidly Regulated by Activity in Brain Neurons and Colocalizes with Egr1/zif268" *Learn Mem* 1: 140-52, 1994.

Yoshino, et al., "Early Growth Response Gene-1 Regulates the Expression of the Rat Luteinizing Hormone Receptor Gene." *Biol Reprod.* 66(6): 1813-9, 2002.

Yu, et al., "RNA Interference by Expression of Short-Interfering RNAs and Hairpin RNAs in Mammalian Cells" *Proc. Natl. Acad. Sci.* 99(9): 6047-6052, 2002.

Zeng, et al., "Both Natural and Designed Micro RNAs Can Inhibit the Expression of Cognate mRNAs When Expressed in Human Cells" *Molecular Cell* 9: 1-20, 2002.

Zeng, et al., "Forebrain-Specific Calcineurin Knockout Selectively Impairs Bidirectional Synaptic Plasticity and Working/Episodic-Like Memory" *Cell* 107: 617-29, 2001.

Zeng, H., et al., *Cell*, vol. 107, 617-629, 1991.

Zhuo, M., et al., "A selective role of calcineurin aalpha in synaptic depotentiation in hippocampus". Proc Natl Acad Sci U S A, 1999. 96(8): p. 4650-5.

Zukin, R., *Am J Psychiatry*, Oct;148(10):1301-8, 1991.

\* cited by examiner

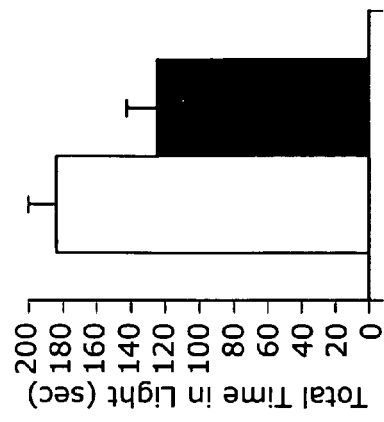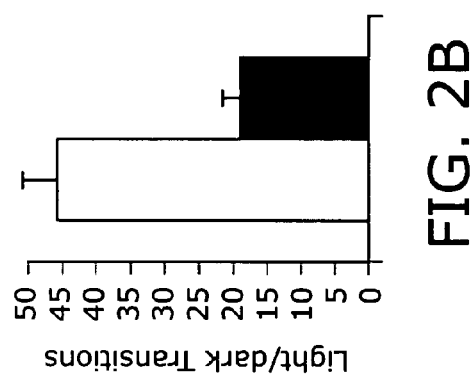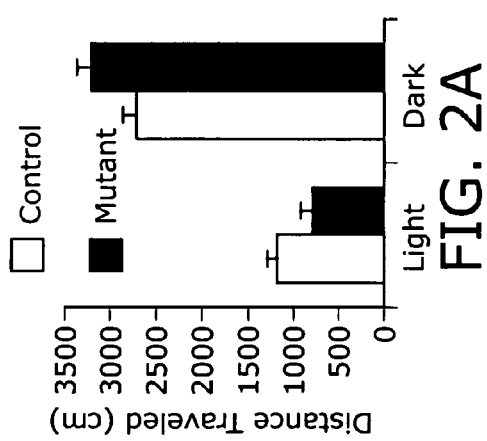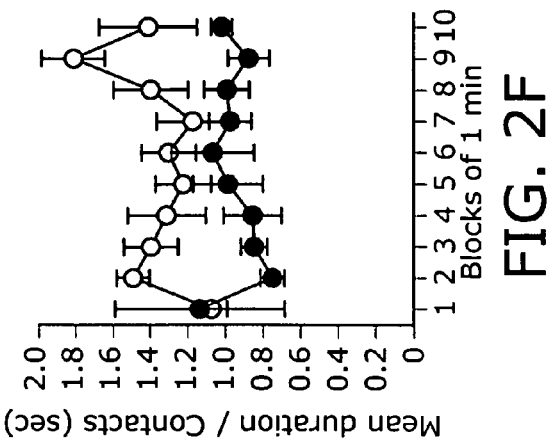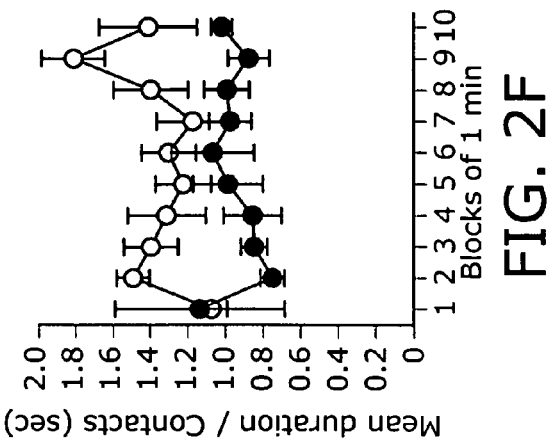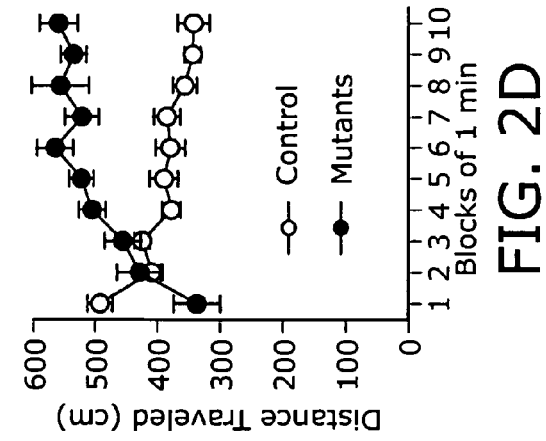
FIG. 2A FIG. 2B FIG. 2C
FIG. 2D FIG. 2E FIG. 2F

SEQUENCE LISTING

<160> NUMBER OF SEQ ID NOS: 7

<210> SEQ ID NO 1
<211> LENGTH: 18
<212> TYPE: DNA
<213> ORGANISM: Artificial Sequence

```
<220> FEATURE:
<223> OTHER INFORMATION: Description of Artificial Sequence: Forward
      PCR Primers contained 19-21 bp of homologous sequence.

<400> SEQUENCE: 1
tgtaaaacga cggccagt                                                       18

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence:Reverse
      PCR primers contained 19-21 bp of homologous sequence.

<400> SEQUENCE: 2
caggaaacag ctatgacc                                                       18

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Forward
      primer from PPP3CC exon 1.

<400> SEQUENCE: 3
gcgcttccac ctctccacc                                                      19

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Reverse
      primer from PPP3CC exon 2.

<400> SEQUENCE: 4
ctatcatagt cttctcttgc ctc                                                 23

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence:Primer
      pair 2 consists of a forward primer.

<400> SEQUENCE: 5
cccattcatg acttagagtc c                                                   21

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence:Reverse
      primer from PPP3CB exon 14.

<400> SEQUENCE: 6
cccctttata gcacaagact tc                                                  22

<210> SEQ ID NO 7
<211> LENGTH: 29
<212> TYPE: DNA
<213> ORGANISM: Artificial Sequence
<220> FEATURE:
<223> OTHER INFORMATION: Polymorphism sequence: insert in PPP3R1
```

```
<400> SEQUENCE: 7
gccggcccgc gcgcgccccc gcctccgcc                                    29
```

IDENTIFYING CALCINEURIN ACTIVATORS FOR TREATMENT OF SCHIZOPHRENIA

CROSS-REFERENCE TO RELATED APPLICATIONS

This application claims priority to U.S. Provisional Application No. 60/367,944, filed Mar. 26, 2002, and U.S. Provisional Application No. 60/452,813, entitled "Methods for Diagnosis and Treatment of Schizophrenia and Other Psychiatric Disorders and Related Reagents and Methods of Use Thereof", filed Mar. 7, 2003, listing as inventors Gerber, Karayiorgou, Miyakawa, and Tonegawa. The contents of these applications are incorporated herein by reference.

GOVERNMENT SUPPORT

The United States Government has provided grant support utilized in the development of the present invention. In particular, P50-MH58880, awarded by the National Institute of Health; R01-MH61399, awarded by the National Institute of Health have supported development of this invention. The United States Government may have certain rights in the invention.

BACKGROUND

Schizophrenia is a severe psychiatric condition that affects approximately one percent of the population worldwide (Lewis, D. A. & Lieberman, J. A. (2000) Neuron 28, 325-3). The disease is characterized by a variety of so-called "positive" symptoms that tend to occur episodically, including hallucinations, delusions, paranoia, and psychosis and/or relatively persistent symptoms such as flattened affect, social withdrawal, impaired attention, and cognitive impairments. Symptoms in the latter category are frequently referred to as "negative symptoms".

Studies of the inheritance of schizophrenia have revealed that it is a multi-factorial disease characterized by multiple genetic susceptibility elements, each likely contributing a modest increase in risk (Karayiorgou, M. & Gogos, J. A. (1997) Neuron 19, 967-79). Family linkage studies and studies of chromosomal abnormalities associated with schizophrenia have identified a number of schizophrenia susceptibility loci (Karayiorgou, M. & Gogos, J. A. (1997) Neuron 19, 967-79; Thaker, G. K. & Carpenter, W. T., Jr. (2001) Nat Med 7, 667-71). These loci encompass relatively large chromosomal regions and can contain hundreds of genes. Therefore, the identification of specific susceptibility genes in these regions is challenging.

In addition to direct genetic analysis, a longstanding body of pharmacological studies has led to the prevailing hypotheses that dysfunction of dopaminergic or NMDA receptor-mediated signaling are major contributing factors in schizophrenia pathogenesis (Seeman, P. (1987) Synapse 1, 133-52; Carlsson, A., et al., (2001) Annu Rev Pharmacol Toxicol 41, 237-60). The dopamine hypothesis for the pathophysiology of schizophrenia maintains that dysfunction of the dopamine neurotransmitter system plays a key role in the abnormalities that occur in schizophrenia. This hypothesis stems from the observation that many drugs effective in treating schizophrenia share the common property of blocking dopamine receptors. In addition, certain of the symptoms of schizophrenia can be reproduced by drugs such as amphetamine that act positively on the dopaminergic system. The glutamate dysfunction hypothesis provides an alternate, and not necessarily inconsistent potential explanation for the etiology of schizophrenia. This hypothesis arose from the observation that exposure to certain compounds such as phencyclidine (PCP) and MK-801, which act as antagonists of NMDA receptors (physiological receptors for glutamate), leads to development of schizophrenia-like symptoms. (See, e.g., Javitt, D. and Zukin, R., Am J Psychiatry, October 1991; 148(10):1301-8. Despite the appeal of these hypotheses, convincing direct genetic, physiological, or biochemical evidence for association of dopamine receptors or NMDA receptors with schizophrenia has not been obtained. In addition, although various pharmacological agents for the treatment of schizophrenia exist and are widely used, no truly satisfactory therapy exists.

Thus there remains a need in the art for improved understanding of the etiology of schizophrenia. In addition, there remains a need in the art for improved methods and reagents for the diagnosis and treatment of schizophrenia and susceptibility to schizophrenia.

SUMMARY OF THE INVENTION

The present invention relates to the identification of targets for the diagnosis and treatment of schizophrenia and related conditions. The invention encompasses the observation that calcineurin mutant mice have a phenotype suggestive of schizophrenia and that locations of calcineurin subunit genes and numerous other genes encoding polypeptides that play a role in calcineurin signaling are coincident with schizophrenia susceptibility loci. These discoveries implicate calcineurin (abbreviated herein as CaN or CN) and components of the calcineurin signaling pathway in the pathogenesis of schizophrenia and/or related conditions.

In another aspect, the invention provides a variety of methods for diagnosis of schizophrenia or related conditions, e.g., by modulating calcineurin activity and/or calcium homeostasis. For example, the invention provides a method for the diagnosis of schizophrenia or schizophrenia susceptibility comprising: (i) providing a sample obtained from a subject to be tested for schizophrenia or schizophrenia susceptibility; and (ii) detecting a polymorphic variant of a polymorphism in a coding or noncoding portion of a gene encoding a calcineurin subunit or encoding a calcineurin interacting molecule, or detecting a polymorphic variant of a polymorphism in a genomic region linked to such a gene, in the sample. The invention further provides a method for the diagnosis of schizophrenia or schizophrenia susceptibility comprising: (i) providing a sample obtained from a subject to be tested for schizophrenia or schizophrenia susceptibility; and (ii) detecting an alteration or variation in expression or activity of a calcineurin subunit or a calcineurin interacting molecule in the sample, relative to the expression or activity of the calcineurin subunit or calcineurin interacting molecule that would be expected in a sample obtained from a normal subject. Based on the discovery of an association between the PPP3CC gene (encoding CNAγ) and schizophrenia, the invention provides a risk haplotype associated with schizophrenia susceptibility.

In another aspect, the invention provides methods for the detection of polymorphisms, mutations, variations, alterations in expression, etc., in such genes and/or in their mRNA or protein expression products for use in the diagnosis of schizophrenia or related conditions or susceptibility to schizophrenia or related conditions. Such methods are useful for various purposes, including diagnosis.

According to another aspect, the invention provides a number of different in vitro and in vivo methods of screening for compounds useful in treating schizophrenia and/or related conditions including methods of screening for compounds in various animal models.

In another aspect, the invention provides compounds identified according to these screening methods, and pharmaceutical compositions including these compounds.

In another aspect, the invention provides a variety of methods of treating schizophrenia or susceptibility to schizophrenia. For example, the invention provides a method for treating schizophrenia or susceptibility to schizophrenia comprising: (i) providing a subject at risk of or suffering from schizophrenia; and (ii) administering a compound that modulates activity or abundance of calcineurin, a calcineurin subunit, or a calcineurin interacting molecule to the subject. The invention further provides a method for treating schizophrenia or susceptibility to schizophrenia comprising: (i) providing a subject at risk of or suffering from schizophrenia; and (ii) administering a compound that modulates intracellular calcium levels to the subject. The compounds for use in the various treatment methods described herein may be identified according to any of the inventive screens described herein, or using other approaches. The invention also provides a method for treating schizophrenia or susceptibility to schizophrenia comprising: (i) providing a subject at risk of or suffering from schizophrenia; and (ii) administering a compound that modulates hippocampal or cortical LTD to the subject. The invention additionally provides a method for treating schizophrenia or susceptibility to schizophrenia comprising: (i) providing a subject at risk of or suffering from schizophrenia; and (ii) administering a compound that modulates expression or activity of one or more NFAT-regulated proteins. The invention further provides a method for treating an immune system condition in a subject having schizophrenia or susceptibility to schizophrenia comprising: (i) providing a subject at risk of or suffering from an immune system abnormality and at risk of or suffering from schizophrenia; and (ii) administering a compound that modulates activity or abundance of calcineurin, a calcineurin subunit, or a calcineurin interacting molecule to the subject.

The invention further provides reagents such as oligonucleotides, oligonucleotide arrays, antibodies, and transgenic mice, including knockout and knockdown mice, and methods for their use in performing screens for compounds useful in treating schizophrenia or related conditions.

The contents of all patents, patent applications, journal articles, books, and other references cited are incorporated herein by reference. In addition, the following standard reference works are incorporated herein by reference: *Current Protocols in Molecular Biology, Current Protocols in Immunology, Current Protocols in Protein Science*, and *Current Protocols in Cell Biology*, John Wiley & Sons, N.Y., edition as of March 2002; Sambrook, Russell, Sambrook, *Molecular Cloning: A Laboratory Manual*, $3^{rd}$ ed., Cold Spring Harbor Laboratory Press, Cold Spring Harbor, 2001; and *Using Antibodies: A Laboratory Manual*, Harlow, E. and Lane, D. (Editors) New York: Cold Spring Harbor Laboratory Press, 1998.

BRIEF DESCRIPTION OF THE DRAWING

FIG. 1 presents plots of data showing increased locomotor activity, increased exploratory behavior towards inanimate objects, and increased stereotyped behavior in CNB-deficient mice.

FIG. 2 presents data showing decreased social interaction and increased anxiety-like behavior in CNB-deficient mice. FIG. 2A compares the total distance traveled by wild type and CNB-deficient mice during the open field test. FIG. 2B compares the number of transitions between the light and dark compartments by wild type and CNB-deficient mice during the open field test. FIG. 2C compares the total amount of time spent in the light compartment by wild type and CNB-deficient mice during the open field test. FIG. 2D compares distance traveled by wild type and CNB-deficient mice during the social interaction test. FIG. 2E compares the number of active contacts made by wild type and CNB-deficient mice during the social interaction test. FIG. 2F compares the mean duration of contacts made by wild type and CNB-deficient mice during the social interaction test.

FIG. 5 presents schematic illustrations of calcineurin and its related molecules.

FIG. 6 is a schematic diagram of the PPP3CC locus. The location of the PPP3CC gene in the 8p21.3 region is depicted in relation to relevant markers from linkage studies in FIG. 6A. FIG. 6B presents an expanded view of the PPP3CC gene including the exon/intron structure and the locations of the SNPs used for association studies and the coding sequence mutation identified in exon 5. D8S136: Pulver et al., 1995, Brzustowicz et al., 1999; D8S1771: Blouin et al., 1998, Gurling et al., 2001; D8S1752: Blouin et al., 1998; D8S1715, D8S133: Kendler et al., 1996. Distances and positions in this figure are according to the November 2002, human draft sequence. FIG. 6C shows haplotype distribution and transmission at the PPP3CC locus. T/nT: Transmitted/non-Transmitted.

DEFINITIONS

Figure 1A:
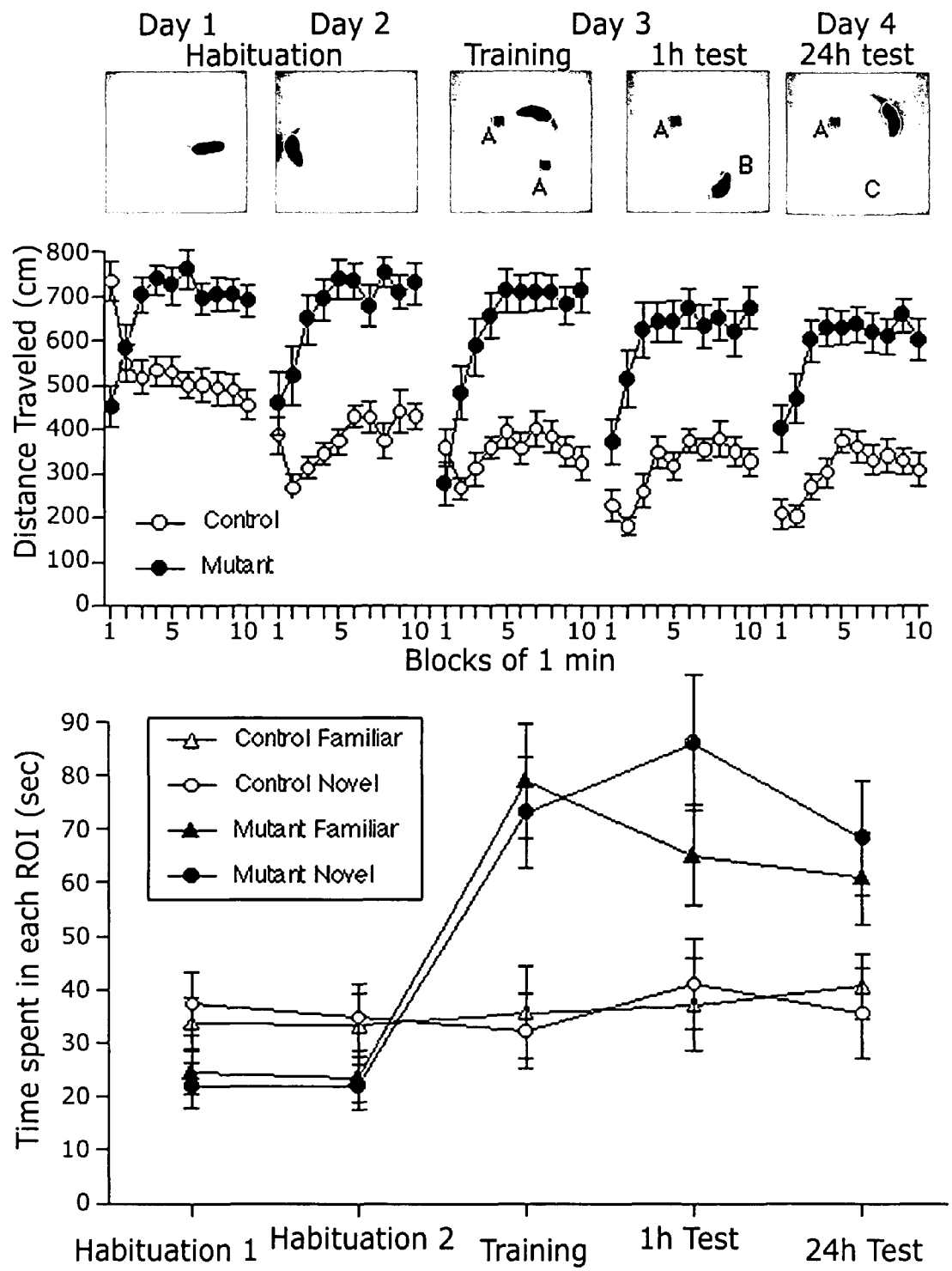
FIG. 1A compares performance of wild type and mutant mice in the object exploration test.

The term agonist refers to a molecule that increases or prolongs the duration of the effect of a polypeptide or a nucleic acid. Agonists may include proteins, nucleic acids, carbohydrates, lipids, small molecules, ions, or any other molecules that modulate the effect of the polypeptide or nucleic acid. An agonist may be a direct agonist, in which case it is a molecule that exerts its effect by binding to the polypeptide or nucleic acid, or an indirect agonist, in which case it exerts its effect via a mechanism other than binding to the polypeptide or nucleic acid (e.g., by altering expression or stability of the polypeptide or nucleic acid, by altering the expression or activity of a target of the polypeptide or nucleic acid, by interacting with an intermediate in a pathway involving the polypeptide or nucleic acid, etc.)

The term allele refers to one of the different forms of a gene or DNA sequence that can exist at a single locus within the genome. The term includes both naturally occurring alleles, which are typically studied in genetic linkage and association studies, and genetically engineered alleles.

The term antagonist refers to a molecule that decreases or reduces the duration of the effect of a polypeptide or a nucleic acid. Antagonists may include proteins, nucleic acids, carbohydrates, or any other molecules that modulate the effect of the polypeptide or nucleic acid. An antagonist may be a direct antagonist, in which case it is a molecule that exerts its effect by binding to the polypeptide or nucleic acid, or an indirect antagonist, in which case it exerts its effect via a mechanism other than binding to the polypeptide or nucleic acid (e.g., by altering expression or stability of the polypeptide or nucleic acid, by altering the expression or activity of a target of the polypeptide or nucleic acid, by interacting with an intermediate in a pathway involving the polypeptide or nucleic acid, etc.)

Antibody: The term antibody refers to an immunoglobulin, whether natural or wholly or partially synthetically produced. All derivatives thereof which maintain specific binding ability are also included in the term. The term also covers any protein having a binding domain which is homologous or largely homologous to an immunoglobulin binding domain. These proteins may be derived from natural sources, or partly or wholly synthetically produced. An antibody may be monoclonal or polyclonal. The antibody may be a member of any immunoglobulin class, including any of the human classes: IgG, IgM, IgA, IgD, and IgE. The antibody may be a fragment of an antibody such as an Fab, F(ab')2, Fv or other fragment that retains an antigen binding site, or a recombinantly produced scFv fragment. The term includes "humanized" antibodies in which for example, a variable domain of rodent origin is fused to a constant domain of human origin, thus retaining the specificity of the rodent antibody. It is noted that the domain of human origin need not originate directly from a human in the sense that it is first synthesized in a human being. Instead, "human" domains may be generated in rodents whose genome incorporates human immunoglobulin genes. See, e.g., Vaughan, et al., (1998), *Nature Biotechnology*, 16: 535-539. An antibody may be polyclonal or monoclonal, though for purposes of the present invention monoclonal antibodies are generally preferred.

As used herein, diagnostic information or information for use in diagnosis is any information that is useful in determining whether a patient has a disease or condition and/or in classifying the disease or condition into a phenotypic category or any category having significance with regards to the prognosis of or likely response to treatment (either treatment in general or any particular treatment) of the disease or condition. Similarly, diagnosis refers to providing any type of diagnostic information, including, but not limited to, whether a subject is likely to have a condition (such as schizophrenia), information related to the nature or classification of a disease, information related to prognosis and/or information useful in selecting an appropriate treatment.

The term gene as used herein generally has its meaning as understood in the art. However, it will be appreciated by those of ordinary skill in the art that the term may have a variety of meanings in the art, some of which include gene regulatory sequences (e.g., promoters, enhancers, etc.) and/or intron sequences, 3' untranslated regions, etc., and others of which are limited to coding sequences. It will further be appreciated that definitions of gene include references to nucleic acids that do not encode proteins but rather encode functional RNA molecules, e.g., tRNAs, stRNAs, etc. Thus the term gene may refer to a portion of a nucleic acid that encodes a protein and may optionally encompass regulatory sequences. This definition is not intended to exclude application of the term "gene" to non-protein coding expression units but rather to clarify that, in most cases, the term as used in this document refers to a nucleic acid that includes a protein coding region.

As used herein, a gene product or expression product, or gene expression product is, in general, an RNA transcribed from the gene or a polypeptide encoded by an RNA transcribed from the gene.

The term homology refers to a degree of similarity between two or more nucleic acid sequences or between two or more amino acid sequences. As is well known in the art, given any nucleotide or amino acid sequence, homologous sequences may be identified by searching databases (e.g., GENBANK® (NIH genetic sequence database), EST [expressed sequence tag] databases, GST [gene sequence tag] databases, GSS [genome survey sequence] databases, organism sequencing project databases) using computer programs such as BLASTN for nucleotide sequences and BLASTP, gapped BLAST, and PSI-BLAST for amino acid sequences. These programs are described in Altschul, S F, et al., Basic local alignment search tool, *J. Mol. Biol.*, 215(3): 403-410, 1990, Altschul, S F and Gish, W, *Methods in Enzymology*, and Altschul, S F, et al., "Gapped BLAST and PSI-BLAST: a new generation of protein database search programs", *Nucleic Acids Res.* 25:3389-3402, 1997. In addition to identifying homologous sequences, the programs mentioned above typically provide an indication of the degree of homology. Determining the degree of identity or homology that exists between two or more amino acid sequences or between two or more nucleotide sequences can also be conveniently performed using any of a variety of other algorithms and computer programs known in the art. Discussion and sources of appropriate programs may be found, for example, in Baxevanis, A., and Ouellette, B. F. F., *Bioinformatics: A Practical Guide to the Analysis of Genes and Proteins*, Wiley, 1998; and Misener, S. and Krawetz, S. (eds.), *Bioinformatics Methods and Protocols* (Methods in Molecular Biology, Vol. 132), Humana Press, 1999.

The term hybridize, as used herein, refers to the interaction between two complementary nucleic acid sequences. The phrase hybridizes under high stringency conditions describes an interaction that is sufficiently stable that it is maintained under art-recognized high stringency conditions. Guidance for performing hybridization reactions can be found, for example, in *Current Protocols in Molecular Biology*, John Wiley & Sons, N.Y., 6.3.1-6.3.6, 1989, and more recent updated editions, all of which are incorporated by reference. See also Sambrook, Russell, and Sambrook, *Molecular Cloning: A Laboratory Manual*, 3$^{rd}$ ed., Cold Spring Harbor Laboratory Press, Cold Spring Harbor, 2001. Aqueous and non-aqueous methods are described in that reference and either can be used. Typically, for nucleic acid sequences over approximately 50-100 nucleotides in length, various levels of stringency are defined, such as low stringency (e.g., 6× sodium chloride/sodium citrate (SSC) at about 45° C., followed by two washes in 0.2×SSC, 0.1% SDS at least at 50° C. (the temperature of the washes can be increased to 55° C. for medium-low stringency conditions)); 2) medium stringency hybridization conditions utilize 6×SSC at about 45° C., followed by one or more washes in 0.2×SSC, 0.1% SDS at 60° C.; 3) high stringency hybridization conditions utilize 6×SSC at about 45° C., followed by one or more washes in 0.2×SSC, 0.1% SDS at 65° C.; and 4) very high stringency hybridization conditions are 0.5M sodium phosphate, 0.1% SDS at 65° C., followed by one or more washes at 0.2×SSC, 1% SDS at 65° C.) Hybridization under high stringency conditions only occurs between sequences with a very high degree of complementarity. One of ordinary skill in the art will recognize that the parameters for different degrees of stringency will generally differ based on various factors such as the length of the hybridizing sequences, whether they contain RNA or DNA, etc. For example, appropriate temperatures for high, medium, or low stringency hybridization will generally be lower for shorter sequences such as oligonucleotides than for longer sequences. Additional examples of hybridization conditions of varying stringency are found, for example, in Ausubel, et al., *Current Protocols in Molecular Biology*, John Wiley & Sons, N.Y., edition as of March 2002.

Isolated, as used herein, means 1) separated from at least some of the components with which it is usually associated in nature; and/or 2) not occurring in nature.

As used herein, linkage or linked generally refers to genetic linkage. Two loci (e.g., a DNA marker locus and a disease locus such as a mutation causing disease) are said to be genetically linked when the probability of a recombination event occurring between these two loci is below 50% (which equals the probability of recombination between two unlinked loci). The terms linkage or linked may also refer to physical linkage. In general, two loci are physically linked when they are present on the same contiguous piece of DNA. The greater the physical distance between the two loci, the less the degree of physical linkage. It will be appreciated that although there is a correspondence between genetic and physical linkage, the correspondence may be imprecise and can be nonlinear. For example, two loci that are separated by any particular number of bases may be closely linked genetically if the recombination frequency in the region between the loci is low, but may be essentially genetically unlinked or only weakly linked if the recombination frequency between the two loci is high.

The term oligonucleotide refers to a single stranded nucleic acid (typically DNA) ranging in length from 2 to approximately 70 bases. Oligonucleotides are often synthetic but can also be produced from naturally occurring polynucleotides. An oligonucleotide probe or primer is an oligonucleotide capable of binding to a target nucleic acid of complementary sequence through one or more types of chemical bonds, usually through complementary pairing via hydrogen bond formation. Oligonucleotide probes and/or primers are often 5 to 60 bases and in specific embodiments may be between 10 and 40, or 15 and 30 bases long. An oligonucleotide probe or primer may include natural (e.g., A, G, C or T) or modified bases (7-deazaguanosine, inosine, etc.). In addition, the bases may be joined by a linkage other than a phosphodiester bond, such as a phosphoramidite linkage or a phosphorothioate linkage, or they may be peptide nucleic acids in which the constituent bases are joined by peptide bonds rather than by phosphodiester bonds, so long as such linkages do not interfere with hybridization. Any of the oligonucleotides described herein may be provided in isolated form or purified form.

The term operably linked, in reference to nucleic acids, refers to a relationship between two nucleic acid sequences wherein the expression or processing of one of the nucleic acid sequences is controlled by, regulated by, modulated by, etc. the other nucleic acid sequence. For example, a promoter is operably linked with a coding sequence if the promoter controls transcription of the coding sequence. Preferably a nucleic acid sequence that is operably linked to a second nucleic acid sequence is covalently linked, either directly or indirectly, to such a sequence, although any effective three-dimensional association is acceptable. The term may be generally applied to any nucleic acid or polypeptide that regulates the expression, processing, localization, transport, etc., of a second nucleic acid or polypeptide, generally one to which it is chemically or physically bound (e.g., covalently linked, hydrogen bonded, associated via ionic bonds).

The term polymorphism refers to the occurrence of two or more alternative sequences or alleles in a population. A polymorphic site is a location at which differences in genomic DNA sequence exist among members of a population. A polymorphic variant is any of the alternate sequences or alleles that may exist at a polymorphic site among members of a population. For purposes of the present invention, the term population may refer to the population of the world, or to any subset or group of individuals. Thus the term polymorphic variant as used herein generally refers to naturally occurring variants as opposed, for example, to variants created by recombinant DNA technology. However, the term includes variants created by recombinant DNA technology when such variants replicate or duplicate naturally occurring variants. Replication or duplication of naturally occurring variants is intended to include recapitulation of a naturally occurring human variant either in a different human genetic background or in an animal model such as a mouse (e.g., the creation of a mutation at a corresponding site within mouse genomic DNA).

Typically, for the various methods described herein (e.g., diagnostic methods, methods for identifying causative mutations, etc.) described herein, it will be of interest to determine which polymorphic variant is present in a subject, among multiple polymorphic variants that exist within a population.

The term primer refers to a single-stranded oligonucleotide which acts as a point of initiation of template-directed DNA synthesis under appropriate conditions (e.g., in the presence of four different nucleoside triphosphates and a polymerization agent, such as DNA polymerase, RNA polymerase or reverse transcriptase) in an appropriate buffer and at a suitable temperature. The appropriate length of a primer depends on the intended use of the primer, but typically ranges from approximately 10 to approximately 30 nucleotides. Short primer molecules generally require lower temperatures to form sufficiently stable hybrid complexes with the template. A primer need not be perfectly complementary to the template but should be sufficiently complementary to hybridize with it. The term primer site refers to the sequence of the target DNA to which a primer hybridizes. The term "primer pair" refers to a set of primers including a 5' (upstream) primer that hybridizes with the 5' end of a DNA sequence to be amplified and a 3' (downstream) primer that hybridizes with the complement of the 3' end of the sequence to be amplified. These primers are also referred to as forward and reverse primers respectively.

Purified, as used herein, means separated from many other compounds or entities. A compound or entity may be partially purified, substantially purified, or pure, where it is pure when it is removed from substantially all other compounds or entities, i.e., is preferably at least about 90%, more preferably at least about 91%, 92%, 93%, 94%, 95%, 96%, 97%, 98%, 99%, or greater than 99% pure.

The term regulatory sequence or regulatory element is used herein to describe a region of nucleic acid sequence that directs, enhances, or inhibits the expression (particularly transcription, but in some cases other events such as splicing or other processing) of sequence(s) with which it is operatively linked. The term includes promoters, enhancers and other transcriptional control elements. In some embodiments of the invention, regulatory sequences may direct constitutive expression of a nucleotide sequence; in other embodiments, regulatory sequences may direct cell type or tissue-specific and/or inducible expression. For instance, non-limiting examples of tissue-specific promoters appropriate for use in mammalian cells include lymphoid-specific promoters (see, for example, Calame et al., *Adv. Immunol.* 43:235, 1988) such as promoters of T cell receptors (see, e.g., Winoto et al., *EMBO J.* 8:729, 1989) and immunoglobulins (see, for example, Banerji et al., *Cell* 33:729, 1983; Queen et al., *Cell* 33:741, 1983), and neuron-specific promoters (e.g., the neurofilament promoter; Byrne et al., *Proc. Natl. Acad. Sci. USA* 86:5473, 1989). Developmentally-regulated promoters are also encompassed, including, for example, the murine hox promoters (Kessel et al., *Science* 249:374, 1990) and the α-fetoprotein promoter (Campes et al., *Genes Dev.* 3:537, 1989).

As used herein, a sample obtained from a subject may include, but is not limited to, any or all of the following: a cell or cells, a portion of tissue, blood, serum, ascites, urine, saliva, amniotic fluid, cerebrospinal fluid, and other body fluids, secretions, or excretions. The sample may be a tissue sample obtained, for example, from skin, muscle, buccal or conjunctival mucosa, placenta, gastrointestinal tract or other organs. A sample of DNA from fetal or embryonic cells or tissue can be obtained by appropriate methods, such as by amniocentesis or chorionic villus sampling.

The term sample also includes any material derived by isolating, purifying, and/or processing such a sample. Derived samples may include nucleic acids or proteins extracted from the sample or obtained by subjecting the sample to techniques such as amplification or reverse transcription of mRNA, etc.

A short, interfering RNA (siRNA) comprises an RNA duplex that is approximately 19 basepairs long and optionally further comprises one or two single-stranded overhangs or loops. An siRNA may comprise two RNA strands hybridized together, or may alternatively comprise a single RNA strand that includes a self-hybridizing portion. When siRNAs include one or more free strand ends, it is generally preferred that free 5' ends have phosphate groups, and free 3' ends have hydroxyl groups. In certain embodiments of the invention, one strand of the siRNA (or, the self-hybridizing portion of the siRNA) is precisely complementary with a region of the target transcript, meaning that the siRNA hybridizes to the target transcript without a single mismatch. However, in other embodiments of the invention perfect complementarity is not necessary. For certain siRNAs (e.g., microRNAs), perfect complementarity is not desirable.

An siRNA is considered to be targeted for the purposes described herein if 1) the stability of the target gene transcript is reduced in the presence of the siRNA as compared with its absence; and/or 2) the siRNA shows at least about 90%, more preferably at least about 91%, 92%, 93%, 94%, 95%, 96%, 97%, 98%, 99%, or 100% precise sequence complementarity with the target transcript for a stretch of at least about 17, more preferably at least about 18 or 19 to about 21-23 nucleotides; and/or 3) the siRNA hybridizes to the target transcript under stringent conditions.

As used herein, the term specific binding refers to an interaction between a target polypeptide (or, more generally, a target molecule) and a binding molecule such as an antibody, agonist, or antagonist, which may be a small molecule. The interaction is typically dependent upon the presence of a particular structural feature of the target polypeptide such as an antigenic determinant or epitope recognized by the binding molecule (e.g., in the case of an antibody). For example, if an antibody is specific for epitope A, the presence of a polypeptide containing epitope A or the presence of free unlabeled A in a reaction containing both free labeled A and the antibody thereto, will reduce the amount of labeled A that binds to the antibody. It is to be understood that specificity need not be absolute. For example, it is well known in the art that numerous antibodies cross-react with other epitopes in addition to those present in the target molecule. Such cross-reactivity may be acceptable depending upon the application for which the antibody is to be used. Thus the degree of specificity of an antibody will depend on the context in which it is being used. In general, an antibody exhibits specificity for a particular partner if it favors binding of that partner above binding of other potential partners. One of ordinary skill in the art will be able to select antibodies having a sufficient degree of specificity to perform appropriately in any given application (e.g., for detection of a target molecule, for therapeutic purposes, etc). In the case of small molecules, interaction is also typically dependent upon the presence of a particular structural feature of the target polypeptide, e.g., a cleft or three-dimensional pocket into which the small molecule fits, etc.

It is also to be understood that specificity may be evaluated in the context of additional factors such as the affinity of the binding molecule for the target polypeptide versus the affinity of the binding molecule for other targets, e.g., competitors. If a binding molecule exhibits a high affinity for a target molecule that it is desired to detect and low affinity for nontarget molecules, the binding molecule will likely be an acceptable reagent, e.g., for diagnostic and/or therapeutic purposes. Once the specificity of a binding molecule is established in one or more contexts, it may be employed in other, preferably similar, contexts without necessarily re-evaluating its specificity.

As used herein, treating includes reversing, alleviating, inhibiting the progress of, preventing, or reducing the likelihood of the disease, disorder, or condition to which such term applies, or one or more symptoms or manifestations of such disease, disorder or condition.

The term vector is used herein to refer to a nucleic acid molecule capable of mediating entry of, e.g., transferring, transporting, etc., another nucleic acid molecule into a cell.

The transferred nucleic acid is generally linked to, e.g., inserted into, the vector nucleic acid molecule. A vector may include sequences that direct autonomous replication, or may include sequences sufficient to allow integration into host cell DNA. Useful vectors include, for example, plasmids, cosmids, and viral vectors. Viral vectors include, e.g., replication defective retroviruses, adenoviruses, adeno-associated viruses, and lentiviruses. As will be evident to one of ordinary skill in the art, viral vectors may include various viral components in addition to nucleic acid(s) that mediate entry of the transferred nucleic acid.

DETAILED DESCRIPTION OF CERTAIN EMBODIMENTS

I. Overview

Calcineurin is a calcium-dependent protein phosphatase that plays an important role in $Ca^{2+}$-mediated signal transduction. Since its original identification in extracts of mammalian brain, calcineurin has been implicated in a variety of biological responses including, for example, lymphocyte activation, neuronal and muscle development, neurite outgrowth, and morphogenesis of vertebrate heart valves. Calcineurin has also been shown to have important roles in axonal guidance (Chang, H., et al. (1995) Nature 376, 686-690; Xeng, H., et al., Cell, Vol 107, 617-629, 1991) in addition to learning and memory, In addition to the various calcineurin subunits and isoforms (see below), a number of other molecules play a role in calcineurin activity. These molecules include, for example, proteins that regulate calcineurin abundance and/or activity (either indirectly or via direct physical interaction), substrates, etc. The genomic locations of genes encoding calcineurin and many of the molecules involved in calcineurin signaling have been identified.

In order to further investigate the role of calcineurin in learning and memory the inventors employed gene targeting technologies to reduce or eliminate expression of CNB1, the only known regulatory subunit of brain calcineurin, in the excitatory neurons of the adult mouse forebrain by knocking out the CNB1 gene (also referred to herein as PPP3R1). In addition to deficits in bidirectional synaptic plasticity and working/episodic-like memory (described in Zeng, H., et al., Cell, Vol 107, 617-629, 1991) the inventors discovered that these mice (referred to herein as CNB-deficient mice, CNB mutant mice, or CNB knockout mice) display a number of abnormalities in behavior and activity that are suggestive of schizophrenia. In particular, as described in Example 1, CNB-deficient mice exhibited increases in (1) locomotor activity; (2) stereotyped behavior; (3) exploratory behavior towards inanimate objects; and (4) anxiety-like behavior. CNB mutant mice also displayed decreased social interaction, impaired prepulse inhibition, impaired latent inhibition, and impaired nesting behavior. Most or all of these abnormalities are considered to indicate disturbances in cognitive functioning corresponding to disturbances found in human subjects suffering from schizophrenia and/or related conditions. Many of them are also found in other currently available genetic mouse models and/or in mice treated with pharmacological compounds (e.g., cocaine, PCP, known to induce schizophrenia-like symptoms in human subjects.

As discussed in more detail below, while the cause of schizophrenia has not been identified, genetic factors are known to be important. A large number of genomic regions have been identified as susceptibility loci through genetic studies, and it is believed that mutations or variations within those regions contribute to schizophrenia pathogenesis, though no individual gene, mutation, or variation has been definitively shown to play a role. Prompted by their discovery that CNB-deficient mice exhibit phenotypes suggestive of schizophrenia, the inventors investigated the possibility that, in humans, calcineurin and/or other genes involved in calcineurin signaling may be located at or close to genomic regions identified as schizophrenia susceptibility loci.

As described in more detail in Example 2, the inventors discovered a striking coincidence between the locations of genes encoding various calcineurin subunits, isoforms, and other molecules involved in calcineurin signaling and loci believed to be involved in schizophrenia susceptibility. In other words, the genomic locations of sequences encoding calcineurin subunits, isoforms, and other molecules involved in calcineurin signaling are located within or in close proximity to sites believed to harbor mutations or variations that contribute to schizophrenia pathogenesis. These discoveries implicate calcineurin and other components of calcineurin signaling pathways in the pathogenesis of schizophrenia and/or related conditions. These molecules and the genes that encode them (discussed further below) are referred to collectively herein as "calcineurin interacting molecules" and "calcineurin interacting genes" or as "calcineurin signaling molecules" and "calcineurin signaling genes".

By identifying the key role played by calcineurin signaling molecules in susceptibility to schizophrenia, the invention provides a framework that would explain both the genetic complexity and underlying molecular basis of schizophrenia and/or related conditions. In addition, by identifying particular candidate genes rather than merely large genomic regions, the invention allows application of a systematic method for identifying genetic mutations or alterations that contribute to susceptibility to and/or development of schizophrenia. This systematic method for identifying genetic mutations or alterations that contribute to susceptibility to and/or development of schizophrenia is one aspect of the invention.

As further described in Examples 3 and 4, the inventors have extended their initial findings and applied the inventive method for identifying genetic mutations or alterations that result in susceptibility to or development of schizophrenia by sequencing portions of a subset of calcineurin signaling genes to identify polymorphisms in these genes and by performing association studies to examine association of polymorphisms (e.g., polymorphic variants) in these genes with disease in a sample of families having one or more members affected with schizophrenia. The inventors have discovered an association between the PPP3CC gene and schizophrenia susceptibility and have identified particular risk haplotypes. In addition, as described in Example 5, the inventors have shown that PPP3CC is expressed in the adult and fetal human brain, further supporting its involvement in schizophrenia.

While not wishing to be bound by any theory, the inventors suggest several possible mechanisms by which altered calcineurin function could contribute to schizophrenia pathogenesis. Calcium-dependent activation of calcineurin activity leads to dephosphorylation of DARPP-32, which is phosphorylated following dopamine D1 receptor activation, and of the related inhibitor of protein phosphatase-1, inhibitor-1 (Mulkey, et al 1994, Greengard, et al 1999). Normal calcineurin function may be required for calcium dependent regulation of downstream events in the D1-mediated dopaminergic signaling cascade. In addition, calcineurin is required for certain types of NMDA receptor-dependent synaptic plasticity including long term depression (LTD) (Mulkey, et al 1994, Zeng, et al, 2001). Thus, altered calcineurin activity is likely to affect the range of bidirectional synaptic modification. The involvement of calcineurin in dopaminergic and glutamatergic signaling events raises the possibility that calcineurin function is required as a critical link between these two neurotransmitter systems.

A complex of calcineurin and dynamin-1 has been shown to be involved in regulation of clathrin-mediated endocytosis (Lai, M. M., et al., *J Biol Chem* 274, 25963-6, 1999). This process has been implicated in endocytosis of synaptic vesicles (Lai, et al. 1999) and AMPA receptors (Haucke, V. (2000) *Nat Neurosci* 3, 1230-2). Altered calcineurin activity might therefore result in abnormal calcium-dependent regulation of critical synaptic endocytotic events and consequent abnormal synaptic function.

An interaction of calcineurin with the ryanodine receptor type 3 (RYR3)/inositol triphosphate receptor 1 (ITPR1) complex has been shown to regulate intracellular calcium release (Cameron, A. M., et al. (1995) Cell 83, 463-72. Furthermore, calcineurin activity has been shown to be required for expression of the ITPR1 receptor in neurons (Genazzani, A. A., Carafoli, E. & Guerini, D. (1999) Proc Natl Acad Sci USA 96, 5797-801). Therefore, altered calcineurin activity could lead to abnormal neuronal calcium homeostasis. In addition to its role in regulation of intracellular calcium release, calcineurin has recently been shown to be involved in serotonin-dependent modulation of L-type calcium channel function (Day, M., Olson, P. A., Platzer, J., Striessnig, J. & Surmeier, D. J. (2002) J Neurophysiol 87, 2490-504), suggesting that altered calcineurin activity could also lead to abnormal serotonergic modulation of calcium entry.

In addition, calcineurin is required for the NFAT-mediated transcriptional response (Crabtree, G. R. & Olson, E. N. (2002) Cell 109 Suppl, S67-79). At least one isoform of NFAT is expressed in the mammalian brain (Plyte 2001). Calcineurin activity has been shown to be required for the expression of specific genes in neurons (Genazzani 1999) consistent with the possibility that altered calcineurin activity could lead to changes in calcium-dependent neuronal transcription that could have profound effects on neuronal function.

As described further below, the invention provides methods and reagents for identifying the genetic mutations or alterations that result in susceptibility to and/or development of schizophrenia and related conditions and disorders, methods and reagents for diagnosing schizophrenia or susceptibility to schizophrenia, methods and reagents for identifying compounds to prevent or treat schizophrenia, and a variety of other methods and reagents. The next section discusses calcineurin and the other molecules involved in calcineurin signaling. The following section discusses schizophrenia and its genetic basis. Subsequent sections describe particular aspects of the invention in further detail.

II. Calcineurin and Calcineurin-Dependent Signaling Pathways

Calcineurin is a calcium-dependent serine/threonine protein phosphatase that is highly expressed in the central nervous system (Klee, C. B., Ren, H. & Wang, X. (1998) *J Biol Chem* 273, 13367-70; Shibasaki, F., Hallin, U. & Uchino, H. (2002) *J Biochem* (Tokyo) 131, 1-15; Rusnak, F. and Mertz, P., *Physiological Reviews* (2000) 80(4): 1483-1522 and references therein, all of which are incorporated by reference herein.). Calcineurin consists of a heterodimer composed of a regulatory subunit, CNB, and a catalytic subunit CNA. There are three different CNA isoforms, referred to as CNAα, CNAβ, and CNAγ, encoded by distinct genes. Binding of the CNA subunit to the $Ca^{2+}$/calmodulin complex appears to be required for activity. The CNB subunit is structurally related to calmodulin and is also needed for full CN activity. CNB, which is typically myristoylated, generally remains associated with CNA in the absence of $Ca^{2+}$, but phosphatase activity increases when $Ca^{2+}$ binds to the B subunit.

Calcineurin exerts its effects through a variety of different mechanisms. One major mechanism of action involves control of transcription via regulation of the NF-AT family of transcription factors (Shaw, J. P., et al. (1988), *Science,* 241: 202-205; Flanagan, W. M. (1991), *Nature,* 352: 803-7; Liu, J., et al. (1991), *Cell,* 66: 807-15; reviewed in Crabtree, G. (2001), *J. Biol. Chem.,* 276(4): 2313-2316, and see also references therein.) Briefly, NF-AT family members contain two components, one of which (NFATc) is present in the cytoplasm while the other (NFATn) is present in the nucleus. Calcineurin functions in the NF-AT pathway by directly dephosphorylating NF-ATc subunits, which then translocate into the nucleus where they associate with the nuclear component to form active complexes that regulate transcription of a diverse set of genes containing NF-AT responsive regulatory elements (e.g., promoters). Calcineurin also acts in a variety of other ways, including some that are independent of transcription.

Calcineurin activity plays a key role in the downstream regulation of dopaminergic signal transduction (Greengard, P. (2001) Science 294, 1024-30) and in the induction of certain forms of NMDA receptor-dependent synaptic plasticity (Mulkey, R. et al., (1994) *Nature* 369, 486-8; Zeng, H., et al., (2001) Cell 107, 617-29). See also Yakel, J. (1997), *Trends in Pharmacological Science,* 18: 124-134 and references therein. Thus calcineurin function could comprise a critical link between dopaminergic and glutamatergic signaling.

CN and/or CN subunits (CNA isoforms and/or CNB) interact (either directly, as by physical interaction, or indirectly, as by any other mechanism not requiring physical interaction) with a variety of other cellular molecules. In general, these molecules may alter any of a number of aspects of CN function, level, or activity. Alternately, the activity, level, or function of these CN-interacting molecules may be altered by the activity of CN. For example, and without intending any limitation, certain of these molecules (e.g., Cabin1) are endogenous inhibitors of CN; others are substrates (e.g., NF-ATc), channels or receptors, etc.

According to various embodiments of the invention the phrase "CN, CN subunit, or CN interacting molecule" may include, but is not limited to, molecules or molecular complexes that possess calcineurin activity or subunits thereof (e.g., molecules or molecular complexes that dephosphorylate known CN substrates at sites known to be sites of dephosphorylation by CN); molecules that alter or modulate (e.g., enhance or inhibit) calcineurin activity; molecules that regulate calcineurin expression (which includes regulation of expression of any CN subunit or other CN interacting molecule), intracellular location, and/or functional activity; calcineurin substrates; channels, pumps, or receptors that regulate intracellular calcium levels or localization so as to alter or influence CN activity; molecules that modify and/or post-translationally process CN, CN subunit(s) and/or CN interacting molecules; and molecules that enhance or antagonize the effects of calcineurin. According to certain embodiments of the invention "calcineurin interacting molecules" include calcium channels such as the capacitance regulated activation channels (CRAC; Serafini, T., et al., *Immunity,* 3, 239-250, 1995; Fanger, C., et al., *J. Cell. Biol.,* 131, 655-667, 1995; Timmerman, L., et al., *Nature,* 383, 837-40, 1996), L-type calcium channels, calcium pumps, etc. "Regulation of expression" of CN, CN subunits, or CN interacting molecules includes regulation of transcription and post-transcriptional processing (e.g., splicing, polyadenylation) and/or localization of transcripts that encode such molecules, regulation of translation of transcripts that encode such molecules, and regulation of the degradation of transcripts that encode such molecules or degradation of the molecules themselves.

It will thus be appreciated that the term "CN interacting molecule" includes but is not limited to, molecules that physically interact with CN and/or CN subunit(s). As described herein, certain of the genes that encode CN, CN subunits, and/or CN interacting molecules are coincident with previously mapped or identified schizophrenia susceptibility loci. Without intending to limit the invention to such molecules, this subset includes the following: CNB; CNAα; CNAβ; CNAγ; Cabin 1; calcineurin B homologous protein; calcipressins (e.g., DSCR-1); calsarcin-1; calsarcin-3; A kinase anchor protein 5; FK506 binding protein 5; interleukin enhancer binding factor 2 (ILF2 subunit of nuclear factor of activated T cells); nuclear factor of activated T cells, cytoplasmic, calcineurin dependent 2; ryanodine receptor type 3; IP3 (inositol triphosphate) receptor type 1; pituitary adenylate cyclase activating polypeptide (PACAP); calcium-signal modulating cyclophilin ligand; and various other molecules that interact with calcineurin activity. These molecules and others are listed in Table 1 together with their chromosomal locations and locations of coincident or nearby schizophrenia susceptibility loci. (References in Table 1 are listed in Reference List 2. Further details regarding certain of these molecules and their role in calcineurin signaling are presented in Example 2. The fact that to date no schizophrenia locus that is coincident or nearby the chromosomal location of certain CN subunits and/or CN interacting molecules may simply reflect the fact that genetic studies have thus far only identified a subset of susceptibility loci.

III. Genetic Analysis of Schizophrenia and Related Conditions

The cause of schizophrenia is unknown, but it has been shown to include a significant genetic component. Unlike disorders such as cystic fibrosis and sickle cell anemia that exhibit a Mendelian inheritance pattern and are caused by mutations in a single gene, schizophrenia is believed to be a multigenic disorder in which mutations or variations in many different genes may contribute, to different degrees and in different combinations, to development of disease. It appears likely that contributions from multiple genes are involved in any given patient, and that mutations or alterations in these genes display varying degrees of penetrance so that even if an individual harbors a mutation or alteration that may contribute to schizophrenia pathogenesis, the individual may not develop clinical disease. These features have made it difficult to conclusively determine the genetic basis of schizophrenia.

A large number of genetic studies have implicated certain regions of genomic DNA (chromosomal locations) as possibly harboring mutations or variations that contribute to development of schizophrenia Karayiorgou, M. & Gogos, J. A. (1997) Neuron 19, 967-79; Thaker, G. K. & Carpenter, W. T., Jr. (2001) Nat Med 7, 667-71). These regions are typically on the order of many kilobases or megabases in length and are referred to as "susceptibility loci" to reflect the fact that mutations or alterations somewhere within these regions are believed to confer an increased likelihood that an individual having such mutations or alterations will develop the condition. It is therefore likely that such regions harbor genes which, alone or in combinations, are causally implicated in schizophrenia in at least a subset of patients. Genetic studies include linkage studies, in which families having an increased incidence of schizophrenia relative to the incidence in the general population (referred to herein as "schizophrenia families" are studied) and association studies, in which populations typically containing both related and unrelated subjects diagnosed with schizophrenia, e.g., groups of schizophrenia families, are studied. Association studies can compare the frequencies of certain haplotypes in control and affected populations. Alternately, they can assess disequilibrium in the transmission of certain haplotypes to affected probands. In accordance with the art-accepted definition, a "haplotype" can be a specific polymorphic variant for a given polymorphism on a single chromosome, or the combination of polymorphic variants (alleles) for a group of polymorphisms represented on a single chromosome for a particular individual.

Linkage and association studies typically make use of genetic polymorphisms, i.e., differences between genomic DNA sequence that exist among members of a population at certain locations in the genome. (See, e.g., Cardon, L. and Bell, J., (2001), *Nature Reviews Genetics*, Vol. 2, pp. 91-99; Kruglyak, L. and Lander, E. (1995), *Am. J. Hum. Genet.*, 56:1212-1223; Jorde, L. B. (2000), *Genome Research*, 10:1435-1444; Pritchard, J. and Przeworski, M. (2001), *Am. J. Hum. Genet.*, 69:1-14 and references in the foregoing articles for discussion of considerations in design of genetic studies, particularly for complex traits and diseases in which multiple genes play a role, such as schizophrenia). For example, a population may contain multiple subpopulations of individuals each of which has a different DNA sequence at a particular chromosomal location. Such polymorphisms may be single nucleotide differences (single nucleotide polymorphisms, referred to herein as SNPs). (See, e.g., Nowotny, P., et al. (2001), *Curr. Op. Neurobiol.*, 11:637-641; Wall, J. (2001), 11:647-651 and references in these articles.) When SNPs occur within coding regions they may, but frequently do not, result in alterations in the amino acid sequence of the encoded protein. In general, while not wishing to be bound by any theory, SNPs are thought to arise as a result of mutations in what was originally a more homogeneous ancestral sequence. Other polymorphisms include multiple nucleotide polymorphisms, deletions (including microdeletions), insertions, inversions, translocations, etc.

It will be appreciated that while certain polymorphic variants may be responsible for disease or phenotypic variation by, for example, causing a functional alteration in an encoded protein, many polymorphisms appear to be silent in that no known detectable difference in phenotype exists between individuals having different alleles. However, polymorphisms (whether silent or not) may be physically and/or genetically linked to genes or DNA sequences in which mutations or variations confer susceptibility to and/or play a causative role in disease (i.e., they are located within a contiguous piece of DNA). In the absence of genetic recombination, polymorphisms that are physically linked to such mutations or variations will generally be inherited together with the mutation or alteration.

With increasing genetic recombination between any given polymorphism and a causative mutation or variation, the extent of co-inheritance will be reduced. Since the likelihood of genetic recombination between loci generally increases with increasing distance between the loci (though not necessarily in a linear fashion), co-inheritance of a particular polymorphism and a particular phenotype suggests that the polymorphism is located in proximity to a causative mutation or variation. Thus studying the co-inheritance of polymorphic variants, e.g., SNPs, allows identification of genomic regions likely to harbor a mutation or variation that, alone or in combination with other mutations or variations, causes or increases susceptibility to disease. Polymorphisms are thus useful for genetic mapping and identification of candidate genes, in which mutations or variations may play a causative role in disease. In addition, detection of particular polymorphic variants (alleles) is useful for diagnosis of disease or susceptibility to disease as described herein.

Linkage and association studies have identified a large number of schizophrenia susceptibility loci. See, for example, references 1-24 of the reference list for Examples 3 and 4 and United States Published Patent Application 20020165144. These references are merely representative, and one of ordinary skill in the art will be able to perform literature searches to learn of additional such loci. In addition, a number of candidate genes located near or within schizophrenia susceptibility regions identified from genetic studies have been suggested to play a role in the etiology of schizophrenia. (See, e.g., Straub, R. E., et al., *Am. J. Hum. Genet.* (2002) 71: 337-348; Stefannson, H., et al., *Am. J. Hum. Genet.* (2002) 71: 877-892; However, definitive proof of the involvement of any of these candidate genes in schizophrenia is lacking.

Schizophrenia is one of a group of psychiatric conditions and disorders that exhibit a spectrum of similar phenotypes. Many of these conditions and disorders are found at increased frequency in family members of schizophrenic subjects, relative to their incidence in the general population. These factors make it likely that the same genetic mutations or alterations that contribute to schizophrenia susceptibility and/or pathogenesis are also involved in susceptibility to and/or pathogenesis of these conditions and disorders. Thus the methods and reagents of the invention are also applicable to these related conditions and disorders.

Conditions related to schizophrenia may include, but are not limited to: schizoaffective disorder, schizotypal personality disorder, schizotypy, a typical psychotic disorders, avoidant personality disorders, bipolar disorder, attention deficit hyperactivity disorder (ADHD), and obsessive compulsive disorder (OCD). Features and diagnostic criteria for these conditions are defined in DSM-III, DSM III-R, DSM-IV, or DSM IV-R. For purposes of description, rather than referring to "schizophrenia and/or related conditions or disorders", the invention will be described in terms of schizophrenia itself. However, it is to be understood that the methods and reagents may also be used in a similar manner with respect to these conditions and disorders as described for schizophrenia itself. Similarly, compounds identified as potential prophylactic or therapeutic agents for schizophrenia may also be utilized for treatment and/or prevention of these related disorders. The following sections provide further description of the various aspects of the invention.

IV. Methods and Reagents for Diagnosis of Schizophrenia or Schizophrenia Susceptibility A. Diagnostic Methods. The invention provides a variety of methods for the diagnosis of schizophrenia or schizophrenia susceptibility. In particular, the invention provides a method for the diagnosis of schizophrenia or schizophrenia susceptibility comprising: (i) providing a sample obtained from a subject to be tested for schizophrenia or schizophrenia susceptibility; and (ii) detecting a polymorphic variant of a polymorphism in a coding or noncoding portion of gene encoding a calcineurin subunit or a calcineurin interacting molecule, or detecting a polymorphic variant of a polymorphism in a genomic region linked to a coding or noncoding portion of a gene encoding a calcineurin subunit or a calcineurin interacting molecule in the sample. It is to be understood that "susceptibility to schizophrenia" does not necessarily mean that the subject will develop schizophrenia but rather that the subject is, in a statistical sense, more likely to develop schizophrenia than an average member of the population. As used herein, "susceptibility to schizophrenia" may exist if the subject has one or more genetic determinants (e.g., polymorphic variants or alleles) that may, either alone or in combination with one or more other genetic determinants, contribute to an increased risk of developing schizophrenia in some or all subjects. Ascertaining whether the subject has any such genetic determinants (i.e., genetic determinants that may increase the risk of developing schizophrenia in the appropriate genetic background) is included in the concept of diagnosing susceptibility to schizophrenia as used herein. Such determination is useful, for example, for purposes of genetic counseling. Thus providing diagnostic information regarding schizophrenia susceptibility includes providing information useful in genetic counseling, and the provision of such information is encompassed by the invention.

The sample itself will typically consist of cells (e.g., blood cells), tissue, etc., removed from the subject. The subject can be an adult, child, fetus, or embryo. According to certain embodiments of the invention the sample is obtained prenatally, either from the fetus or embryo or from the mother (e.g., from fetal or embryonic cells in that enter the maternal circulation). The sample may be further processed before the detecting step. For example, DNA in the cell or tissue sample may be separated from other components of the sample, may be amplified, etc. All samples obtained from a subject, including those subjected to any sort of further processing, are considered to be obtained from the subject.

In general, if the polymorphism is located in a gene, it may be located in a noncoding or coding region of the gene. If located in a coding region the polymorphism may, but frequently will not, result in an amino acid alteration. Such alteration may or may not have an effect on the function or activity of the encoded polypeptide. If the polymorphism is linked to, but not located within, a gene, it is preferred that the polymorphism is closely linked to the gene. For example, it is preferred that the recombination frequency between the polymorphism and the gene is less than approximately 20%, preferably less than approximately 10%, less than approximately 5%, less than approximately 1%, or still less.

According to certain preferred embodiments of any of the inventive methods described above, the gene is coincident with a mapped or identified schizophrenia susceptibility locus. For example, according to various embodiments of the invention the gene may encode any of the molecules listed in Table 1. In a particular embodiment of the invention, discussed further below, the gene encodes the CNAγ subunit. The inventive methods also encompass genes coincident with schizophrenia susceptibility loci that have yet to be mapped or identified. By "coincident with" is meant either that the gene or a portion thereof falls within the identified chromosomal location or is located in close proximity to that location. In general, the resolution of studies identifying genetic susceptibility loci may be on the order of tens of centimorgans. According to certain embodiments of the invention "close proximity" refers to within 20 centimorgans of either side of the susceptibility locus, more preferably within 10 centimorgans of either side of the susceptibility locus, yet more preferably within 5 centimorgans of either side of the susceptibility locus. In general, susceptibility loci are designated by the chromosomal band positions that they span (e.g., 8p21 refers to chromosome 8, arm p, band 21; 8p20-21 refers to chromosome 8, arm p, bands 20-21 inclusive) and may be defined at higher resolution (e.g., 8p21.1). In general, the terms "coincident with" and "close proximity" may be interpreted in light of the knowledge of one of ordinary skill in the art.

Genes that are expressed in the nervous system, e.g., in the brain, may be particularly attractive candidates as schizophrenia susceptibility genes. Such genes may be expressed throughout the brain or in particular regions or cell types or regions in the brain such as cell types or regions (e.g., forebrain, cortex, hippocampus, etc.) implicated in schizophrenia pathogenesis. However, it is possible that genes not currently recognized as expressed in the brain will prove important. For example, such genes may be expressed in only a small subset of brain cells, during particular developmental stages, in particular environmental conditions, etc. Schizophrenia susceptibility genes may also be expressed outside the brain in addition to, or instead of, within the brain.

The invention further provides a method for the diagnosis of schizophrenia or schizophrenia susceptibility comprising: (i) providing a sample obtained from a subject to be tested for schizophrenia or schizophrenia susceptibility; and (ii) detecting an alteration or variation in expression or activity of a calcineurin subunit or a calcineurin interacting molecule in the sample, relative to the expression or activity of the calcineurin subunit or calcineurin interacting molecule that would be expected in a sample obtained from a normal subject. For example, according to various embodiments of the invention the gene may encode any of the molecules listed in Table 1. In a particular embodiment of the invention, discussed further below, the gene encodes the CNAγ subunit.

According to certain embodiments of any of the inventive methods for diagnosis, the methods are applied before the disease or condition manifests clinically. This may be advantageous for early intervention. Appropriate therapy may be administered to a susceptible subject (or to the subject's mother in the case of prenatal diagnosis) prior to development of disease (e.g., prior to birth in the case of prenatal diagnosis). Since schizophrenia may be at least in part a developmental disorder, such early intervention may prove to be critical for prevention of the disease.

The following sections provide further details regarding particular embodiments of the inventive methods and reagents. It is to be understood that there are not intended to be limiting.

B. Methods and Reagents for Identification and Detection of Polymorphisms. In general, polymorphisms of use in the practice of the invention may be initially identified using any of a number of methods well known in the art. For example, numerous polymorphisms are known to exist and are available in public databases, which can be searched as described, for example, in Example 3. Alternately, polymorphisms may be identified by sequencing either genomic DNA or cDNA in the region in which it is desired to find a polymorphism. According to one approach, primers are designed to amplify such a region, and DNA from a subject suffering from schizophrenia is obtained and amplified. The DNA is sequenced, and the sequence (referred to as a "subject sequence") is compared with a reference sequence, which is typically taken to represent the "normal" or "wild type" sequence. Such a sequence may be, for example, the human draft genome sequence, publicly available in various databases mentioned in Example 3, or a sequence deposited in a database such as GENBANK® (NIH genetic sequence database). In general, if sequencing reveals a difference between the sequenced region and the reference sequence, a polymorphism has been identified. Note that this analysis does not necessarily presuppose that either the subject sequence or the reference sequence is the "normal", most common, or wild type sequence. It is the fact that a difference in nucleotide sequence is identified at a particular site that determines that a polymorphism exists at that site. In most instances, particularly in the case of SNPs, only two polymorphic variants will exist at any location. However, in the case of SNPs, up to four variants may exist since there are four naturally occurring nucleotides in DNA. Other polymorphisms such as insertions may have more than four alleles.

Once a polymorphic site is identified, any of a variety of methods may be employed to detect the existence of any particular polymorphic variant in a subject. In general, a subject may have either the reference sequence or an alternate sequence at the site. The phrase "detecting a polymorphism" or "detecting a polymorphic variant" as used herein generally refers to determining which of two or more polymorphic variants exists at a polymorphic site, although "detecting a polymorphism" may also refer to the process of initially determining that a polymorphic site exists in a population. The meaning to be given to these phrases will be clear from the context as interpreted in light of the knowledge of one of ordinary skill in the art. For purposes of description, if a subject has any sequence other than a defined reference sequence (e.g. the sequence present in the human draft genome) at a polymorphic site, the subject may be said to exhibit the polymorphism. In general, for a given polymorphism, any individual will exhibit either one or two possible variants at the polymorphic site (one on each chromosome). (This may, however, not be the case if the individual exhibits one more chromosomal abnormalities such as deletions.)

Detection of a polymorphism or polymorphic variant in a subject (genotyping) may be performed by sequencing, similarly to the manner in which the existence of a polymorphism is initially established as described above. However, once the existence of a polymorphism is established a variety of more efficient methods may be employed. Many such methods are based on the design of oligonucleotide probes or primers that facilitate distinguishing between two or more polymorphic variants.

"Probes" or "primers", as used herein, typically refers to oligonucleotides that hybridize in a base-specific manner to a complementary nucleic acid molecule. Such probes and primers include polypeptide nucleic acids, as described in Nielsen et al, Science, 254, 1497-1500 (1991). The term "primer" in particular generally refers to a single-stranded oligonucleotide that can act as a point of initiation of template-directed DNA synthesis using methods such as PCR (polymerase chain reaction), LCR (ligase chain reaction), etc. Typically, a probe or primer will comprise a region of nucleotide sequence that hybridizes to at least about 8, more often at least about 10 to 15, typically about 20-25, and frequently about 40, 50 or 75, consecutive nucleotides of a nucleic acid molecule. In certain embodiments of the invention, a probe or primer comprises 100 or fewer nucleotides, preferably from 6 to 50 nucleotides, preferably from 12 to 30 nucleotides. In certain embodiments of the invention, the probe or primer is at least 70% identical to the contiguous nucleotide sequence or to the complement of the contiguous nucleotide sequence, preferably at least 80% identical, more preferably at least 90% identical, even more preferably at least 95% identical, or having an even higher degree of identity. In certain embodiments of the invention a preferred probe or primer is capable of selectively hybridizing to a target contiguous nucleotide sequence or to the complement of the contiguous nucleotide sequence. According to certain embodiments of the invention a probe or primer further comprises a label, for example by incorporating a radioisotope, fluorescent compound, enzyme, or enzyme co-factor.

Oligonucleotides that exhibit differential or selective binding to polymorphic sites may readily be designed by one of ordinary skill in the art. For example, an oligonucleotide that is perfectly complementary to a sequence that encompasses a polymorphic site (i.e., a sequence that includes the polymorphic site within it or at one or the other end) will generally hybridize preferentially to a nucleic acid comprising that sequence as opposed to a nucleic acid comprising an alternate polymorphic variant.

In order to detect polymorphisms and/or polymorphic variants, it will frequently be desirable to amplify a portion of DNA encompassing the polymorphic site. Such regions can be amplified and isolated by PCR using oligonucleotide primers designed based on genomic and/or cDNA sequences that flank the site. See e.g., *PCR Primer: A Laboratory Manual*, Dieffenbach, C. W. and Dveksler, G. S. (Eds.); *PCR Basics: From Background to Bench*, Springer Verlag, 2000; M. J. McPherson, et al; Mattila et al., Nucleic Acids Res., 19:4967 (1991); Eckert et al., PCR Methods and Applications, 1:17 (1991); PCR (eds. McPherson et al., IRL Press, Oxford); and U.S. Pat. No. 4,683,202. Other amplification methods that may be employed include the ligase chain reaction (LCR) (Wu and Wallace, Genomics, 4:560 (1989), Landegren et al., Science, 241:1077 (1988), transcription amplification (Kwoh et al., Proc. Natl. Acad. Sci. USA, 86:1173 (1989)), self-sustained sequence replication (Guatelli et al., Proc. Nat. Acad. Sci. USA, 87:1874 (1990)), and nucleic acid based sequence amplification (NASBA). Guidelines for selecting primers for PCR amplification are well known in the art. See, e.g., McPherson, M., et al., *PCR Basics: From Background to Bench*, Springer-Verlag, 2000. A variety of computer programs for designing primers are available, e.g., 'Oligo' (National Biosciences, Inc, Plymouth Minn.), MacVector (Kodak/IBI), and the GCG suite of sequence analysis programs (Genetics Computer Group, Madison, Wis. 53711).

According to certain methods for diagnosing schizophrenia or susceptibility to schizophrenia, hybridization methods, such as Southern analysis, Northern analysis, or in situ hybridizations, can be used (see Current Protocols in Molecular Biology, Ausubel, F. et al., eds., John Wiley & Sons). For example, a sample (e.g., a sample comprising genomic DNA, RNA, or cDNA), is obtained from a subject suspected of being susceptible to or having schizophrenia. The DNA, RNA, or cDNA sample is then examined to determine whether a polymorphic variant in a coding or noncoding portion of a gene encoding a calcineurin subunit or a calcineurin interacting molecule, or a polymorphic variant in a genomic region linked to a coding or noncoding portion of a gene encoding a calcineurin subunit or a calcineurin interacting molecule is present. The presence of the polymorphic variant can be indicated by hybridization of the gene in the genomic DNA, RNA, or cDNA to a nucleic acid probe, e.g., a DNA probe (which includes cDNA and oligonucleotide probes) or an RNA probe. The nucleic acid probe can be designed to specifically or preferentially hybridize with a particular polymorphic variant, e.g., a polymorphic variant indicative of susceptibility to schizophrenia.

In order to diagnose susceptibility to schizophrenia, a hybridization sample is formed by contacting the sample with at least one nucleic acid probe. The probe is typically a nucleic acid probe (which may be labeled, e.g., with a radioactive, fluorescent, or enzymatic label or tag) capable of hybridizing to mRNA, genomic DNA, and/or cDNA sequences encompassing a polymorphic site in a coding or noncoding portion of gene encoding a calcineurin subunit or a calcineurin interacting molecule, or encompassing a polymorphic variant in a genomic region linked to a coding or noncoding portion of a gene encoding a calcineurin subunit or a calcineurin interacting molecule. The nucleic acid probe can be, for example, a full-length nucleic acid molecule, or a portion thereof, such as an oligonucleotide of at least 15, 30, 50, 100, 250 or 500 nucleotides in length and sufficient to specifically hybridize under stringent conditions to appropriate mRNA, cDNA, or genomic DNA.

The hybridization sample is maintained under conditions selected to allow specific hybridization of the nucleic acid probe to a region encompassing the polymorphic site. Specific hybridization can be performed under high stringency conditions or moderate stringency conditions, for example, as described above. In a particularly preferred embodiment, the hybridization conditions for specific hybridization are high stringency. In general, the probe may be perfectly complementary to the region to which it hybridizes, i.e., perfectly complementary to a region encompassing the polymorphic site when the site contains any particular polymorphic sequence. Multiple nucleic acid probes (e.g., multiple probes differing only at the polymorphic site, or multiple probes designed to detect polymorphic variants at multiple polymorphic sites) may be used concurrently in this method. Specific hybridization of any one of the nucleic acid probes is indicative of a polymorphic variant in a coding or noncoding portion of gene encoding a calcineurin subunit or a calcineurin interacting molecule, or is indicative of a polymorphic variant in a genomic region linked to a coding or noncoding portion of a gene encoding a calcineurin subunit or a calcineurin interacting molecule, and is thus diagnostic of susceptibility to schizophrenia.

Northern analysis may be performed using similar nucleic acid probes in order to detect a polymorphic variant of a polymorphism in a coding or noncoding portion of gene encoding a calcineurin subunit or a calcineurin interacting molecule, or detecting a polymorphic variant in a genomic region linked to a coding or noncoding portion of a gene encoding a calcineurin subunit or a calcineurin interacting molecule. See, e.g., Ausubel, *Current Protocols in Molecular Biology*, referenced above.

According to certain embodiments of the invention, a peptide nucleic acid (PNA) probe can be used instead of a nucleic acid probe in the hybridization methods described above. PNA is a DNA mimetic with a peptide-like, inorganic backbone, e.g., N-(2-aminoethyl)glycine units, with an organic base (A, G, C, T or U) attached to the glycine nitrogen via a methylene carbonyl linker (see, for example, Nielsen, P. E. et al., Bioconjugate Chemistry, 1994, 5, American Chemical Society, p. 1 (1994). The PNA probe can be designed to specifically hybridize to a nucleic acid comprising a polymorphic variant conferring susceptibility to or indicative of the presence of schizophrenia.

According to another method, restriction digest analysis can be used to detect the existence of a polymorphic variant of a polymorphism, if alternate polymorphic variants of the polymorphism result in the creation or elimination of a restriction site. A sample containing genomic DNA is obtained from the individual. Polymerase chain reaction (PCR) can be used to amplify a region comprising the polymorphic site, and restriction fragment length polymorphism analysis is conducted (see *Current Protocols in Molecular Biology*, referenced above). The digestion pattern of the relevant DNA fragment indicates the presence or absence of a particular polymorphic variant of the polymorphism and is therefore indicative of the presence or absence of susceptibility to schizophrenia.

Sequence analysis can also be used to detect specific polymorphic variants. A sample comprising DNA or RNA is obtained from the subject. PCR or other appropriate methods can be used to amplify a portion encompassing the polymorphic site, if desired. The sequence is then ascertained, using any standard method, and the presence of a polymorphic variant is determined.

Allele-specific oligonucleotides can also be used to detect the presence of a polymorphic variant, e.g., through the use of dot-blot hybridization of amplified oligonucleotides with allele-specific oligonucleotide (ASO) probes (see, for example, Saiki, R. et al., (1986), Nature (London) 324:163-166). An "allele-specific oligonucleotide" (also referred to herein as an "allele-specific oligonucleotide probe") is typically an oligonucleotide of approximately 10-50 base pairs, preferably approximately 15-30 base pairs, that specifically hybridizes to a nucleic acid region that contains a polymorphism, e.g., a polymorphism associated with a susceptibility to schizophrenia. An allele-specific oligonucleotide probe that is specific for particular a polymorphism can be prepared, using standard methods (see *Current Protocols in Molecular Biology*).

To determine which of multiple polymorphic variants is present in a subject, a sample comprising DNA is obtained from the individual. PCR can be used to amplify a portion encompassing the polymorphic site. DNA containing the amplified portion may be dot-blotted, using standard methods (see *Current Protocols in Molecular Biology*), and the blot contacted with the oligonucleotide probe. The presence of specific hybridization of the probe to the DNA is then detected. Specific hybridization of an allele-specific oligonucleotide probe (specific for a polymorphic variant indicative of susceptibility to schizophrenia) to DNA from the subject is indicative of susceptibility to schizophrenia.

According to another embodiment of the invention, arrays of oligonucleotide probes that are complementary to nucleic acid portions from a subject can be used to identify polymorphisms. Oligonucleotide arrays typically comprise a plurality of different oligonucleotide probes that are coupled to a surface of a substrate in different known locations. These oligonucleotide arrays, also referred to as "Genechips™" are described, for example, in U.S. Pat. No. 5,143,854 and PCT patent publication Nos. WO 90/15070 and 92/10092. Such arrays can generally be produced using mechanical synthesis methods or light directed synthesis methods which incorporate a combination of photolithographic methods and solid phase oligonucleotide synthesis methods. See Fodor et al., Science, 251:767-777 (1991), Pirrung et al., U.S. Pat. No. 5,143,854 (see also PCT Application No. WO 90/15070) and Fodor et al., PCT Publication No. WO 92/10092 and U.S. Pat. No. 5,424,186. Techniques for the synthesis of these arrays using mechanical synthesis methods are described in, e.g., U.S. Pat. No. 5,384,261, the entire teachings of which are incorporated by reference herein.

The array typically includes oligonucleotide probes capable of specifically hybridizing to different polymorphic variants. According to the method, a nucleic acid of interest, e.g., a nucleic acid encompassing a polymorphic site, (which is typically amplified) is hybridized with the array and scanned. Hybridization and scanning are generally carried out according to standard methods. See, e.g., Published PCT Application Nos. WO 92/10092 and WO 95/11995, and U.S. Pat. No. 5,424,186. After hybridization and washing, the array is scanned to determine the position on the array to which the nucleic acid hybridizes. The hybridization data obtained from the scan is typically in the form of fluorescence intensities as a function of location on the array.

Arrays can include multiple detection blocks (i.e., multiple groups of probes designed for detection of particular polymorphisms). Such arrays can be used to analyze multiple different polymorphisms. Detection blocks may be grouped within a single array or in multiple, separate arrays so that varying conditions (e.g., conditions optimized for particular polymorphisms) may be used during the hybridization. For example, it may be desirable to provide for the detection of those polymorphisms that fall within G-C rich stretches of a genomic sequence, separately from those falling in A-T rich segments.

Additional description of use of oligonucleotide arrays for detection of polymorphisms can be found, for example, in U.S. Pat. Nos. 5,858,659 and 5,837,832. In addition, to oligonucleotide arrays, cDNA arrays may be used similarly in certain embodiments of the invention.

Other methods of nucleic acid analysis can be used to detect polymorphisms and/or polymorphic variants. Such methods include, e.g., direct manual sequencing (Church and Gilbert, (1988), Proc. Natl. Acad. Sci. USA 81:1991-1995; Sanger, F. et al. (1977) Proc. Natl. Acad. Sci. 74:5463-5467; Beavis et al. U.S. Pat. No. 5,288,644); automated fluorescent sequencing; single-stranded conformation polymorphism assays (SSCP); clamped denaturing gel electrophoresis (CDGE); denaturing gradient gel electrophoresis (DGGE) (Sheffield, V. C. et al (19891) Proc. Natl. Acad. Sci. USA 86:232-236), mobility shift analysis (Orita, M. et al. (1989) Proc. Natl. Acad. Sci. USA 86:2766-2770), restriction enzyme analysis (Flavell et al. (1978) Cell 15:25; Geever, et al. (1981) Proc. Natl. Acad. Sci. USA 78:5081); heteroduplex analysis; chemical mismatch cleavage (CMC) (Cotton et al. (1985) Proc. Natl. Acad. Sci. USA 85:4397-4401); RNase protection assays (Myers, R. M. et al. (1985) Science 230: 1242); use of polypeptides that recognize nucleotide mismatches, e.g., *E. coli* mutS protein; allele-specific PCR, for example.

In certain embodiments of the invention fluorescence polarization template-directed dye-terminator incorporation (FP-TDI) is used to determine which of multiple polymorphic variants of a polymorphism is present in a subject. This method is based on template-directed primer extension and detection by fluorescence polarization. According to this method, amplified genomic DNA containing a polymorphic site is incubated with oligonucleotide primers (designed to hybridize to the DNA template adjacent to the polymorphic site) in the presence of allele-specific dye-labeled dideoxyribonucleoside triphosphates and a commercially available modified Taq DNA polymerase. The primer is extended by the dye-terminator specific for the allele present on the template, increasing ~10-fold the molecular weight of the fluorophore. At the end of the reaction, the fluorescence polarization of the two dye-terminators in the reaction mixture are analyzed directly without separation or purification. This homogeneous DNA diagnostic method has been shown to be highly sensitive and specific and is suitable for automated genotyping of large number of samples. (Chen, X., et al., *Genome Research*, Vol. 9, Issue 5, 492-498, 1999). Note that rather than involving use of allele-specific probes or primers, this method employs primers that terminate adjacent to a polymorphic site, so that extension of the primer by a single nucleotide results in incorporation of a nucleotide complementary to the polymorphic variant at the polymorphic site.

Real-time pyrophosphate DNA sequencing is yet another approach to detection of polymorphisms and polymorphic variants (Alderborn, A., et al, *Genome Research*, Vol. 10, Issue 8, 1249-1258, 2000). Additional methods include, for example, PCR amplification in combination with denaturing high performance liquid chromatography (dHPLC) (Underhill, P. A., et al., Genome Research, Vol. 7, No. 10, pp. 996-1005, 1997).

In general, it will be of interest to determine the genotype of a subject with respect to both copies of the polymorphic site present in the genome. For example, the complete genotype may be characterized as −/−, as −/+, or as +/+, where a minus sign indicates the presence of the reference or wild type sequence at the polymorphic site, and the plus sign indicates the presence of a polymorphic variant other than the reference sequence. If multiple polymorphic variants exist at a site, this can be appropriately indicated by specifying which ones are present in the subject. Any of the detection means above may be used to determine the genotype of a subject with respect to one or both copies of the polymorphism present in the subject's genome.

According to certain embodiments of the invention it is preferable to employ methods that can detect the presence of multiple polymorphic variants (e.g., polymorphic variants at a plurality of polymorphic sites) in parallel or substantially simultaneously. Oligonucleotide arrays represent one suitable means for doing so. Other methods, including methods in which reactions (e.g., amplification, hybridization) are performed in individual vessels, e.g., within individual wells of a multi-well plate or other vessel may also be performed so as to detect the presence of multiple polymorphic variants (e.g., polymorphic variants at a plurality of polymorphic sites) in parallel or substantially simultaneously according to certain embodiments of the invention.

The invention provides a database comprising a list of polymorphic sequences stored on a computer-readable medium, wherein the polymorphic sequences occur in a coding or noncoding portion of a gene encoding a calcineurin subunit or encoding a calcineurin interacting molecule, or in a genomic region linked to such a gene, and wherein the list is largely or entirely limited to polymorphisms have been identified as useful in performing genetic diagnosis of schizophrenia or susceptibility to schizophrenia, or for performing genetic studies of schizophrenia or susceptibility to schizophrenia.

C. Primers, Probes, Oligonucleotide Arrays, and Kits

The invention provides oligonucleotide probes and primers that can detect polymorphic variants of polymorphisms in a coding or noncoding portion of gene encoding a calcineurin subunit or a calcineurin interacting molecule, or polymorphic variants of a polymorphism in a genomic region linked to a coding or noncoding portion of a gene encoding a calcineurin subunit or a calcineurin interacting molecule. According to certain embodiments of the invention the presence of a particular polymorphic variant at the polymorphic site is indicative of susceptibility to or diagnostic of schizophrenia. The genes include, but are not limited to, primers that can detect polymorphisms in any of the genes described herein (Table 1). In particular, the invention provides oligonucleotide probes and primers that are able to detect polymorphic variants of the CC-5, CC-21, CC33, and CC-S3 polymorphisms in the gene encoding the CNAγ subunit, as defined in Table 3.

According to certain embodiments of the invention the allele specific primers and/or probes preferably correspond exactly with the allele to be detected (i.e., they are identical in sequence or perfectly complementary to a portion of DNA that encompasses the polymorphic site, wherein the site contains any of the possible variants), but derivatives thereof are also provided wherein, for example, about 6-8 of the nucleotides at the 3', terminus correspond with (i.e., are identical in sequence or perfectly complementary to) the allele to be detected and wherein up to 10, such as up to 8, 6, 4, 2 or 1 of the remaining nucleotides may be varied without significantly affecting the properties of the primer or probe.

The invention further provides a set of oligonucleotide primers, wherein the primers terminate adjacent to a polymorphic site in a coding or noncoding portion of gene encoding a calcineurin subunit or a calcineurin interacting molecule, or wherein the primers terminate adjacent to a polymorphic site in a genomic region linked to a coding or noncoding portion of a gene encoding a calcineurin subunit or a calcineurin interacting molecule. Such primers are useful, for example, in performing fluorescence polarization template-directed dye-terminator incorporation, as described above. In particular, the invention provides oligonucleotide primers that terminate immediately adjacent to the CC-21, CC33, and CC-S3 polymorphic site in the gene encoding the CNAγ subunit, as defined in Table 3, and primers that terminate immediately adjacent to the CC-5 polymorphic site in the gene encoding the CNAγ subunit, as defined in Table 2. These primers may be used, for example, to detect presence of the CC-21, CC-33, CC-S3; G, C, A schizophrenia risk haplotype, and to detect presence of the CC-5 polymorphism and polymorphic variants including, but not limited to, variants having A at the polymorphic site.

The invention provides, for each of the CC-21, CC-33, CC-S3, and CC-5 polymorphisms, a primer that terminates at the nucleotide position immediately adjacent to a polymorphic site on the 3' side and extends at least 8 and less than 100 nucleotides in the 5' direction from this site. It is noted that the foregoing includes two classes of primers, having sequences representing both DNA strands. According to certain embodiments of the invention the primer extends at least 10, at least 12, at least 15, or at least 20 nucleotides in the 5' direction. According to certain embodiments of the invention the primer extends less than 80, less than 60, less than 50, less than 40, less than 30, or less than 30 nucleotides in the 5' direction. The invention further provides primers that terminate and extend similarly for any polymorphic site in a gene encoding a calcineurin subunit or calcineurin interacting molecule, or a polymorphic site in a genomic region linked to such a gene, wherein a polymorphic variant of a polymorphism located at the polymorphic site confers susceptibility to schizophrenia or is indicative of the presence of schizophrenia.

In general, primers and probes may be made using any convenient method of synthesis. Examples of such methods may be found in standard textbooks, for example "Protocols for Oligonucleotides and Analogues; Synthesis and Properties," Methods in Molecular Biology Series; Volume 20; Ed. Sudhir Agrawal, Humana ISBN: 0-89603-247-7; 1993. According to certain embodiments of the invention the primer(s) and/or probes are labeled to facilitate detection.

The primers and probes of the invention may be conveniently provided in sets, e.g., sets capable of determining which polymorphic variant(s) is/are present among some or all of the possible polymorphic variants that may exist at a particular polymorphic site. The sets may include allele-specific primers or probes and/or primers that terminate immediately adjacent to a polymorphic site. Multiple sets of primers and/or probes, capable of detecting polymorphic variants at a plurality of polymorphic sites may be provided.

The primers or probes may be provided in the form of a kit for diagnostic and/or research purposes, which may further comprise any of a variety of other components including, but not limited to, appropriate packaging and instructions for use in the methods of the invention, appropriate buffer(s), nucleotides, and/or polymerase(s) such as thermostable polymerases, for example Taq polymerase, other enzymes, positive and negative control samples, negative control primers and/or probes, etc.

The invention further provides oligonucleotide arrays comprising one or more of the inventive probes described above. In particular, the invention provides an oligonucleotide array comprising oligonucleotide probes that are able to detect polymorphic variants of the CC-5, CC-21, CC-33, and CC-S3 polymorphisms (e.g., the CC-21, CC-33, CC-S3; G, C, A schizophrenia risk haplotype) in the gene encoding the CNAγ subunit, as defined in Tables 2 and 3. Such arrays may be provided in the form of kits for diagnostic and/or research purposes. Kits may include any of the components mentioned above, in addition to further components specific for hybridization and processing of oligonucleotide arrays. Appropriate software (i.e., computer-readable instructions stored on a computer-readable medium) for analyzing the results obtained by scanning the arrays may be provided by the invention. Such software may, for example, provide the user with an indication of the genotype of a sample and/or provide an assessment of the degree of susceptibility of the subject to schizophrenia, or an assessment of the likelihood that the subject suffers from schizophrenia.

According to certain embodiments of the invention the kits are manufactured in accordance with good manufacturing practices as required for FDA-approved diagnostic kits.

D. Detection of Alterations in mRNA. According to certain embodiments of the invention alterations or variations in mRNA expression are detected in order to determine whether a subject is susceptible to or suffers from schizophrenia. The expression level (i.e., abundance), expression pattern (e.g., temporal or spatial expression pattern, which includes subcellular localization, cell type specificity), etc., of mRNA encoding a calcineurin subunit or a calcineurin interacting molecule in a sample obtained from a subject is determined and compared with the expression level or expression pattern that would be expected in a sample obtained from a normal subject. mRNA size, processing (e.g., presence of splicing variants, polyadenylation, etc.) may also be compared. According to certain embodiments of the invention the calcineurin subunit or calcineurin interacting molecule is one that is encoded by a gene within or linked to a schizophrenia susceptibility locus, or within which a functional mutation causing or contributing to susceptibility or development of schizophrenia may exist.

In general, such detection and/or comparison may be performed using any of a number of suitable methods known in the art including, but not limited to, Northern blotting, cDNA or oligonucleotide array hybridization, in situ hybridization, RNase protection, PCR (e.g., RT-PCR, quantitative PCR) etc. Historical data (e.g., the known expression level, pattern, or size in the normal population) may be used for purposes of the comparison rather than performing the detection method on a control sample.

The invention provides cDNA probes and PCR primers useful for performing the analyses described above, e.g., cDNA probes and PCR primers that specifically hybridize to one or more polymorphic variants. Such probes and/or primers may encompass a polymorphic site and may be perfectly complementary to or identical in sequence to a region encompassing the site, in any of its possible variants. According to certain embodiments of the invention the probes and/or primers are exon-specific, e.g., they hybridize selectively or specifically to variants that either contain or lack a particular exon. Kits for diagnostic and/or research purposes containing, for example, cDNA probes and/or primers as described above, in addition to other components such as those mentioned above, are also provided by the invention.

E. Detection of Alterations in Protein. According to certain embodiments of the invention alterations or variations in protein expression and/or activity are detected in order to determine whether a subject is susceptible to or suffers from schizophrenia. The expression level (i.e., abundance), expression pattern (e.g., temporal or spatial expression pattern, which includes subcellular localization, cell type specificity), size, association with other cellular constituents (e.g., in a complex such as a CN complex), etc., of a calcineurin subunit or a calcineurin interacting molecule in a sample obtained from a subject is determined and compared with the expression level or expression pattern that would be expected in a sample obtained from a normal subject. According to certain embodiments of the invention the calcineurin subunit or calcineurin interacting molecule is one that is encoded by a gene within or linked to a schizophrenia susceptibility locus, or within which a functional mutation causing or contributing to susceptibility or development of schizophrenia may exist.

In general, such detection and/or comparison may be performed using any of a number of suitable methods known in the art including, but not limited to, immunoblotting (Western blotting), immunohistochemistry, ELISA, radioimmunoassay, protein chips (e.g., comprising antibodies to the relevant proteins), etc. Historical data (e.g., the known expression level, activity, expression pattern, or size in the normal population) may be used for purposes of the comparison.

The present invention provides an antibody able to specifically bind to a calcineurin subunit or calcineurin interacting molecule, wherein the subunit or molecule is encoded by a gene within or linked to a schizophrenia susceptibility locus, or within which a functional mutation causing or contributing to susceptibility or development of schizophrenia may exist. In particular, the invention provides an antibody able to specifically bind to a variant of such a calcineurin subunit or calcineurin interacting molecule, wherein the presence of the variant in a subject is indicative of susceptibility to or presence of schizophrenia. Such antibodies are able to distinguish between calcineurin subunits or calcineurin interacting molecules that differ at sites encoded by polymorphic variants.

Generally applicable methods for producing antibodies are well known in the art and are described extensively in references cited above, e.g., *Current Protocols in Immunology and Using Antibodies: A Laboratory Manual*. It is noted that antibodies can be generated by immunizing animals (or humans) either with a full length polypeptide, a partial polypeptide, fusion protein, or peptide (which may be conjugated with another moiety to enhance immunogenicity). The specificity of the antibody will vary depending upon the particular preparation used to immunize the animal and on whether the antibody is polyclonal or monoclonal. For example, if a peptide is used the resulting antibody will bind only to the antigenic determinant represented by that peptide. It may be desirable to develop and/or select antibodies that specifically bind to particular regions of the polypeptide, e.g., the extracellular domain. Such specificity may be achieved by immunizing the animal with peptides or polypeptide fragments that correspond to that region. Alternately, a panel of monoclonal antibodies can be screened to identify those that specifically bind to the desired region. As mentioned above, according to certain embodiments of the invention the antibodies specifically bind to antigenic determinants that comprise a region encoded by a polymorphic site. According to certain embodiments of the invention such antibodies are able to distinguish between molecules that differ by a single amino acid. In particular, the invention provides antibodies capable of specifically binding to CNAγ, or a portion thereof, including amino acid 163, wherein amino acid 163 is either glutamine or arginine. Any of the antibodies described herein may be labeled.

The invention provides any of the foregoing antibodies in panels, e.g., panels of antibodies able to specifically bind to multiple variants of any particular calcineurin subunit or calcineurin interacting molecule, and panels of antibodies able to specifically bind to multiple variants of a plurality of calcineurin subunits or calcineurin interacting molecules. The antibodies may be provided in kits, with additional components as mentioned above, including substrates for an enzymatic reaction. The antibodies may be used for research, diagnostic, and/or therapeutic purposes.

In general, preferred antibodies will possess high affinity, e.g., a $K_d$ of <200 nM, and preferably, of <100 nM for their target. According to certain embodiments of the invention preferred antibodies do not show significant reactivity with normal tissues, e.g., tissues of key importance such as heart, kidney, brain, liver, bone marrow, colon, breast, prostate, thyroid, gall bladder, lung, adrenals, muscle, nerve fibers, pancreas, skin, etc. Antibodies with low reactivity towards heart, kidney, central and peripheral nervous system tissues and liver are particularly preferred. In the context of reactivity with tissues, the term "significant reactivity", as used herein, refers to an antibody or antibody fragment, which, when applied to a tissue of interest under conditions suitable for immunohistochemistry, will elicit either no staining or negligible staining, e.g., only a few positive cells scattered among a field of mostly negative cells.

According to certain embodiments of the invention the functional activity of a calcineurin subunit or calcineurin interacting molecule in sample obtained from a subject is detected and/or measured and is compared with the activity of the calcineurin subunit or interacting molecule that would be expected in a sample obtained from a normal subject. According to certain embodiments of the invention the calcineurin subunit or calcineurin interacting molecule is one that is encoded by a gene within or linked to a schizophrenia susceptibility locus, or within which a functional mutation causing or contributing to susceptibility or development of schizophrenia may exist. It will be appreciated that the particular assay to be employed in detecting and/or measuring the functional activity will depend on the particular molecule being assayed. For example, if the molecule is a phosphatase (e.g., CN), the appropriate assay will be a phosphatase assay using a substrate of the phosphatase. A number of CN substrates are known in the art (e.g., DARPP-32, dynamin, etc.) The activity may be ability to activate or repress transcription, which may be measured using an appropriate reporter construct. The activity may be ability to bind to another molecule and/or to inhibit the activity of that other molecule, etc.

V. Methods and Reagents for Screening for Compounds Useful in Treating Schizophrenia or Schizophrenia Susceptibility The invention provides a number of methods and reagents that may be used to screen for compounds useful in treatment of schizophrenia or schizophrenia susceptibilty. It is noted that any of the inventive reagents, methods, and compounds identified according to these methods are not limited to uses related to treatment of schizophrenia or susceptibility to schizophrenia but may be employed for a variety of other purposes. It is also noted that the screens described below are divided into categories for convenience and ease of understanding only, and the classification is not intended to limit the applications of the compounds in any way or place any limitations on their mechanism(s) of action.

A. Screens for Compounds that Modulate (Enhance or Reduce) Calcineurin Activity.

1. NF-AT transcription assay. According to one of the inventive methods, DNA transfection, electroporation, etc., is used to express calcineurin subunits and NF-AT, and to introduce an NF-AT reporter construct (e.g., NFAT-luciferase or any other appropriate NF-AT reporter, e.g., a construct comprising a nucleic acid encoding a detectable marker operably linked to an NF-AT responsive regulatory element such as a promoter), into a cell line that is a suitable host for calcineurin function. Alternatively, a cell line that expresses one or more calcineurin or NFAT components of this pathway can be used as a host, and any components not expressed endogenously provided, e.g., by DNA transfection. In general, many commonly available cell lines are suitable hosts. According to certain embodiments of the invention it may be preferable to avoid use of a cell line that expresses one or more endogenous inhibitors of CN, such as Cabin1 or CHP. According to certain embodiments of the invention a cell line exhibiting features similar to those in which the therapeutic effect is expected to occur may be used, e.g., a neural or glial cell line.

The cell line expressing all desired components may be treated with calcium ionophore plus PMA to stimulate calcineurin activity which may be measured by assessing activity of the NF-AT reporter construct (e.g., NFAT-luciferase) [22-24]. Comparison of reporter activity in absence or presence of compounds (e.g., a member of a combinatorial library, natural product collection, etc., is used to identify compounds that yield altered (e.g., increased or decreased) NFAT-mediated transcription. Among these compounds will be those that increase or decrease NFAT activity directly, or indirectly either through calcineurin or other interactions. To confirm calcineurin specificity, the same assay can be performed with all members of the pathway present except specific calcineurin subunits, or in presence of constitutively active forms of NF-AT 45 kD subunit. This may entail using cell lines deficient for specific calcineurin subunits, or inactivating specific subunits by RNAi during the assay. The inventive screen may also be performed in the presence of siRNA targeted to one or more transcripts encoding one or more specific calcineurin catalytic subunits, e.g., to screen for compounds that specifically target a single expressed calcineurin catalytic subunit.

Thus the invention provides a method for identifying a candidate compound for treatment of schizophrenia or susceptibility to schizophrenia comprising steps of: (i) providing a biological system containing NF-AT, calcineurin, and an NF-AT reporter; (ii) contacting the biological system with a compound; (iii) comparing the transcriptional response of the reporter in the presence of the compound with the response or expected response in the absence of the compound. If the transcriptional response in the presence of the compound is different from (e.g., greater or less than) the transcriptional response that occurs or would be expected in the absence of the compound, the compound is identified as a modulator of calcineurin activity and a candidate compound for treatment of schizophrenia or susceptibility to schizophrenia. By "biological system" is meant any vessel, well, or container in which biomolecules (e.g., nucleic acids, polypeptides, polysaccharides, lipids, etc.) are placed; a cell or population of cells; a tissue; an organism, etc. Typically the biological system is a cell or population of cells, but the method can also be performed in a vessel using purified or recombinant proteins.

This assay can also be used in combination with transfection or addition of calcineurin inhibitory proteins such as Cabin 1 or CHP to screen for compounds that activate calcineurin by interfering with binding between calcineurin and inhibitory proteins. Again specificity could be determined by repeating the assay in absence of inhibitor protein gene transfection or by using RNAi to inhibit expression of the inhibitory protein.

According to certain embodiments of the invention the screen is performed in the presence of siRNA targeted to CNAα and/or CNAβ to specifically screen for compounds that target CNAγ-dependent calcineurin activity. According to other embodiments of the invention the screen is performed in cell lines that are deficient for CNAα or CNAβ to specifically screen for compounds that target CNAγ-dependent calcineurin activity. Identified compounds may then be tested in similar assays in which CNAα and/or CNAβ is/are present and CNAγ activity is absent to test for the CNAγ specificity of the compounds.

The above assays will also likely yield non-calcineurin directed compounds that enhance NF-AT activity. These compounds may also comprise useful therapy for schizophrenia as they may mimic enhanced CN activity. Such compounds, and any compounds that do not affect CN activity solely by directly binding to the CNB subunit (or other CN subunits), may be tested in the CNB knockout mice (or in mice lacking other CN subunits) to determine if they suppress the behavioral effects of absence of CNB, as an assay for effectiveness. See methods to screen for effectiveness of non-CN-binding candidate compounds by treating CN mutant mice.

The above screening methods will also yield compounds that decrease or inhibit NF-AT activity or could be readily modified to do so, e.g., by employing a reporter that exhibits a high degree of basal NF-AT activity, and screening for reduction in activity.

2. Screen for molecules that block binding of calcineurin binding proteins. Standard yeast 2 and/or 3 hybrid assays can be used to screen for molecules that block binding of calcineurin binding proteins such as Cabin1, CHP, CS1, etc., to calcineurin complexes and/or subunits.

3. Screen for activators or inhibitors of CN phosphatase activity. The invention provides methods for identifying activators and inhibitors of CN phosphatase activity, e.g., using substrate dephosphorylation assays. According to certain embodiments of the invention a phosphorylated CN substrate is provided and is incubated in vitro with CN (and, optionally with one or more CN interacting proteins) in vitro in the presence or absence of a candidate compound. The extent or rate of dephosphorylation of the substrate is measured and compared with the extent or rate of dephosphorylation in cells not exposed to the compound. An increase in the extent or rate of dephosphorylation in cells exposed to the compound is indicative that the compound is an activator of CN phosphatase activity, and a decrease in extent or rate of phosphorylation in cells exposed to the compound is indicative that the compound is an inhibitor of CN phosphatase activity. The mechanism of such inhibition or activation is likely to be direct in the sense that it involves a physical interaction between CN and/or the substrate since other cellular components are absent. Components for the above assay (e.g., CN, CN interacting proteins) may be isolated and/or purified from cells and/or produced in vitro using recombinant DNA technology. Alternately, cell extracts containing the components may be used as a source of CN and/or CN interacting proteins. Such cells may express one or more of the components endogenously or may be transfected/electroporated, etc., with one or more constructs encoding one or more CN subunits and/or CN interacting proteins.

Thus the invention provides a method of identifying a candidate compound for treatment of schizophrenia or susceptibility to schizophrenia comprising steps of: (i) providing a biological system comprising phosphorylated calcineurin substrate and calcineurin; (ii) contacting the biological system with a compound; (iii) comparing the extent or rate of dephosphorylation of the substrate with the extent or rate of dephosphorylation occurring or expected to occur in the absence of the compound. If the extent or rate of dephosphorylation of the substrate in the presence of the compound is different from (e.g., greater or less than) the extent or rate of dephosphorylation of the substrate that occurs or would be expected in the absence of the compound, the compound is identified as a modulator of calcineurin activity and a candidate compound for treatment of schizophrenia or susceptibility to schizophrenia.

Any CN substrate may be used in these assays. Typically the substrate will be labeled for ease of detection. For example, 33-P labeled 19-residue phosphopeptide (RII phosphopeptide), phosphorylated DARPP-32, or phosphorylated inhibitor 1 or phosphorylated fragments of these proteins (or other CN substrates such as dynamin) may be used as substrates for the dephosphorylation assay. The label may or may not be radioactive. If radioactive label (e.g., 32-P) is used, phosphorylation state of the substrate may be assessed using standard techniques for detecting radiolabel.

According to certain embodiments of the invention phosphorylation-state specific antibodies are used to detect the extent or rate of dephosphorylation of a substrate. Phosphorylation state-specific monoclonal antibodies against DARPP-32/inhibitor 1 are known in the art [26, 27]. Antibodies that specifically bind to non-phosphorylated DARPP-32/inhibitor 1 may readily be generated using similar methods, as may phosphorylation state-specific monoclonal antibodies that specifically bind to phosphorylated or dephosphorylated forms of other CN substrates.

According to certain embodiments of the invention, in order to make the assay specific for particular calcineurin subunits recombinant forms of all human calcineurin forms, i.e. recombinant human CNAγ, recombinant human CNAα and recombinant human CNAβ may be generated. This may be accomplished as described, for example, in Mondragon, A., et al., *Biochemistry* (1997), 36(16):4934-42). The assay may be performed using recombinant human CNAγ to screen for compounds that modulate its activity. Identified compounds can then be tested in the same assay using recombinant human CNAα or CNAβ to determine the subunit specificity of the compounds, i.e. to identify compounds that are specific for CNAγ. Compounds that modulate (i.e. enhance or suppress CNAγ-dependent calcineurin activity can be identified by this screen.

Similar cell-based assays can be performed, in which cells expressing CN (and optionally any CN interacting protein(s)) and a CN substrate are exposed to a candidate compound. Such cells may endogenously express CN and/or the CN interacting molecules and CN substrate or may be transfected/electroporated with one or more constructs encoding any of these components. Preferably the cells also express (or are engineered to express) upstream components necessary for or contributing to phosphorylation of the CN substrate.

The CN substrate is isolated from the cell and the extent or rate of dephosphorylation (or phosphorylation) is measured and compared with the degree of dephosphorylation (or phosphorylation) in cells not exposed to the compound. An increase in the extent or rate of dephosphorylation (or phosphorylation) in cells exposed to the compound is indicative that the compound is an activator (or inhibitor) of CN phosphatase activity, and a decrease in extent or rate of dephosphorylation (or phosphorylation) in cells exposed to the compound is indicative that the compound is an inhibitor (or activator) of CN phosphatase activity. The mechanism of such inhibition or activation may be direct or indirect.

According to certain embodiments of the invention, specificity of the screen is achieved by performing the screen in the absence of CNAα and CNAβ as described above. Subunit specificity of the screen can then be assessed by performing the screen in presence of CNAα or CNAβ and absence of CNAγ. Compounds that modulate (i.e. enhance or suppress) CNAγ-dependent calcineurin activity are identified by this screen.

Whether the cell-based screens measure dephosphorylation or phosphorylation may depend on the extent to which the substrate is normally phosphorylated in the cell. According to certain embodiments of the invention the cell is treated with a compound that results in increased phosphorylation of the CN substrate prior to performing the assay. For example, cells may be treated with an appropriate agonist, e.g., dopamine, to put DARPP-32/inhibitor 1 in a phosphorylated state. The calcineurin pathway may be activated at a sub-saturating level with PMA and ionomycin in the presence and absence of candidate compounds. Immunohistochemical and/or in vitro immunodetection methods such as ELISA assays (using, for example, the phosphorylation state specific antibodies described above) may be used to detect the extent or rate of dephosphorylation/phosphorylation of the substrate. According to certain embodiments of the invention quantitative methods for detecting the extent or rate of dephosphorylation (e.g., ELISA) are employed.

According to certain embodiments of the inventive methods described above, if the extent and/or rate of dephosphorylation of a CN substrate is increased or decreased in the presence of the compound relative to the extent or rate of dephosphorylation in the absence of the compound, the compound is identified as a potential therapeutic agent for treatment of schizophrenia or schizophrenia susceptibility. According to certain embodiments of the inventive methods, if the extent and/or rate of phosphorylation of a CN substrate is increased or decreased in the presence of the compound relative to the extent or rate of phosphorylation in the absence of the compound, the compound is identified as a potential therapeutic agent for treatment of schizophrenia or schizophrenia susceptibility.

According to certain embodiments of any of the above methods, the assay is performed in the presence of a known inhibitor of CN (of which several classes exist including endogenous inhibitors such as Cabin1, CHP, DSCR1, DSCR2, ZAK14; immunosuppressant drugs such as cyclosporin A and FK506; pyrethroid insecticides such as cypermethrin and deltamethrin, etc.) in order to confirm the specificity of any compound that appears to activate or inhibit CN.

B. Screen for Compounds that Target Ryanodine Receptor Type 3 Including Ligands.

The invention provides a variety of methods to identify compounds that modulate the activity of the ryanodine receptor type 3 as candidate compounds for treatment of schizophrenia or schizophrenia susceptibility. One such method comprises identification of compounds that modulate the binding of labeled ryanodine to the ryanodine receptor type 3. According to this method endoplasmic reticulum (ER) membranes from cells expressing the ryanodine receptor type 3 are isolated and incubated in the presence of labeled ryanodine (e.g., [3H]-ryanodine or any other form of labeled ryanodine can be used). Cells can be pretreated with candidate compound prior to isolation of the membranes, or compounds can be added to the isolated membrane preparation prior to, following, or during exposure to a candidate compound.

Compounds that alter the binding of the labeled ryanodine to the membrane preparation are identified. This assay has been employed to assess the effect of suramin and suramin analogs on binding of [3H] ryanodine to a ryanodine receptor [28]. In that case, suramin was shown to increase binding of [3H]-ryanodine to membranes and to increase the probability of the channel being open (e.g., increase calcium influx). Therefore, screens based on this principle will enable identification of compounds that modulate the activity of the ryanodine receptor type 3. Among those compounds identified will be ryanodine receptor ligands that compete with labeled ryanodine for binding to the receptor.

According to certain embodiments of the invention compounds so identified are then screened for their effects on intracellular calcium release, using, for example, calcium sensitive indicators of which a number are well known in the art. Specificity can be assessed by examining the effects of compounds on calcium release in cells that do not express the ryanodine receptor type 3, or in combination with siRNA targeted to transcripts encoding ryanodine receptor type 3. If the compound is specific its effects in such cells should be substantially less than in cells expressing ryanodine receptor type 3. Other methods for detecting compounds that alter binding of ryanodine to the membrane preparation, not employing labeled ryanodine, are also within the scope of the invention. Compounds that alter the binding of the labeled ryanodine to the membrane preparation are candidate agents for treatment of schizophrenia or schizophrenia susceptibility. The compounds may also be used for any purpose for which it is desired to modulate the activity of the ryanodine receptor type 3.

Thus the invention provides a method of identifying a candidate compound for treatment of schizophrenia or susceptibility to schizophrenia comprising steps of: (i) providing a biological system comprising a cellular membrane comprising ryanodine receptor type 3; (ii) contacting the biological system with a compound; (iii) contacting the cellular membrane with ryanodine; (iv) comparing the extent or rate of binding of ryanodine to the cellular membrane in the presence of the compound with the extent or rate of binding that occurs or would be expected in the absence of the compound; and (v) identifying the compound as a candidate compound for treatment of schizophrenia or susceptibility to schizophrenia if the extent or rate of binding in the presence of the compound is different from that occurring or expected to occur in the absence of the compound. According to certain embodiments of the invention the ryanodine is labeled. According to certain embodiments of the invention the membranes are ER membranes.

C. Screen for Compounds that Target IP3 Receptor Type 1 (ITPR1) Including Ligands. The invention provides a variety of methods to identify compounds that modulate the activity of the IP3 receptor type 1 as candidate compounds for treatment of schizophrenia or schizophrenia susceptibility. One such method comprises identification of compounds that modulate the binding of labeled inositol 1,4,5-triphosphate (IP3) to the IPTR1 receptor. According to this method endoplasmic reticulum (ER) membranes from cells expressing the IPTR1 receptor are isolated and incubated in the presence of labeled IP3 (e.g., [3H]-IP3 or any other form of labeled IP3 can be used). Cells can be pretreated with candidate compound prior to isolation of the membranes, or compounds can be added to the isolated membrane preparation prior to, following, or during exposure to a candidate compound.

Compounds that alter the binding of the labeled IP3 to the membrane preparation are identified. This assay has been employed to assess the effect of cyclosporin A [29] or chloroquine [30] on binding of [3H]-IP3 to IP3 receptors on cell membranes. In those studies, cyclosporin A or chloroquine was shown to decrease binding of [3H]-IP3 to membranes and to decrease calcium influx. Therefore, screens based on this principle will identify compounds that modulate the activity of the IP3 receptor type 1. Among those compounds identified will be ligands that compete with labeled IP3 for binding to the receptor. Compounds identified can then be screened for their effects on intracellular calcium release, using calcium sensitive indicators.

Specificity can be assessed by examining the effects of compounds on calcium release in cells that do not express the IP3 receptor type 1, or in combination with siRNA targeted to transcripts encoding IP3 receptor type 1. If the compound is specific its effects in such cells should be substantially less than in cells expressing IP3 receptor type 1. Other methods for detecting compounds that alter binding of IP3 to the membrane preparation, not employing labeled IP3, are also within the scope of the invention. Compounds that alter the binding of the labeled IP3 to the membrane preparation are candidate agents for treatment of schizophrenia or schizophrenia susceptibility. The compounds may also be used for any purpose for which it is desired to modulate the activity of the IP3 receptor type 1. It is noted that the ryanodine receptor type 3 and the IP3 receptor type 1 form a complex, and compounds that affect the formation of this complex, e.g., by inhibiting or activating formation of the complex, are included within the scope of the invention.

Thus the invention provides a method of identifying a candidate compound for treatment of schizophrenia or susceptibility to schizophrenia comprising steps of: (i) providing a biological system comprising a cellular membrane comprising IP3 receptor type 1; (ii) contacting the biological system with a compound; (iii) contacting the cellular membrane with IP3; (iv) comparing the extent or rate of binding of IP3 to the cellular membrane in the presence of the compound with the extent or rate of binding that occurs or would be expected in the absence of the compound; and (v) identifying the compound as a candidate compound for treatment of schizophrenia or susceptibility to schizophrenia if the extent or rate of binding in the presence of the compound is different from that occurring or expected to occur in the absence of the compound. According to certain embodiments of the invention the IP3 is labeled. According to certain embodiments of the invention the membranes are ER membranes.

D. Screens for Compounds that Modulate PP1 Activity. The invention provides a number of screens for compounds that modulate (e.g., increase or decrease) the activity of protein phosphatase I (PPI), a widely expressed serine/threonine phosphatase. PP1 is indirectly activated by the dephosphorylation dependent inactivation of various inhibitors (e.g., inhibitor 1) by calcineurin. Phosphorylated inhibitor 1 is one of a number of inhibitors of PP1 (Watanabe, T., et al., Proc Natl Acad Sci USA Mar. 13, 2001; 98(6):3080-5. While not wishing to be bound by any theory, the inventors propose that enhanced calcineurin activity should increase the inactivation of inhibitor 1 and cause increased PP1 activation. Conversely, decreased calcineurin activity may decrease the inactivation of inhibitor 1 and cause decreased PP1 activation, resulting in increased PP1 activity.

Among substrates of PP1 are elements of signal transducing pathways such as the MAP kinase/c-Fos promoter [28], components of the cAMP/CREB pathway [29], and components of the retinoic acid receptor pathway [30]. One final readout of these pathways is a transcriptional response that can be measured using specific reporter constructs. The invention provides a method for identifying a candidate therapeutic compound that modulates PPI activity comprising steps of: (i) providing a biological system comprising a transcriptional reporter construct, wherein the construct comprises a PP1-responsive regulatory element; (ii) contacting the biological system with the compound; and (iii) comparing the transcriptional response of the construct in the presence of the compound with the response or expected response in the absence of the compound. If the transcriptional response in the presence of the compound is different from (e.g., greater or less than) the transcriptional response that occurs or would be expected in the absence of the compound, the compound is identified as a modulator of PP1 activity. Note that whether the compound is identified as an activator or inhibitor of PP1 activity will depend, in general, on whether the effect of PP1 activity on the particular PP1-responsive regulatory element or elements selected for use in the construct is activating or inhibiting. Both varieties of PP1-responsive regulatory elements are within the scope of the invention. A compound that modulates PP1 activity is identified as a candidate compound for the treatment of schizophrenia or schizophrenia susceptibility.

The invention further provides similar reporter-based assays that may be used to identify compounds that block inhibition of PP1 by DARPP-32 or inhibitor 2. This assay will also identify compounds that alter (e.g. enhance) PP1 activity by other mechanisms. Such compounds are also candidate compounds for treatment of schizophrenia or susceptibility to schizophrenia.

E. Screen for Compounds that Modulate LTD. According to another inventive method, compounds including neuropeptides, neurotransmitter receptor agonists and antagonists, and ion channel antagonists (e.g., ion channel blockers) and agonists, and compounds that interact with components of major neuronal signal transduction cascades including kinases and phosphatases are screened for the ability to modulate (reduce or enhance) LTD. According to one approach, the ability to modulate LTD in hippocampal slices. Numerous such compounds are known, and one of ordinary skill in the art will generally be able to identify many such compounds by a review of the scientific literature. Methods for measurement of LTD are also known in the art.

The screen can be performed with slices from normal and CN-deficient mice (e.g., CNB deficient mice) to determine if the effects are dependent on calcineurin signaling. Compounds that modulate LTD can be tested in mouse models of schizophrenia for efficacy. Thus the invention provides a method of identifying a candidate compound for treatment of schizophrenia or susceptibility to schizophrenia comprising steps of: (i) providing a biological system suitable for measuring LTD; (ii) contacting the biological system with the candidate compound; (iii) measuring LTD in the biological system; and (iv) identifying the compound as a candidate compound for treatment of schizophrenia or susceptibility to schizophrenia if the extent of LTD in the biological system differs from the extent of LTD that occurs or would be expected to occur in the absence of the compound. According to certain embodiments of the invention the biological system is a hippocampal slice.

The molecular targets of compounds that modulate LTD are candidate drug targets for schizophrenia and related diseases, and once identified, the invention includes screens for small molecules that bind to these targets as candidate compounds for treatment of schizophrenia or susceptibility to schizophrenia.

F. Screen for Compounds that Modulate Intracellular Calcium Levels. The invention provides a number of screens for compounds that modulate (e.g., increase or decrease) intracellular calcium levels. According to one approach, calcium sensitive molecules (e.g., calcium sensitive dyes, of which a number are known in the art) are use to monitor intracellular calcium concentration. Compounds are applied to cells loaded with calcium sensitive molecules or expressing engineered calcium sensor proteins, and effects on intracellular calcium levels are assessed. Compounds that modulate intracellular calcium levels are identified and may be tested for ability to modulate calcineurin activity or for efficacy in mouse models of schizophrenia. Compounds identified in this screen can also be tested in other screening assays described above (e.g., NFAT activity screen). These methods need not rely on calcium sensitive molecules or sensor proteins but may instead measure calcium directly (including calcium isotopes), or measure flux of another molecule that exhibits similar transport properties or serves as a surrogate for measurement of calcium.

Thus the invention provides a method of identifying a candidate compound for treatment of schizophrenia or susceptibility to schizophrenia comprising steps of: (i) providing a biological system suitable for measuring intracellular calcium; (ii) contacting the biological system with the candidate compound; (iii) measuring intracellular calcium or calcium flux in the biological system; and (iv) identifying the compound as a candidate compound for treatment of schizophrenia or susceptibility to schizophrenia if the level of intracellular calcium or calcium flux in the biological system differs from the level of intracellular calcium or calcium flux that occurs or would be expected to occur in the absence of the compound. According to certain embodiments of the invention the biological system is a cell or population of cells. According to certain embodiments of the invention the measuring step comprises measuring level or flux of a calcium sensitive molecule or activity of a calcium sensor protein.

G. Molecular Drug Design. The invention provides methods for rational drug design based on molecular modeling for identification of candidate compounds for treatment of schizophrenia or schizophrenia susceptibility, e.g., using the three-dimensional structure (crystal structure, NMR solution structure, etc.) of CN and/or calcineurin complexes including other components of the calcineurin signaling pathway. Such methods may be particularly useful, e.g., to identify compounds that may interfere with binding between CaN and an inhibitory protein or to identify compounds that interfere with the auto-inhibitory domain of calcineurin. The crystal structure of calcineurin and of the FKBP12-FK506-calcineurin complex have been reported [51, 52].

Structural information may also be used to guide selection of appropriate compound libraries for screening. Thus the invention provides a method for identifying a candidate compound for treatment of schizophrenia or schizophrenia susceptibility comprising steps of: (i) providing a molecular structure of CN or a CN complex; (ii) identifying a structure that is expected to bind to CN or a CN complex or to prevent binding of CN or of a CN subunits either to another CN subunit or to a CN interacting molecule; and (iii) selecting a compound having such a structure as a candidate compound for treatment of schizophrenia or schizophrenia susceptibility.

H. Screen for Compounds that Modulate the Binding of Calcineurin and Calmodulin. As mentioned above, cal-cineurin activity generally requires the binding of calmodulin, which is calcium dependent. Therefore, compounds that alter the binding of calmodulin to calcineurin are likely to modulate calcineurin activity. For example, compounds that enhance the binding of calmodulin to calcineurin, or modestly decrease the calcium dependence of this interaction (i.e. stabilize the binding at lower calcium concentration) are likely to enhance calcineurin activity. The invention therefore provides a method for identifying compounds that alter the binding of calmodulin and calcineurin. According to certain embodiments of the invention purified and/or recombinant calcineurin and calmodulin are generated, and standard screens for protein-protein interactions (e.g., two or three hybrid screens, where two hybrid screens is taken to include reverse two hybrid screens) are employed. See, e.g., Serebriiskii, I. G. et al., *Methods Mol Biol* 2001; 175:415-54; Vidal, M. and Endoh, H. Trends Biotechnol September 1999; 17(9): 374-81; Kolanus, W., *Curr Top Microbiol Immunol* 1999; 243:37-54 and references in the foregoing articles.

According to other embodiments of the invention, bioluminescence resonance energy transfer screens with recombinant, fluorescently tagged calmodulin and calcineurin proteins (Boute, N., et al., *Trends in Pharmacol Sci* (2002) 23(8): 351-4) are used. The screens can be performed at different calcium concentrations to screen for molecules that stabilize the interaction in a calcium dependent manner. These screens can be performed with specific CNA subunits to screen for compounds that modulate calcineurin-calmodulin binding in a CNAγ, CNAα or CNAβ-specific manner.

The above screens can also be performed using CN and calmodulin isolated and/or purified from cells, in which case candidate compounds may be added to CN and calmodulin after their isolation/purification, or the cells may be treated with compound prior to isolation, and CN, calmodulin, and/or CN-calmodulin complexes may be isolated from the cells. Any of the above screens (and others described herein) can be performed using a range of different calcium concentrations.

I. Screens for CNAγ-interacting Molecules. While not wishing to be bound by any theory, the inventors' discovery that the PPP3CC gene is associated with schizophrenia susceptibility (see Examples 3 and 4) suggests that CNAγ, molecules that that interact with CNAγ, and particularly potential specific substrates of CNAγ could be involved with schizophrenia pathogenesis molecules. Therefore, molecules that interact with CNAγ and particularly potential specific substrates of CNAγ may be particularly attractive candidate compounds for treatment of schizophrenia or susceptibility to schizophrenia and/or particularly attractive molecular targets for development of therapeutic agents.

The invention therefore provides methods for identification of candidate molecules for treatment of schizophrenia or susceptibility to schizophrenia and molecular targets for development of treatments for schizophrenia or susceptibility to schizophrenia. According to certain embodiments of the invention such compounds and targets are CNAγ-interacting proteins. Such proteins can be identified using standard two-hybrid methodology (e.g., in yeast or mammalian cells, etc.). In addition, CNAγ-interacting proteins can be identified by standard biochemical means, for example, subjecting cellular extracts to CNAγ affinity column chromatography. CNAγ-specific substrates can be identified by comparing the protein phosphorylation profiles of cell lines with and without CNAγ (e.g., using RNAi inactivation of CNAγ) following calcineurin activation using, for example, cellular phosphate labeling (e.g., radioactive phosphate labeling) and two-dimensional protein gel electrophoresis. Proteins that are specifically dephosphorylated in the CNAγ containing cells can be isolated and microsequenced for identification. This screen can also be applied to identify calcineurin substrates in general.

J. Additional In Vitro and In Vivo Screening Methods to Identify Candidate Compounds for Treatment of Schizophrenia and Schizophrenia Susceptibility Compounds may be tested in vitro or in vivo for their ability to inhibit binding of CN to an inhibitory protein. For example, the ability of a candidate compound to inhibit binding of CaN to an inhibitory protein may be tested in vitro using purified (e.g., recombinant) proteins and/or extracts from cells expressing one or more of these components. Components may be mixed in the absence or presence of the candidate compound, and complexes containing CN can be isolated and assayed to determine whether they contain the inhibitory protein. Appropriate isolation and detection methods (e.g., immunoprecipitation, Western blot, ELISA) can be employed. The ability of a candidate compound to inhibit binding of calcineurin to an inhibitory protein may similarly be assayed in intact cells using, e.g., co-immunoprecipitation. See, e.g., methods employed in [39]. Cells may naturally express the components or be engineered to do so.

In any methods employing recombinant proteins it may be desirable to use proteins that include a tag, e.g., a GST tag, FLAG tag, HA epitope tag, etc. Construction of appropriate expression vectors and their introduction into cells can be performed using standard methods, e.g., as described in [53]. It may be desirable to engineer calcineurin proteins or other components of the calcineurin signaling pathway to include a readily detectable marker, e.g., a fluorescent or luminescent marker such as GFP. Such readily detectable proteins may be useful to study the effect of compounds on the subcellular localization of calcineurin, etc. For example, compounds that interfere with the interaction of calcineurin and a calcineurin targeting protein such as AKAP5 may be identified using such an approach.

Any of the various compound identification and screening methods described above may be employed in a high throughput format or may readily be modified for high throughput screening.

K. Compounds for Screening. Compounds suitable for use in any of the compound identification methods described above (or other methods) include small molecules, natural products, peptides, nucleic acids, etc. Sources for compounds include natural product extracts, collections of synthetic compounds, and compound libraries generated by combinatorial chemistry. Libraries of compounds are well known in the art. One representative example is known as DIVERSet™, available from ChemBridge Corporation, 16981 Via Tazon, Suite G, San Diego, Calif. 92127. DIVERSet™ contains between 10,000 and 50,000 drug-like, hand-synthesized small molecules. The compounds are pre-selected to form a "universal" library that covers the maximum pharmacophore diversity with the minimum number of compounds and is suitable for either high throughput or lower throughput screening. For descriptions of additional libraries, see, for example, Tan, et al., "Stereoselective Synthesis of Over Two Million Compounds Having Structural Features Both Reminiscent of Natural Products and Compatible with Miniaturized Cell-Based Assays", *Am. Chem Soc.* 120, 8565-8566, 1998; Floyd C D, Leblanc C, Whittaker M, *Prog Med Chem* 36:91-168, 1999. Numerous libraries are commercially available, e.g., from AnalytiCon USA Inc., P.O. Box 5926, Kingwood, Tex. 77325; 3-Dimensional Pharmaceuticals, Inc., 665 Stockton Drive, Suite 104, Exton, Pa. 19341-1151; Tripos, Inc., 1699 Hanley Rd., St. Louis, Mo., 63144-2913, etc. See also U.S. Pat. No. 6,448,443 and PCT publication WO9964379.

In general, compounds may be dissolved in any appropriate solvent, preferably a solvent that does not exert deleterious effects on the growth of cells, if the screen involves cells. A range of concentrations of the compound may be tested for the desired effect. As is well known to one of ordinary skill in the art, virtually any compound can have deleterious effects on an organism if present at sufficiently high concentration. Preferred compounds exert their effects at concentrations practical for administration as therapeutic agents (e.g., at concentrations that do not cause unacceptable adverse effects in the subject being treated). Screens can be performed, for example, at relatively low concentrations such as <0.1 µg/ml, at higher concentrations such as 1 to 100 µg/ml, or at still higher concentrations, e.g., up to 1 mg/ml. In general, one of ordinary skill in the art will be able to select appropriate concentration ranges for testing, and the foregoing examples are not intended to be limiting.

L. Screens for Effectiveness of Candidate Compounds in Animal Models and Humans

Candidate compounds identified using any of the screening methods described herein (or other suitable methods) can be tested in any appropriate animal model for schizophrenia including both genetic and pharmacological models. For example, such compounds can be tested in the CNB knockout mouse and/or in any of the models described in Gainetdinov, et al., "Genetic animal models: focus on schizophrenia", *Trends in Neurosciences*, Vol. 24, No. 9, September 2001. Such models include various selected or developed (e.g., using gene targeting technology) strains of mice (e.g., mice having mutations or deletions in various components of neurotransmitter systems such as the NMDA receptor, dopamine transporter, etc.). Alternately, animal models may be obtained by exposing the animals to appropriate compounds such as PCP, etc., that result in development of symptoms suggestive of schizophrenia.

When testing compounds in animal models, it may be preferred to use an animal model that does not contain a mutation or deletion in the expected target of the compound (although such animal models may usefully be employed as controls for specificity of the compound since if the compound is similarly effective in such animal models it is most likely acting via a mechanism that does not involve interaction with the expected target). Candidate compounds can also be tested in human subjects suffering from schizophrenia or a related condition or susceptibility thereto.

In general, such tests for efficacy involve administering the candidate compound to the subject (whether animal or human) and observing the subject to determine whether administration of the compound results in amelioration in or reduction of any sign or symptom of schizophrenia (or results in a decreased incidence of developing schizophrenia). Any of the phenotypes characteristic of animal models of schizophrenia (i.e., phenotypes suggestive of schizophrenia) may be assessed, including, but not limited to, those activities and behaviors described in Example 1.

In humans, any of the parameters used in the diagnosis and/or assessment of patients suffering from or suspected of suffering from schizophrenia or a related condition may be assessed. Methodology for performing clinical trials of candidate therapeutic agents for schizophrenia in humans is well established. According to certain embodiments of the invention human subjects for the clinical trial are selected by identifying subjects at risk of or suffering from schizophrenia using any of the inventive methods described herein. For example, subjects may be selected by detecting a polymorphic variant of a polymorphism in a coding or noncoding portion of a gene encoding a calcineurin subunit or encoding a calcineurin interacting molecule, or detecting a polymorphic variant of a polymorphism in a genomic region linked to such a gene, in a sample obtained from the subject. According to certain embodiments of the invention a group of subjects selected using any of the inventive methods is compared with a group of subjects selected using any other diagnostic criterion.

Thus the invention provides a method for identifying a candidate compound for treatment of schizophrenia comprising steps of: (i) providing a subject or subjects at risk of or exhibiting one or more phenotypes suggestive of schizophrenia, wherein the subject or subjects have an alteration in expression of at least one calcineurin subunit or calcineurin interacting molecule; (ii) administering the candidate compound to the subject or subjects; (iii) comparing severity or incidence of the phenotype in the subject or subjects to severity or incidence of the phenotype in a subject or subjects to which the compound is not administered. Typically the method will be performed using groups of animals. If the phenotype appears less severe or occurs at reduced frequency in the subject(s) to which the compound is administered, the compound is identified a candidate compound for the treatment of schizophrenia and/or schizophrenia susceptibility (although of course this may be confirmed using additional methods).

According to certain embodiments of the invention the subject that receive the compound and those that do not receive the compound (i.e., controls) are genetically similar or identical animals. (It is noted that historical controls can be used.) According to certain embodiments of the invention the animal is a CNB-deficient mouse. According to certain embodiments of the invention the compound is any compound identified according to any of the inventive compound screening methods described herein, e.g., a compound that modulates activity or abundance of calcineurin, a calcineurin subunit, or a calcineurin interacting molecule to the subject.

M. Animal Models for Efficacy Screens of Candidate Compounds. In addition to the CNB-deficient mouse described herein, the invention provides a number of other animal models for schizophrenia and/or schizophrenia susceptibility. The invention provides a transgenic animal, e.g., a mouse, expressing an altered form of a calcineurin subunit or calcineurin interacting molecule. The invention further provides a transgenic animal that overexpresses a calcineurin subunit or calcineurin interacting molecule. The subunit or interacting molecule may be any of the subunits or molecules listed in Table 1. According to certain embodiments of the invention the subunit is CNAγ.

The invention provides a calcineurin subunit murine hypomorph, wherein the CN subunit is any CN subunit. The invention further provides additional murine hypomorphs, wherein the hypomorphic locus is any gene encoding a CN interacting molecule, including but not limited to, a gene encoding any protein selected from the group consisting of Cabin 1; calcineurin B homologous protein; calcipressins such as DSCR-1; calsarcin-1; calsarcin-3; A kinase anchor protein 5; FK506 binding protein 5; interleukin enhancer binding factor 2 (ILF2 subunit of nuclear factor of activated T cells); nuclear factor of activated T cells, cytoplasmic, calcineurin dependent 2; ryanodine receptor type 3; IP3 (inositol triphosphate) receptor type 1; pituitary adenylate cyclase activating polypeptide (PACAP); and calcium-signal modulating cyclophilin ligand (CAML).

By "hypomorph" is meant an animal that expresses a given gene at less than wild type levels but at greater levels than would result from complete deletion of the gene (or other complete elimination of expression). For example, a hypomorph may express a gene at less than 50%, less than 25%, less than 10%, less than 5%, less than 1%, or an even lower percentage, but greater than 0, of the wild type level of expression. Hypomorphs expressing between 10% and 30% of the wild type level of expression may be preferred. Hypomorphic mice may be particularly useful when complete deletion or inactivation of the gene results in embryonic lethality or severe defects that prevent or impede assessment of phenotypes of interest (e.g., phenotypes suggestive of schizophrenia). Hypomorphic mice may be created, for example, by "knock in" of promoters such as the PGK promoter as described in [25]. This promoter has been shown to severely repress transcription at targeted loci, and this method has been used to create a mouse NMDA receptor hypomorph [25]. In general, the term "hypomorph" does not refer to tissue-specific or regional knockouts. However, the term includes tissue or region-specific reductions in expression.

The invention further provides mice having tissue restricted expression of any gene encoding a CN subunit or CN interacting molecule. In particular, the invention provides mice lacking or having reduced expression of a gene encoding a CN subunit or CN interacting molecule in one or more nervous system regions, e.g., in one or more regions of the brain.

In general, mice that over-express or under-express any of the above-mentioned components of the calcineurin signaling pathway may be generated according to a variety of conventional, recently developed, or emerging transgenic or knockout techniques. Such techniques may include use of cell or tissue specific regulatory elements, inducible systems, etc. See, e.g., Kwan, K., "Conditional alleles in mice: practical considerations for tissue-specific knockouts." *Genesis*, 32(2): 49-62, 2002; Lewandowski, M., "Conditional control of gene expression in the mouse", *Nat. Rev. Genet.*, 2(10): 743-55, 2001; Bockamp, E., et al., *Physiol Genomics* 11(3):115-32 (2002).

As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA or a rearrangement, e.g., a deletion of endogenous chromosomal DNA, which preferably is integrated into or occurs in the genome of the cells of a transgenic animal. Thus "knockout" animals are included. A transgene can, but need not, replace an endogenous gene. A transgene can direct the expression of an encoded product in one or more cell types or tissues of the transgenic animal.

According to certain embodiments of the invention murine hypomorphs or effective null mutants are generated by expressing an siRNA targeted to a CN subunit or CN interacting molecule in the mouse (which may be done in a tissue or cell type specific manner, or in an inducible manner if desired.) According to certain embodiments of the invention such expression is achieved using lentiviral vectors as described, for example, in U.S. Provisional Patent Application No. 60/428,039, filed Nov. 21, 2002. Such mice can be crossed to generate compound homo or heterozygotes. The invention further provides mice generated by crossing any of the inventive mice described above either with other members of this group (e.g., crossing a CNB hypomorph, CNAγ hypomorph, CNB knockout, CNAγ hypomorph, etc, with a mouse hypomorphic or knocked out for any of the other genes encoding a CN subunit or CN interacting molecule) or with mice of any different genotype including, but not limited to, mice used as models for schizophrenia (e.g., mice having mutations in the gene encoding a subunit of the NMDA receptor, dopamine transporter, etc.), and mice expressing a recombinase such as Cre in a tissue-specific manner.

In particular, the invention provides transgenic and knock-out mice, including CNAγ hypomorphs that overexpress or underexpress the gene encoding CNAγ (PPP3CC) or express a variant of the gene. Such mice may be particularly useful for testing CNAγ-directed and additional compounds for treatment of schizophrenia or schizophrenia susceptibility.

The invention provides transgenic animals that expresses a variant of a CN subunit or CN interacting molecule, wherein the variant occurs at a homolous location to the location of a variant in a homologous human protein, wherein the variant is associated with schizophrenia or susceptibility to schizophrenia. The human variant is encoded by a gene having a polymorphic variant associated with schizophrenia or susceptibility to schizophrenia.

Although described primarily with reference to mice, the invention is not limited to such animals but also includes any other animal in which genetically engineered variants can be made including, but not limited to, rats, sheep, pigs, goats, bovine animals, and, possibly, primates. In particular, it is noted that siRNA mediated gene silencing has been demonstrated in transgenic rats (Hasuwa, H., et al., FEBS Lett Dec. 4, 2002; 532(1-2):227-30.

Any of the animals described above may be used to screen for efficacy of candidate compounds for treatment of schizophrenia or susceptibility to schizophrenia. A mouse hypomorphic for any particular protein may be particularly useful for testing compounds designed to enhance the activity of that protein. These mice can be used for both biochemical and behavioral assays to validate candidate compounds.

VI. Compounds and Methods for Treatment of Schizophrenia or Schizophrenia Susceptibility A. Compounds and Methods of Use. The present invention provides compounds identified according to any of the inventive compound identification methods described above. According to certain embodiments of the invention preferred compounds exhibit the ability to cross the blood-brain barrier, so that a therapeutically effective concentration in the central nervous system may be achieved. Candidate compounds, e.g., compounds identified using in vitro methods may be appropriately modified, e.g., by conjugation with a lipophilic moiety or by any of various methods known in the art in order to enhance their ability to cross the blood-brain barrier. According to certain embodiments of the invention compound libraries, e.g., combinatorial libraries, are synthesized using an appropriate starting compound and/or substituents, so as to increase the likelihood that the compound will cross the blood-brain barrier.

In general, any of the compounds identified as described above may be further optimized to reduce or eliminate undesirable properties and/or to increase or enhance desirable properties. For example, compounds may be modified to increase solubility, increase absorbability, or otherwise enhance bioavailability. Such compounds may be useful as therapies and/or as lead compounds for the design or selection of further compounds. The invention thus provides derivatives of compounds identified according to the screening methods above, e.g., derivatives that display enhanced bioavailability, enhanced ability to cross the blood-brain barrier, improved safety profile, etc.

It is noted that any of the compounds identified according to the inventive methods described above may have a number of additional uses, both for research and therapeutic purposes, and their identification as candidate compounds for use in treatment of schizophrenia or schizophrenia susceptibility is not intended to limit their applications in any way.

The invention provides methods of treating schizophrenia or susceptibility to schizophrenia comprising steps of (i) providing a subject at risk of or suffering from schizophrenia; and (ii) administering a compound identified according to any of the inventive methods described above to the subject.

The invention provides a method for treating schizophrenia or susceptibility to schizophrenia comprising: (i) providing a subject at risk of or suffering from schizophrenia; and (ii) administering a compound that modulates activity or abundance of calcineurin, a calcineurin subunit, or a calcineurin interacting molecule to the subject. According to various embodiments of the invention the compound enhances activity or abundance of calcineurin, a calcineurin subunit, or a calcineurin interacting molecule. According to certain other embodiments of the invention the compound reduces activity or abundance of calcineurin, a calcineurin subunit, or a calcineurin interacting molecule. According to certain embodiments of the invention the compound modulates (e.g., enhances or reduces) activity of calcineurin, a calcineurin subunit, or a calcineurin interacting molecule. According to certain embodiments of the invention the calcineurin, calcineurin subunit, or calcineurin interacting molecule is selected from the group consisting of: CNB; CNAa; CNAb; CNAg; Cabin 1; calcineurin B homologous protein; calcipressins; DSCR-1; calsarcin-1; calsarcin-3; A kinase anchor protein 5; FK506 binding protein 5; interleukin enhancer binding factor 2 (ILF2 subunit of nuclear factor of activated T cells); nuclear factor of activated T cells, cytoplasmic, calcineurin dependent 2; ryanodine receptor type 3; IP3 (inositol triphosphate) receptor type 1; pituitary adenylate cyclase activating polypeptide (PACAP); and calcium-signal modulating cyclophilin ligand. Appropriate compounds include, but are not limited to, those identified according to any of the inventive compound screening methods described above.

B. Gene Therapy. The invention also provides methods of treating schizophrenia or susceptibility to schizophrenia using gene therapy, wherein a calcineurin subunit or calcineurin interacting molecule (including altered versions of such subunits or molecules) is expressed in cells of a subject. The calcineurin subunit or calcineurin interacting molecule may be any of those listed in Table 1, or others. Alternately, according to certain embodiments of the invention an inhibitory siRNA targeted to a calcineurin subunit or calcineurin molecule is expressed so as to reduce or eliminate endogenous expression of the subunit or molecule. Other gene therapy based methods of reducing expression of these molecules may also be used. Methods for modulating the transcription of CN subunits or CN interacting molecules are also within the scope of the invention. See, e.g., U.S. Pat. No. 6,326,166. Methods and vectors for gene therapy are known in the art. In general, gene therapy vectors include retroviruses, lentiviruses, adenoviruses, adeno-associated viruses, and a number of non-viral vectors. According to the inventive methods a nucleic acid encoding the desired subunit or molecule is introduced into a gene therapy vector under control of appropriate regulatory elements. Such regulatory elements may be selected to achieve inducible or constitutive expression in a cell type or tissue of choice or throughout the body.

Gene therapy protocols may involve administering an effective amount of a gene therapy vector capable of directing expression of a calcineurin subunit or calcineurin interacting molecule or inhibitory siRNA to a subject either before, substantially contemporaneously, with, or after influenza virus infection. Another approach that may be used alternatively or in combination with the foregoing is to isolate a population of cells, e.g., stem cells or immune system cells from a subject, optionally expand the cells in tissue culture, and administer a gene therapy vector capable of directing expression of a calcineurin subunit or calcineurin interacting molecule or an inhibitory siRNA to the cells in vitro. The cells may then be returned to the subject. Optionally, cells expressing the calcineurin subunit or calcineurin interacting molecule siRNA can be selected in vitro prior to introducing them into the subject. In some embodiments of the invention a population of cells, which may be cells from a cell line or from an individual who is not the subject, can be used. Methods of isolating stem cells, immune system cells, etc., from a subject and returning them to the subject are well known in the art. Such methods are used, e.g., for bone marrow transplant, peripheral blood stem cell transplant, etc., in patients undergoing chemotherapy.

In yet another approach, oral gene therapy may be used. For example, U.S. Pat. No. 6,248,720 describes methods and compositions whereby genes under the control of promoters are protectively contained in microparticles and delivered to cells in operative form, thereby achieving noninvasive gene delivery. Following oral administration of the microparticles, the genes are taken up into the epithelial cells, including absorptive intestinal epithelial cells, taken up into gut associated lymphoid tissue, and even transported to cells remote from the mucosal epithelium. As described therein, the microparticles can deliver the genes to sites remote from the mucosal epithelium, i.e. can cross the epithelial barrier and enter into general circulation, thereby transfecting cells at other locations.

VII. Additional Methods, Reagents, and Compounds

The invention provides a number of additional methods, reagents, and compounds that may be used either for the treatment of schizophrenia or schizophrenia susceptibility, the development of treatments for schizophrenia or schizophrenia susceptibility, the practice of the other inventive methods described herein, or for a variety of other purposes.

A. Short Interfering RNAs. RNA interference (RNAi) is a mechanism of post-transcriptional gene silencing mediated by double-stranded RNA (dsRNA), which is distinct from antisense and ribozyme-based approaches. dsRNA molecules are believed to direct sequence-specific degradation of mRNA in cells of various types after first undergoing processing by an RNase III-like enzyme called DICER (Bernstein et al., *Nature* 409:363, 2001) into smaller dsRNA molecules comprised of two 21 nt strands, each of which has a 5' phosphate group and a 3' hydroxyl, and includes a 19 nt region precisely complementary with the other strand, so that there is a 19 nt duplex region flanked by 2 nt-3' overhangs. RNAi is thus mediated by short interfering RNAs (siRNA), which typically comprise a double-stranded region approximately 19 nucleotides in length with 1-2 nucleotide 3' overhangs on each strand, resulting in a total length of between approximately 21 and 23 nucleotides. In mammalian cells, dsRNA longer than approximately 30 nucleotides typically induces nonspecific mRNA degradation via the interferon response. However, the presence of siRNA in mammalian cells, rather than inducing the interferon response, results in sequence-specific gene silencing.

In general, a short, interfering RNA (siRNA) comprises an RNA duplex that is preferably approximately 19 basepairs long and optionally further comprises one or two single-stranded overhangs or loops. An siRNA may comprise two RNA strands hybridized together, or may alternatively comprise a single RNA strand that includes a self-hybridizing portion. siRNAs may include one or more free strand ends, which may include phosphate and/or hydroxyl groups. siRNAs typically include a portion that hybridizes under stringent conditions with a target transcript. One strand of the siRNA (or, the self-hybridizing portion of the siRNA) is typically precisely complementary with a region of the target transcript, meaning that the siRNA hybridizes to the target transcript without a single mismatch. In certain embodiments of the invention in which perfect complementarity is not achieved, it is generally preferred that any mismatches be located at or near the siRNA termini.

siRNAs have been shown to downregulate gene expression when transferred into mammalian cells by such methods as transfection, electroporation, or microinjection, or when expressed in cells via any of a variety of plasmid-based approaches. RNA interference using siRNA is reviewed in, e.g., Tuschl, T., Nat. Biotechnol., 20: 446-448, May 2002. See also Yu, J., et al., Proc. Natl. Acad. Sci., 99(9), 6047-6052 (2002); Sui, G., et al., Proc. Natl. Acad. Sci., 99(8), 5515-5520 (2002); Paddison, P., et al., Genes and Dev., 16, 948-958 (2002); Brummelkamp, T., et al., Science, 296, 550-553 (2002); Miyagashi, M. and Taira, K., Nat. Biotech., 20, 497-500 (2002); Paul, C., et al., Nat. Biotech., 20, 505-508 (2002). As described in these and other references, the siRNA may consist of two individual nucleic acid strands or of a single strand with a self-complementary region capable of forming a hairpin (stem-loop) structure. A number of variations in structure, length, number of mismatches, size of loop, identity of nucleotides in overhangs, etc., are consistent with effective siRNA-triggered gene silencing. While not wishing to be bound by any theory, it is thought that intracellular processing (e.g., by DICER) of a variety of different precursors results in production of siRNA capable of effectively mediating gene silencing. Generally it is preferred to target exons rather than introns, and it may also be preferable to select sequences complementary to regions within the 3' portion of the target transcript. Generally it is preferred to select sequences that contain approximately equimolar ratio of the different nucleotides and to avoid stretches in which a single residue is repeated multiple times.

siRNAs may thus comprise RNA molecules having a double-stranded region approximately 19 nucleotides in length with 1-2 nucleotide 3' overhangs on each strand, resulting in a total length of between approximately 21 and 23 nucleotides. As used herein, siRNAs also include various RNA structures that may be processed in vivo to generate such molecules. Such structures include RNA strands containing two complementary elements that hybridize to one another to form a stem, a loop, and optionally an overhang, preferably a 3' overhang. Preferably, the stem is approximately 19 bp long, the loop is about 1-20, more preferably about 4-10, and most preferably about 6-8 nt long and/or the overhang is about 1-20, and more preferably about 2-15 nt long. In certain embodiments of the invention the stem is minimally 19 nucleotides in length and may be up to approximately 29 nucleotides in length. Loops of 4 nucleotides or greater are less likely subject to steric constraints than are shorter loops and therefore may be preferred. The overhang may include a 5' phosphate and a 3' hydroxyl. The overhang may but need not comprise a plurality of U residues, e.g., between 1 and 5 U residues.

Classical siRNAs as described above trigger degradation of mRNAs to which they are targeted, thereby also reducing the rate of protein synthesis. In addition to siRNAs that act via the classical pathway, certain siRNAs that bind to the 3' UTR of a template transcript may inhibit expression of a protein encoded by the template transcript by a mechanism related to but distinct from classic RNA interference, e.g., by reducing translation of the transcript rather than decreasing its stability. Such RNAs are referred to as microRNAs (mRNAs) and are typically between approximately 20 and 26 nucleotides in length, e.g., 22 nt in length. It is believed that they are derived from larger precursors known as small temporal RNAs (stRNAs) or mRNA precursors, which are typically approximately 70 nt long with an approximately 4-15 nt loop. (See Grishok, A., et al., Cell 106, 23-24, 2001; Hutvagner, G., et al., Science, 293, 834-838, 2001; Ketting, R., et al., Genes Dev., 15, 2654-2659). Endogenous RNAs of this type have been identified in a number of organisms including mammals, suggesting that this mechanism of post-transcriptional gene silencing may be widespread (Lagos-Quintana, M. et al., Science, 294, 853-858, 2001; Pasquinelli, A., Trends in Genetics, 18(4), 171-173, 2002, and references in the foregoing two articles). MicroRNAs have been shown to block translation of target transcripts containing target sites in mammalian cells (Zeng, Y., et al., Molecular Cell, 9, 1-20, 2002).

siRNAs such as naturally occurring or artificial (i.e., designed by humans) mRNAs that bind within the 3' UTR (or elsewhere in a target transcript) and inhibit translation may tolerate a larger number of mismatches in the siRNA/template duplex, and particularly may tolerate mismatches within the central region of the duplex. In fact, there is evidence that some mismatches may be desirable or required as naturally occurring stRNAs frequently exhibit such mismatches as do mRNAs that have been shown to inhibit translation in vitro. For example, when hybridized with the target transcript such siRNAs frequently include two stretches of perfect complementarity separated by a region of mismatch. A variety of structures are possible. For example, the mRNA may include multiple areas of nonidentity (mismatch). The areas of nonidentity (mismatch) need not be symmetrical in the sense that both the target and the mRNA include nonpaired nucleotides. Typically the stretches of perfect complementarity are at least 5 nucleotides in length, e.g., 6, 7, or more nucleotides in length, while the regions of mismatch may be, for example, 1, 2, 3, or 4 nucleotides in length.

Hairpin structures designed to mimic siRNAs and mRNA precursors are processed intracellularly into molecules capable of reducing or inhibiting expression of target transcripts (McManus, M. T., et al., RNA, 8:842-850, 2002). These hairpin structures, which are based on classical siRNAs consisting of two RNA strands forming a 19 bp duplex structure are classified as class I or class II hairpins. Class I hairpins incorporate a loop at the 5' or 3' end of the antisense siRNA strand (i.e., the strand complementary to the target transcript whose inhibition is desired) but are otherwise identical to classical siRNAs. Class II hairpins resemble mRNA precursors in that they include a 19 nt duplex region and a loop at either the 3' or 5' end of the antisense strand of the duplex in addition to one or more nucleotide mismatches in the stem. These molecules are processed intracellularly into small RNA duplex structures capable of mediating silencing. They appear to exert their effects through degradation of the target mRNA rather than through translational repression as is thought to be the case for naturally occurring mRNAs and stRNAs.

Thus it is evident that a diverse set of RNA molecules containing duplex structures is able to mediate silencing through various mechanisms. For the purposes of the present invention, any such RNA, one portion of which binds to a target transcript and reduces its expression, whether by triggering degradation, by inhibiting translation, or by other means, is considered to be an siRNA, and any structure that generates such an siRNA (i.e., serves as a precursor to the RNA) is useful in the practice of the present invention.

In the context of the present invention, siRNAs are useful both for therapeutic purposes, e.g., to modulate the expression of a calcineurin subunit or calcineurin interacting molecule in a subject at risk of or suffering from schizophrenia and for various of the inventive methods for the identification of compounds for treatment of schizophrenia that modulate the activity or level of calcineurin.

The invention therefore provides a method of inhibiting expression of a gene encoding a calcineurin subunit or calcineurin interacting molecule comprising the step of (i) providing a biological system in which expression of a gene encoding a calcineurin subunit or calcineurin interacting molecule is to be inhibited; and (ii) contacting the system with an siRNA targeted to a transcript encoding the calcineurin subunit or calcineurin interacting molecule. According to certain embodiments of the invention the subunit or molecule is encoded by a gene within or linked to a schizophrenia susceptibility locus, or within which a functional mutation causing or contributing to susceptibility or development of schizophrenia may exist. According to certain embodiments of the invention the biological system comprises a cell, and the contacting step comprises expressing the siRNA in the cell. According to certain embodiments of the invention the biological system comprises a subject, e.g., a mammalian subject such as a mouse or human, and the contacting step comprises administering the siRNA to the subject or comprises expressing the siRNA in the subject. According to certain embodiments of the invention the siRNA is expressed inducibly and/or in a cell-type or tissue specific manner.

The invention provides siRNA molecules targeted to a transcript encoding any calcineurin subunit or calcineurin interacting molecule. In particular, the invention provides siRNA molecules selectively or specifically targeted to a transcript encoding a polymorphic variant of such a transcript, wherein existence of the polymorphic variant in a subject is indicative of susceptibility to or presence of schizophrenia. The terms selectively or specifically targeted to, in this context, are intended to indicate that the siRNA causes greater reduction in expression of the variant than of other variants (i.e., variants whose existence in a subject is not indicative of susceptibility to or presence of schizophrenia). The transcript may encode, for example, any of the molecules listed in Table 1, or a polymorphic variant thereof. The siRNA, or collections of siRNAs, may be provided in the form of kits with additional components as appropriate.

B. Full and Partial Length Antisense RNA Transcripts. Antisense RNA transcripts have a base sequence complementary to part or all of any other RNA transcript in the same cell. Such transcripts have been shown to modulate gene expression through a variety of mechanisms including the modulation of RNA splicing, the modulation of RNA transport and the modulation of the translation of mRNA (Denhardt, Annals N Y Acad. Sci., 660:70, 1992, Nellen, *Trends Biochem. Sci.,* 18:419, 1993; Baker and Monia, *Biochim. Biophys. Acta,* 1489:3, 1999; Xu, et al., *Gene Therapy,* 7:438, 2000; French and Gerdes, *Curr. Opin. Microbiol.,* 3:159, 2000; Terryn and Rouze, *Trends Plant Sci.,* 5: 1360, 2000).

C. Antisense RNA and DNA Oligonucleotides.

Antisense nucleic acids are generally single-stranded nucleic acids (DNA, RNA, modified DNA, or modified RNA) complementary to a portion of a target nucleic acid (e.g., an mRNA transcript) and therefore able to bind to the target to form a duplex. Typically they are oligonucleotides that range from 15 to 35 nucleotides in length but may range from 10 up to approximately 50 nucleotides in length. Binding typically reduces or inhibits the function of the target nucleic acid. For example, antisense oligonucleotides may block transcription when bound to genomic DNA, inhibit translation when bound to mRNA, and/or lead to degradation of the nucleic acid. Reduction in expression of a calcineurin subunit or calcineurin interacting polypeptide may be achieved by the administration of antisense nucleic acids or peptide nucleic acids comprising sequences complementary to those of the mRNA that encodes the polypeptide. Antisense technology and its applications are well known in the art and are described in Phillips, M. I. (ed.) *Antisense Technology*, Methods Enzymol., Volumes 313 and 314, Academic Press, San Diego, 2000, and references mentioned therein. See also Crooke, S. (ed.) "Antisense Drug Technology: Principles, Strategies, and Applications" (1$^{st}$ ed), Marcel Dekker; ISBN: 0824705661; 1st edition (2001) and references therein.

Antisense oligonucleotides can be synthesized with a base sequence that is complementary to a portion of any RNA transcript in the cell. Antisense oligonucleotides may modulate gene expression through a variety of mechanisms including the modulation of RNA splicing, the modulation of RNA transport and the modulation of the translation of mRNA (Denhardt, 1992). Various properties of antisense oligonucleotides including stability, toxicity, tissue distribution, and cellular uptake and binding affinity may be altered through chemical modifications including (i) replacement of the phosphodiester backbone (e.g., peptide nucleic acid, phosphorothioate oligonucleotides, and phosphoramidate oligonucleotides), (ii) modification of the sugar base (e.g., 2'-O-propylribose and 2'-methoxyethoxyribose), and (iii) modification of the nucleoside (e.g., C-5 propynyl U, C-5 thiazole U, and phenoxazine C) [Wagner, Nat. Medicine, 1:1116, 1995; Varga, et al., Immun. Lett., 69:217, 1999; Neilsen, Curr. Opin. Biotech., 10:71, 1999; Woolf, Nucleic Acids Res., 18:1763, 1990].

The invention provides a method of inhibiting expression of a gene encoding a calcineurin subunit or calcineurin interacting molecule comprising the step of (i) providing a biological system in which expression of a gene encoding a calcineurin subunit or calcineurin interacting molecule is to be inhibited; and (ii) contacting the system with an antisense molecule that hybridizes to a transcript encoding the calcineurin subunit or calcineurin interacting molecule. According to certain embodiments of the invention the subunit or molecule is encoded by a gene within or linked to a schizophrenia susceptibility locus, or within which a functional mutation causing or contributing to susceptibility or development of schizophrenia may exist. According to certain embodiments of the invention the biological system comprises a cell, and the contacting step comprises expressing the antisense molecule in the cell. According to certain embodiments of the invention the biological system comprises a subject, e.g., a mammalian subject such as a mouse or human, and the contacting step comprises administering the antisense molecule to the subject or comprises expressing the antisense molecule in the subject. The expression may be inducible and/or tissue or cell type-specific. The antisense molecule may be an oligonucleotide or a longer nucleic acid molecule. The invention provides such antisense molecules.

D. Ribozymes. Certain nucleic acid molecules referred to as ribozymes or deoxyribozymes have been shown to catalyze the sequence-specific cleavage of RNA molecules. The cleavage site is determined by complementary pairing of nucleotides in the RNA or DNA enzyme with nucleotides in the target RNA. Thus, RNA and DNA enzymes can be designed to cleave to any RNA molecule, thereby increasing its rate of degradation [Cotten and Birnstiel, *EMBO J.* 8:3861-3866, 1989; Usman, et al., Nucl. Acids Mol. Biol., 10:243, 1996; Usman, et al., Curr. Opin. Struct. Biol., 1:527, 1996; Sun, et al., Pharmacol. Rev., 52:325, 2000]. See also e.g., Cotten and Birnstiel, "Ribozyme mediated destruction of RNA in vivo", *EMBO J.* 8:3861-3866, 1989.

The invention provides a method of inhibiting expression of a gene encoding a calcineurin subunit or calcineurin interacting molecule comprising the step of (i) providing a biological system in which expression of a gene encoding a calcineurin subunit or calcineurin interacting molecule is to be inhibited; and (ii) contacting the system with a ribozyme that hybridizes to a transcript encoding the calcineurin subunit or calcineurin interacting molecule and directs cleavage of the transcript. According to certain embodiments of the invention the subunit or molecule is encoded by a gene within or linked to a schizophrenia susceptibility locus, or within which a functional mutation causing or contributing to susceptibility or development of schizophrenia may exist. According to certain embodiments of the invention the biological system comprises a cell, and the contacting step comprises expressing the ribozyme in the cell. According to certain embodiments of the invention the biological system comprises a subject, e.g., a mammalian subject such as a mouse or human, and the contacting step comprises administering the ribozyme to the subject or comprises expressing the ribozyme in the subject. The expression may be inducible and/or tissue or cell-type specific according to certain embodiments of the invention. The invention provides ribozymes designed to cleave transcripts encoding calcineurin subunits or calcineurin interacting molecules, or polymorphic variants thereof, as described above.

VIII. Pharmaceutical Compositions for Treatment of Schizophrenia or Schizophrenia Susceptibility Inventive compositions may be formulated for delivery by any available route including, but not limited to parenteral (e.g., intravenous), intradermal, subcutaneous, oral (e.g., inhalation), transdermal (topical), transmucosal, rectal, and vaginal. Preferred routes of delivery include parenteral, transmucosal, rectal, and vaginal. Inventive pharmaceutical compositions typically include an active compound or salt thereof, or a related compound or analog, in combination with a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions. For delivery of nucleic acids or polypeptides for treatment or other purposes it may be desirable to use any of a variety of lipid and/or polymeric carriers and matrices. (See, e.g., patents and published PCT applications by Langer, et al. for discussion of polymer-based delivery strategies.) It may be desirable to employ a strategy such as that described in U.S. Pat. No. 6,316,003, relating to novel transport polypeptides which include HIV tat protein or one or more portions thereof, and which are covalently attached to cargo molecules to be delivered to cells.

A pharmaceutical composition is formulated to be compatible with its intended route of administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

Pharmaceutical compositions suitable for injectable use typically include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition should be sterile and should be fluid to the extent that easy syringability exists. Preferred pharmaceutical formulations are stable under the conditions of manufacture and storage and must be preserved against the contaminating action of microorganisms such as bacteria and fungi. In general, the relevant carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. Formulations for oral delivery may advantageously incorporate agents to improve stability within the gastrointestinal tract and/or to enhance absorption.

For administration by inhalation, the inventive compositions are preferably delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit high therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

A therapeutically effective amount of a pharmaceutical composition typically ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The pharmaceutical composition can be administered at various intervals and over different periods of time as required, e.g., one time per week for between about 1 to 10 weeks, between 2 to 8 weeks, between about 3 to 7 weeks, about 4, 5, or 6 weeks, etc. For certain conditions it may be necessary to administer the therapeutic composition on an indefinite basis to keep the disease under control. The skilled artisan will appreciate that certain factors can influence the dosage and timing required to effectively treat a subject, including but not limited to the severity of the disease or disorder, previous treatments, the general health and/or age of the subject, and other diseases present. Generally, treatment of a subject with an inventive composition as described herein, can include a single treatment or, in many cases, can include a series of treatments.

Exemplary doses include milligram or microgram amounts of the inventive composition per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram.) It is furthermore understood that appropriate doses may optionally be tailored to the particular recipient, for example, through administration of increasing doses until a preselected desired response is achieved. It is understood that the specific dose level for any particular subject may depend upon a variety of factors including the activity of the specific compound employed, the age, body weight, general health, gender, and diet of the subject, the time of administration, the route of administration, the rate of excretion, any drug combination, and the degree of expression or activity to be modulated.

Inventive pharmaceutical compositions can be included in a container, pack, or dispenser together with instructions for administration.

Any of the inventive compounds may be administered concurrently with an additional agent useful for treatment of schizophrenia. Many such agents are known in the art and include a wide variety of typical and a typical anti-psychotic agents. In addition, the compounds may be administered concurrently with compounds useful for ameliorating the side effects of anti-psychotic agents. See, for example, Hardman, J. G., et al., (eds.) Goodman & Gilman's The Pharmacological Basis of Therapeutics, 10<sup>th</sup> edition, McGraw Hill, 2001, for discussion of numerous agents useful for the foregoing purposes. The concurrently administered compounds may be administered to the subject separately or may be formulated together.

IX. Methods and Reagents for Identification of Susceptibility Loci and Functional Mutations The invention provides a systematic approach to identifying additional schizophrenia susceptibility loci, polymorphisms useful in diagnosis of schizophrenia or susceptibility to schizophrenia, and to identifying functional mutations that cause or contribute to schizophrenia. The invention provides a method of identifying a method of identifying a polymorphism useful in diagnosis of schizophrenia or susceptibility to schizophrenia comprising steps of (i) identifying one or more polymorphisms in or linked to a gene encoding a CN subunit or CN interacting protein; (ii) providing a set of samples including samples obtained from subjects affected with schizophrenia; and (iii) testing the samples for linkage or association of one or more variants of the polymorphism with schizophrenia. If linkage or association exists, the polymorphism is useful in diagnosis of schizophrenia or susceptibility to schizophrenia. Such polymorphisms may thus be located in or define a schizophrenia susceptibility locus. The set of samples may comprise samples obtained from one or more families affected with schizophrenia and may comprise both related and unrelated individuals.

The invention further provides a method of identifying a candidate functional mutation that causes or contributes to schizophrenia comprising steps of: (i) identifying a polymorphism in or linked to a gene encoding a CN subunit or CN interacting protein; (ii) determining that a polymorphic variant of the polymorphism is linked to or associated with susceptibilty to schizophrenia; (iii) sequencing the gene and optionally regulatory regions of the gene in a sample obtained from one or more subjects suffering from schizophrenia; (iv) comparing the sequence obtained with a normal or wild type sequence of the same gene; and (v) identifying the polymorphic variant as representing a mutation that causes or contributes to schizophrenia if the sequence obtained in step (iii) differs from the normal or wild type sequence.

The methods may further comprise analyzing expression of the gene in normal subjects and in subjects affected with schizophrenia, which includes examining the mRNA abundance, size, and tissue expression pattern, examining the abundance, size, tissue expression pattern and/or activity of the encoded protein, etc.

EXAMPLES

Example 1

Calcineurin-Deficient Mice Display Abnormalities in Activity and Behavior Suggestive of Schizophrenia Materials and Methods Animals and experimental design. The generation of forebrain specific calcineurin knockout mice (CN mutants) is detailed elsewhere [36]. All behavioral tests were carried out with male mice that were 11 weeks old at the start of the testing. Mice were individually housed in a room with a 12-hr light/dark cycle (lights on at 7:00 a.m.) with access to food and water ad libitum. Behavioral testing was performed between 9:00 a.m. and 5:00 p.m. All procedures relating to animal care and treatment conformed to MIT and NIH guidelines.

Motor function tests. Motor coordination and balance were tested with the rotarod test. The rotarod test was performed using an accelerating rotarod (UGO Basile Accelerating Rotarod) and consisted of placing a mouse on a rotating drum (3 cm diameter) and measuring the time each animal was able to maintain its balance on the rod. The speed of the rotarod accelerated from 4 to 40 rpm over a 5-min period.

Object exploration test. The test consisted of 5 trials (10 min/trial). Mice were introduced into a box (40×40×30 cm) made of transparent white plexiglass and allowed to explore freely on the first day (trial 1) and the second day (trial 2) without objects. On the third day, they were placed in the box in the presence of two identical objects (object A; trial 3). Ten min after trial 3, one of the objects was replaced by a novel object (object B) and they were allowed to explore the box with the two different objects (object A and object B; trial 4). On the following day, object B was replaced by another novel object (Object A and object C; trial 5).

Behavior was monitored using a color CCD camera (Sony DXC-151A), which was connected to a Macintosh computer. Locomotor activity, and the time each animal spent around the objects, as well as the time spent in the center part of the field were recorded. Regions of interest (ROI) around the objects were defined as the circles with 8 cm diameter from the center of the object position. When the center of the mouse image was within the defined ROI for each object, the mouse was considered to be 'around the object'. Analysis was performed automatically using Image OE software (see "Image analysis"). The recognition index (RI) was defined as (tB/(tA+tB))/100 as an index for memory on the objects.

Open field test. Each subject was placed in the center of an open field apparatus (40×40×30 cm; Accuscan Instruments, Columbus, Ohio). The apparatus was cleaned with water after each trial. Total distance traveled (cm), vertical activity, time spent in the center and the number and duration of episodes and beam-brake counts for stereotyped behaviors were recorded. Data were collected over a 60 min-period.

Hot plate test. The hot plate test was used to evaluate sensitivity to a painful stimulus. Mice were placed on a 55.0 (±0.3)° C. hot plate (Columbus Instruments, Columbus, Ohio), and latency to the first hind-paw response was recorded. The hind-paw response was either a foot shake or a paw lick.

Light/dark transition test. The apparatus used for the light/dark transition test consisted of a cage (21×42×25 cm) divided into two sections of equal size by a black partition containing a small opening (O'Hara & Co, Tokyo, Japan). One chamber was brightly illuminated, whereas the other chamber was dark. Mice were placed into the illuminated side and allowed to move freely between the two chambers for 10 min. The chambers were cleaned with water after each trial. The total number of transitions, time spent in the dark side, and distance traveled were recorded by Image LD4 software (see 'Image analysis').

Social interaction test. Two mice of identical genotype, which were housed in different cages, were placed into a box together (40×40×30 cm) and allowed to explore freely for 10 min. Social behavior was monitored using a CCD camera (Sony DXC-151A), which was connected to a Macintosh computer. Analysis was performed automatically using Image SI software (see 'Image analysis'). The number of contacts, mean duration per contact, and total distance traveled were measured.

Latent inhibition test. On the training day (day 1), each mouse was placed in a shocking chamber (Coulbourn Instruments, Allentown, Pa.) (Box A). The mice were divided into two groups: preexposed group (P group) and non-preexposed group (NP group). The P group received 40 tones (68 dB, 5 sec duration, 25 sec inter-stimulus interval), whereas the NP group received no stimulus during an equivalent period. Immediately following the tone pre-exposure or the exposure to the chamber, tone-shock pairs consisting of a 5-sec white noise tone (CS) co-terminated with a 2-sec foot shock (US) at 0.40 mA were delivered to both groups with 25 sec inter-stimulus interval. Afterwards, mice remained in the chamber for 25 sec before being returned to the home cage. On day 2, the mice were placed back in Box A for 5 min for the measurement of freezing to the context. On day 3, the mice were put in a white plexiglass chamber (Box B) and, after 180 sec, a 180 sec tone was delivered to measure cued freezing.

Prepulse inhibition task. A startle reflex measurement system was used (MED Associates, St. Albans, Vt.). A test session began by placing a mouse in a plexiglas cylinder where it was left undisturbed for 5 min. The duration of white noise that was used as the startle stimulus was 40 msec for all trial types. The startle response was recorded for 160 msec (measuring the response every 1 msec) starting with the onset of the prepulse stimulus. The background noise level in each chamber was 70 dB. The peak startle amplitude recorded during the 160 msec sampling window was used as the dependent variable. A test session consisted of 6 trial types (i.e. two types for startle stimulus only trials, and four types for prepulse inhibition trials). The intensity of startle stimulus was 100, 105, 110 or 120 dB. The prepulse sound was presented 100 msec before the startle stimulus, and its intensity was 74 or 78 dB. Four combinations of prepulse and startle stimuli were employed (74-110, 78-110, 74-120 and 78-120 for the first batch of subjects and the first test of the second batch of subjects; 74-100, 78-100, 74-105, and 78-105 for the second test of the second batch of animals). Six blocks of the 6 trial types (four trial types with the combinations of prepulse and startle stimulus and two startle stimulus only trials) were presented in pseudorandom order such that each trial type was presented once within a block. The average inter-trial interval was 15 sec (range: 10-20 sec).

Porsolt forced swim test. The apparatus consisted of four glass beakers (15 cm height×10 cm diameter). The cylinders were separated from each other by a non-transparent panel to prevent mice from seeing each other. The cylinders were filled with water (23° C.), up to a height of 7.5 cm. Mice were placed into the cylinders and their behavior was recorded over a 10-min test period. Data acquisition and analysis were performed automatically, using Image PS software (see "Image analysis"). Distance traveled was measured by Image OF software (see "Image analysis") using stored image files.

Quantification of nesting. Pictures of the nests were taken using a digital camera (Olympus, Melvile, N.Y.) and exported into a computer. The number of scattered particles of the nestlets was counted for each cage using the NIH Image program (see Image Analysis).

Image analysis. All applications used for the behavioral studies (Image SI, Image OE, Image LD4, Image PS, Image OF, and Image FZ) were run on a Macintosh computer. Applications were based on the public domain NIH Image program (developed by Wayne Rasband at the U.S. National Institute of Mental Health and available on the Internet at http://rsb.info.nih.gov/nih-image/) and were modified for each test by Tsuyoshi Miyakawa (available through O'Hara & Co., Tokyo, Japan).

Statistical analysis. Statistical analysis was conducted using StatView (SAS institute) or SAS (SAS institute). Data were analyzed by two tailed t-test, two-way ANOVA, or two-way repeated measures ANOVA. Values in tables and graphs were expressed as mean±SEM.

Results

Using conditional gene-targeting techniques, we created mice (referred to herein as CN-KO mice) in which calcineurin activity is disrupted specifically in the mouse adult forebrain [36]. Specifically, we knocked out the fCNB1 gene, which encodes CNB1, the only known regulatory subunit of brain calcineurin, in the excitatory neurons of the adult mouse forebrain. Based on in situ hybridization studies we determined that the fCNB1 gene was deleted only in selected cell types in the hippocampus, neocortex, and amygdala, whereas fCNB1 expression in striatum, cerebellum, and other subcortical regions appeared normal at all ages. The reduction of fCNB1-expressing cells could be first detected in hippocampal CA1 and in cortex at 5 weeks of age, and the deletion pattern described above became evident at approximately 2.5 months of age and remained unchanged at least until 5 months of age, the latest time point examined. The CN-KO mice appeared grossly normal with no obvious sign of sensory or motor impairments. Staining of brain sections by hematoxylin did not reveal any gross structural abnormalities. See [36] for further details and descriptions of additional studies performed on the CN-KO mice.

Previous biochemical studies showed that for the CNA subunits to express their catalytic activity, they must first bind to the CNB regulatory subunit (Merat et al., 1985; Perrino et al., 1992; Sikkink et al., 1995). CNB not only plays a structural role in stabilizing the complex, but also is required for the maximal activation of the phosphatase activity by $Ca^{2+}$-calmodulin (Stemmer and Klee, 1994). Since CNB1 is the sole regulatory subunit in the brain, its deletion would lead to a loss of calcineurin activity.

To assess the role of CN in various aspects of activity and behavior, CN-KO mice were subjected to a battery of tests. These tests reflect aspects of activity and behavior that are altered in human subjects suffering from schizophrenia and other psychiatric disorders. As described below, CN-KO mice displayed a variety of abnormalities indicative of phenotypes characteristic of schizophrenia and/or related disorders.

Increased locomotor activity, stereotyped behavior and exploratory behavior towards inanimate objects. CN mutants weighed about 12% less than their wild-type littermates (controls, 30.3±0.7; CN mutants, 26.6±0.7; $p<0.01$). There were no significant differences in appearance (whiskers and fur), pain sensitivity (hot plate test), and motor coordination (accelerating rotarod tests).

CN mutants showed a pronounced increase in locomotor activity in several different tests. This hyperactivity phenotype was consistently observed in open field, object recognition and social interaction tests. Total distance traveled by CN mutants was significantly greater than that of controls during object exploration (FIG. 1A, $p<0.0001$), open field (FIG. 1B, $p<0.0001$), and social interaction tests (FIG. 2D, $p=0.003$). The number of vertical activities in the open field test (FIG. 1C; genotype effect, $p=0.010$), and the counts of stereotyped behaviors (FIG. 1D, $p=0.001$) were also significantly increased in the CN mutants relative to controls. The number of episodes of stereotyped behavior did not differ significantly between genotypes (FIG. 1F), but the duration of stereotyped behavior was increased in CN mutants compared to controls during the latter half of a 60 min trial (FIG. 1E; time x genotype interaction, $p<0.05$; genotype effect in the latter half of the trial, $p<0.05$).

Figure 1B:
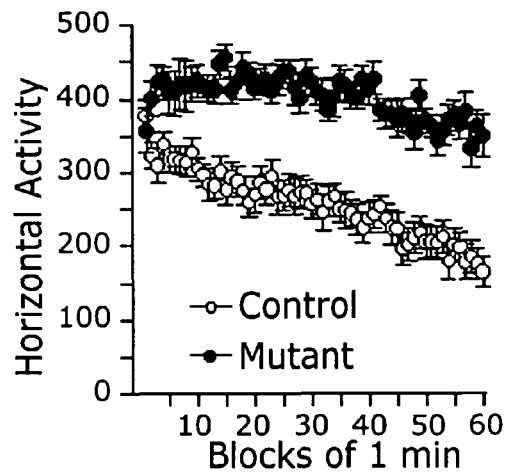
FIG. 1B compares the number of horizontal activities of wild type and CNB-deficient mice in an open field test.
Figure 1C:
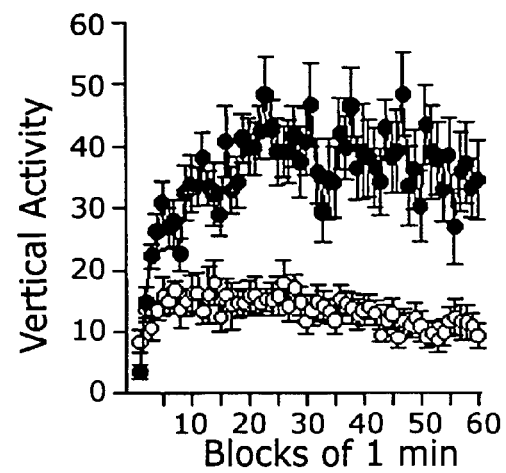
FIG. 1C compares the number of vertical activities of wild type and CNB-deficient mice in an open field test.
Figure 1D:
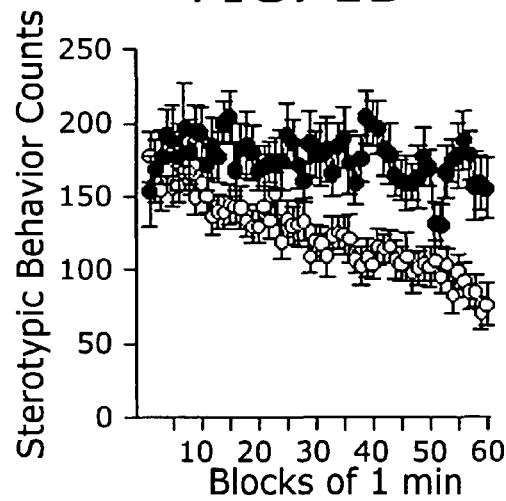
FIG. 1D compares the number of stereotyped behaviors in wild type and CNB-deficient mice.
Figure 1E:
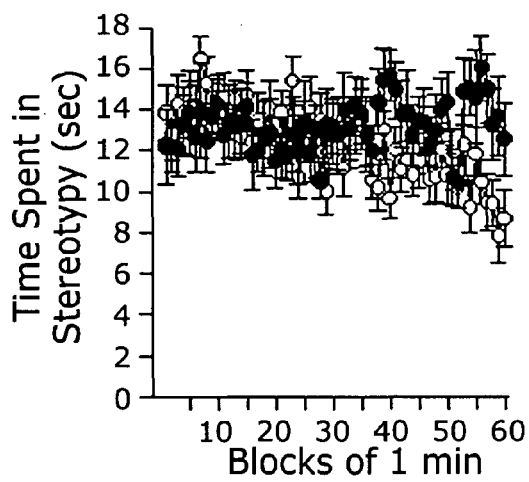
FIG. 1E compares the duration of stereotyped behaviors in wild type and CNB-deficient mice.
Figure 1F:
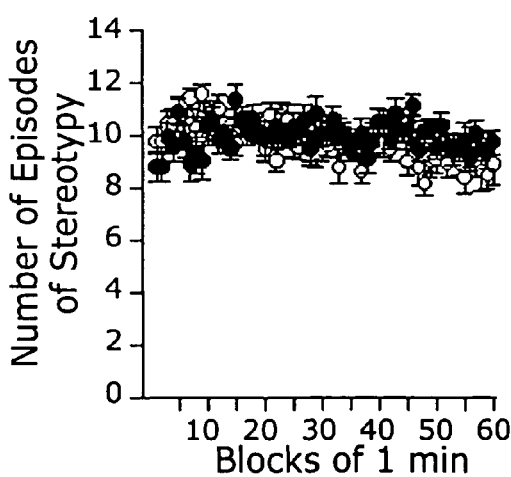
FIG. 1F compares the number of stereotyped behaviors in wild type and CNB-deficient mice.

In the habituation phase of the object exploration test (i.e., trial 1 and trial 2), CN mutants stayed in the peripheral region of the field longer than controls (FIG. 1A upper panel; $p<0.05$). Strikingly, after the objects were introduced into the field (i.e., trial 3, trial 4 and trial 5), CN mutants spent more time in the central region of the field, indicating increased exploratory behavior towards objects ($p<0.01$). Time spent near the objects in CN mutants was significantly longer than that of controls (FIG. 1A bottom panel, $p=0.0088$). CN mutants and controls did not differ significantly with regard to recognition index, either for 1 hour testing (i.e. trial 4) or 24 hour testing (i.e. trial 5) (Data not shown).

No significant differences between CN mutants and controls in distance traveled and time spent in immobile posture in Porsolt forced swim test (data not shown), indicating no obvious abnormality of CN mice in "behavioral despair" as assessed by this test.

Figure 1G:
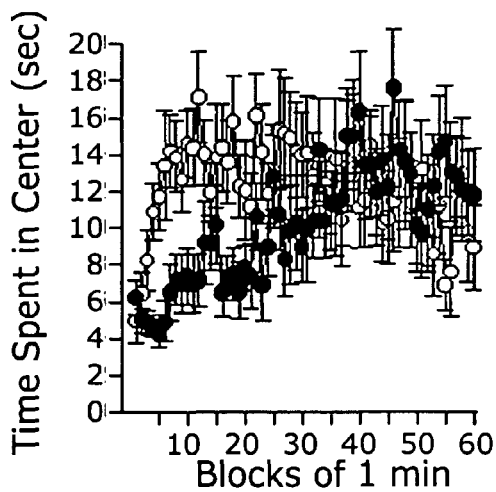
FIG. 1G compares the amount of time spent in the central region by wild type and mutant mice in the open field test.

Decreased social interaction and increased anxiety-like behavior. CN mutants spent significantly less time in the central region of the open field apparatus (FIG. 1G; $p<0.01$), which is generally considered to reflect increased anxiety [10]. In the light/dark transition test, the number of transitions between the two compartments was significantly decreased in CN mutants relative to control mice in two independent batches of subjects (FIG. 2B; $p<0.01$ for each batch of subjects), whereas the total time spent in the lit compartment was shorter in only one batch of subjects (FIG. 2C; $p<0.05$). The number of transitions is considered to be a better measure of anxiety than time spent in the lit compartment [9]. As CN mice were found to be hyperactive by several other indices of locomotor activity, the decreased number of light/dark transitions of CN mutant mice is particularly suggestive of increased fear or anxiety in CN mutant mice. In addition, despite their pronounced hyperactivity, CN mutants display a consistent, characteristic time course of locomotor activity, in which they are less active than control mice during the initial one or two minutes of the open field test (FIG. 1B), the first object exploration trial (FIG. 1A) and the social interaction test (FIG. 2D). In light of the other two findings indicating increased anxiety-like behavior of CN mutant mice, it is probable that their lower initial activity reflects increased fearfulness towards novel stimuli/situations.

In a social interaction test, the number of social contacts of CN mutants during a 10 min period did not differ significantly from that of control mice. However, the total duration of contacts and mean duration per contact of CN mutants were significantly shorter than those of control mice (FIG. 2F; $p=0.0009$). Since locomotor activity of the CN mice was increased in this test (see above section), it is possible that their decreased duration of contacts is a consequence of increased speed. However, this possibility is unlikely for two reasons. First, the duration of the exploration of inanimate objects was increased in the object exploration test. Second, in general, increased locomotor activity alone should increase the number of contacts and the total duration of contacts, if we assume that there is no difference in their motivation to make social contacts. For example, mice lacking the M1 muscarinic acetylcholine receptor were shown to be hyperactive and, at the same time, to have increased total duration and number of contacts [27]. Therefore, it is most likely that the decreased duration of social contacts with an equivalent number of contacts reflects decreased social interaction. It is unclear whether the decreased social interaction of CN mutants is due to increased anxiety or lack of motivation to make social contacts, though the finding of increased anxiety-like behaviors observed in the light/dark transition and open field tests favors the former possibility.

Figure 3:
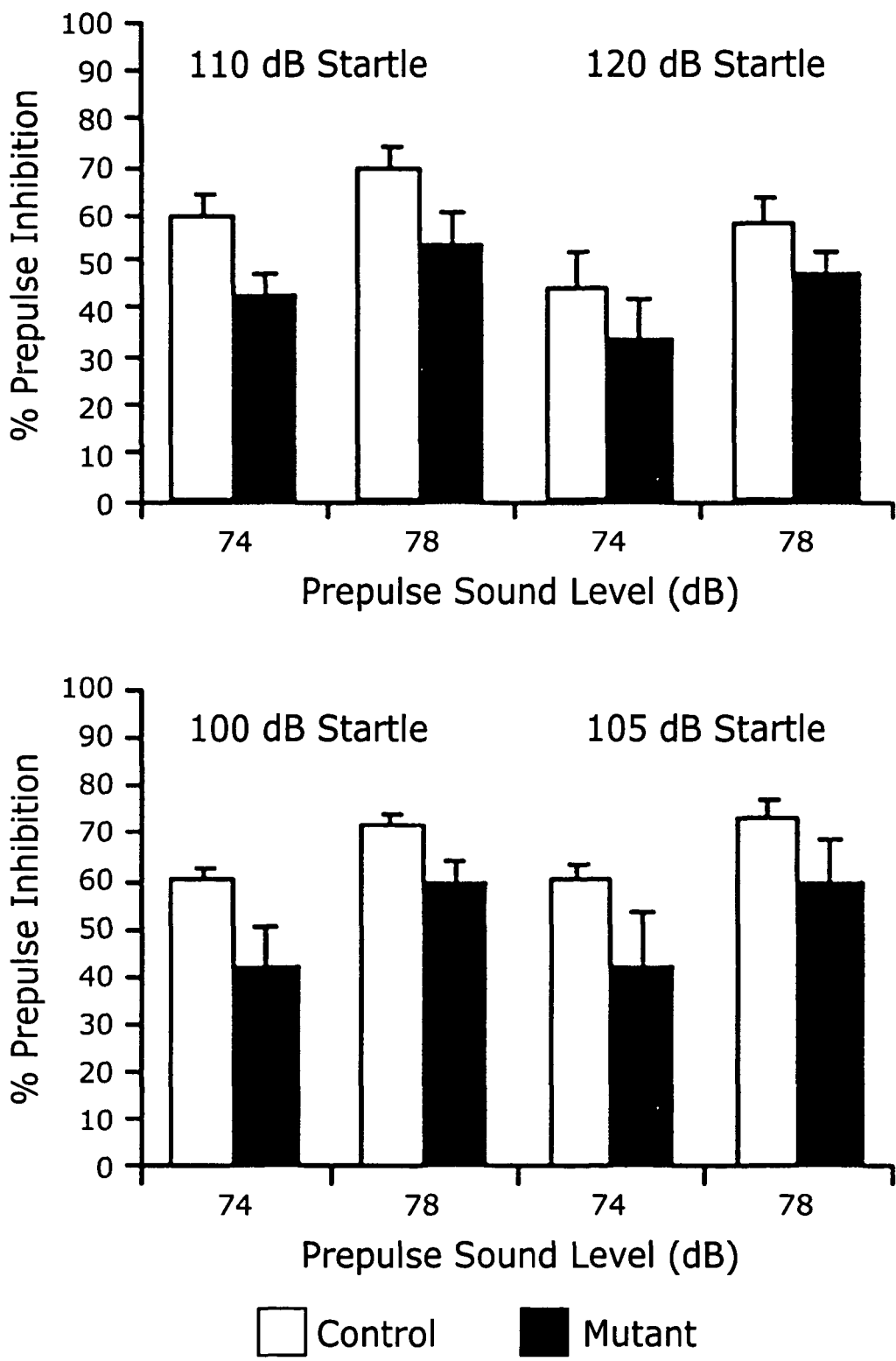
FIG. 3 compares prepulse inhibition in wild type and CNB-deficient mice at various startle stimulus intensities, showing impaired prepulse inhibition in CNB-deficient mice.

Impaired prepulse inhibition. The intensity of startle responses without prepulse was not significantly different between genotypes for stimuli of 100 dB, 105 dB, 110 dB or 120 dB. The percent prepulse inhibition, an index of sensorimotor gating, was significantly lower in CN mutants than in controls, when startle stimulus intensity was 100 dB, 105 dB and 110 dB (FIG. 3; $p=0.0023$, $p=0.0447$, $p=0.001$, respectively). When the stimulus intensity was 120 dB, a significant difference between genotypes was not observed (p=0.2610), probably because of a ceiling effect due to the strong intensity of the startle stimulus.

Figure 4:
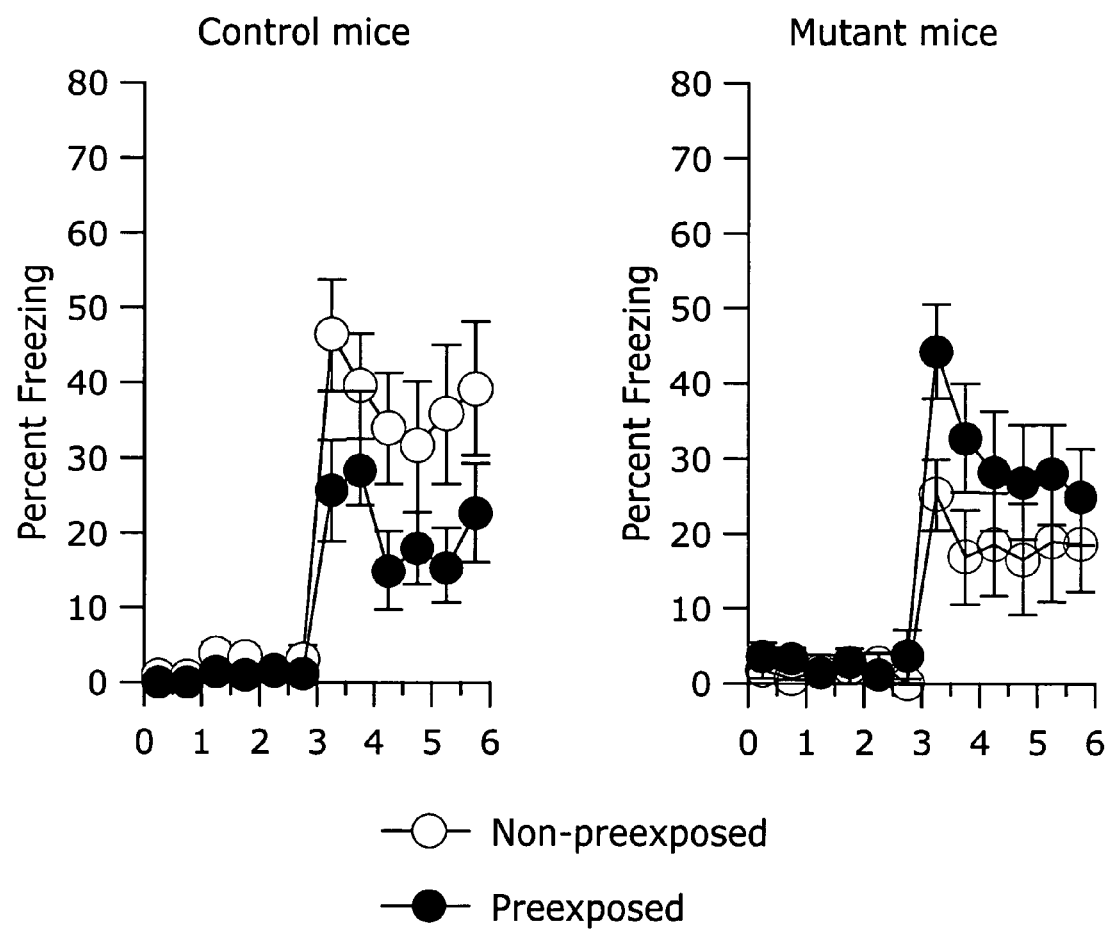
FIG. 4 compares percent freezing in wild type and CNB-deficient during the latent inhibition test, showing impaired latent inhibition in CNB-deficient mice.
Figure 5A:
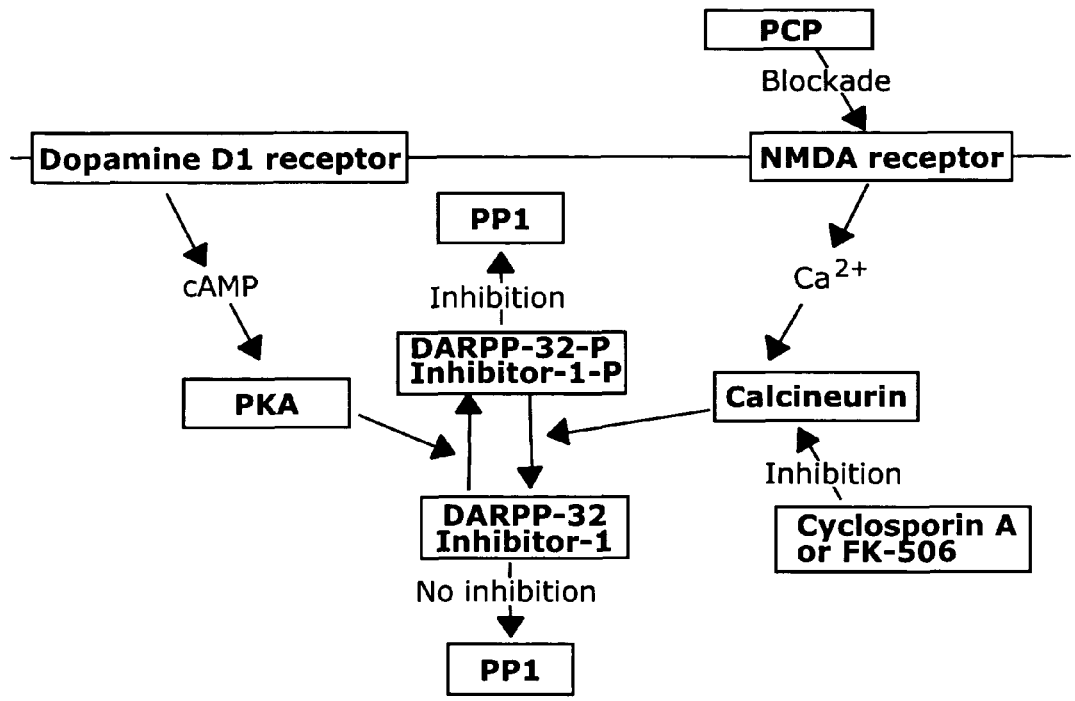
FIG. 5A: Calcineurin dephosphorylates DARPP-32 or inhibitor-1 relieving inhibition of PP1. Blockade of NMDA receptor by PCP and inhibition of calcineurin by cyclosporin A or FK-506 have been shown to cause psychosis or psychotic behavior.
Figure 5B:
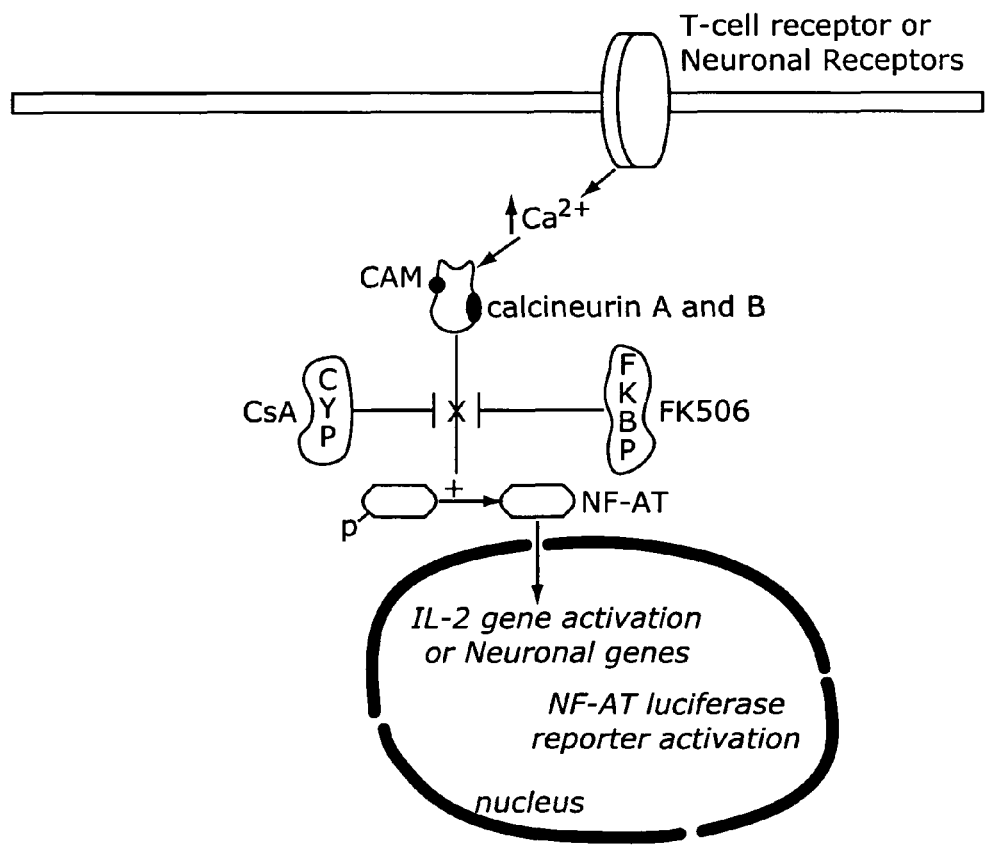
FIG. 5B: Activation of calcineurin by calcium influx leads to dephosphorylation and translocation of NF-AT to the nucleus required for activation of NF-AT mediated transcription. Modified from Snyder et al., 1998.
Figure 5C:
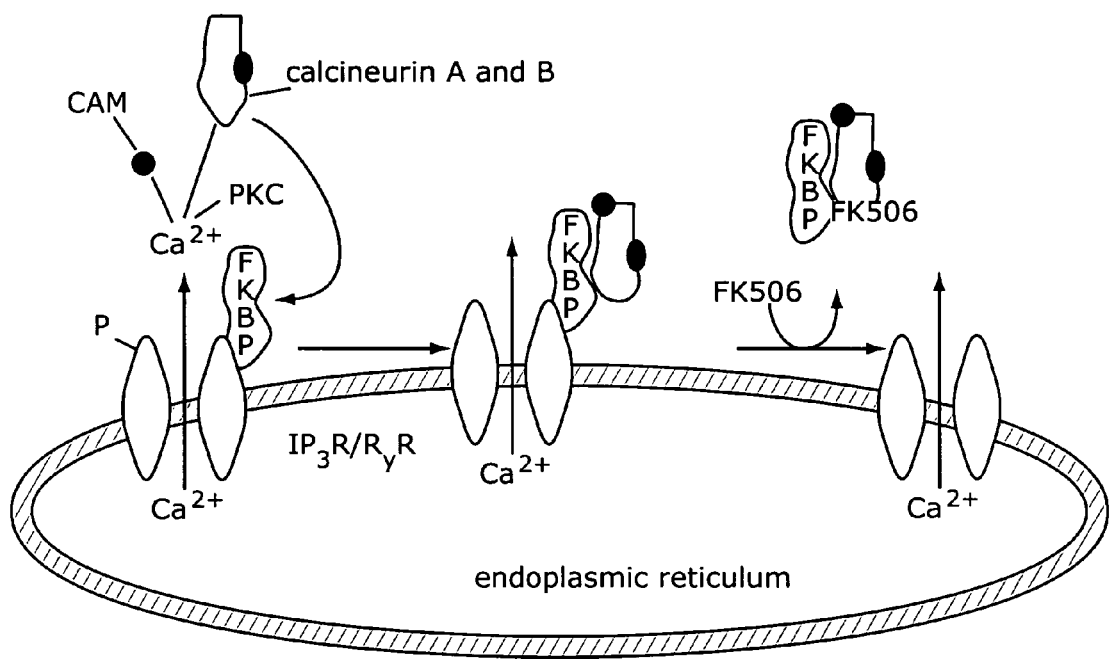
FIG. 5C: The calcium releasing channels RyR and IP3R are physically complexed with FKBP12 and calcineurin. Calcineurin modulates calcium influx through the receptors by changing the phosphorylation status of IP3R in a calcium dependent manner. Inhibition of calcineurin increases phosphorylation of IP3R and makes the IP3R/RyR more potent in releasing calcium and 'leaky'. Modified from Snyder et al., 1998.

Impaired latent inhibition. The sensitivity to electric shock as measured by distance traveled during shock presentations, percent freezing during the post-shock period of the conditioning trial and during contextual testing were not statistically different between controls and mutants for either P or NP groups. Percent immobility during the pre-shock period of the conditioning phase was significantly lower in mutant mice than in controls, probably due to their hyperactivity (data not shown). In cued testing, the percent freezing for the P group was significantly lower than that of the NP group (FIG. 4 left panel; p=0.030) in control mice, indicating significant latent inhibition in control mice. In contrast, the CN mutants failed to show a significant latent inhibition (FIG. 4 right panel).

Impaired nesting behavior. We observed that nests of CN mutants were poorly formed. Normal mice usually form a clean and identifiable nest in a distinct location in the cage. However, the CN mutants did not generally form distinguishable discrete nests and tended to scatter pieces of nesting material over the floor of the cage. Therefore, pictures of the nests were taken and the number of scattered particles of nesting material was counted for each cage. The number of particles in the cages of CN mutants was significantly larger than that of controls (Controls: 9.5±2.3, CN mutants: 18.2±3.2; p=0.037).

Example 2

Locations of Calcineurin Subunit Genes, Calcineurin Binding Protein Genes, and Genes Encoding Proteins that Interact with Calcineurin Activity are Coincident with Schizophrenia Susceptibility Loci Materials and Methods Gene location analysis. To determine the chromosomal locations of calcineurin subunit and calcineurin associated genes, the map viewer function/site of the human draft sequence (www.ncbi.nlm.nih.gov/cgi-bin/Entrez/hum_srch?chr=humchr.inf&query) was searched with query terms such as "calcineurin", and the precise chromosomal locations of the genes were retrieved. Terms describing the chromosomal positions of the genes (e.g. chromosome 8 or 8q) were combined with the term "schizophrenia", and the individual combinations were used to search the Entrez Pubmed data base (www.ncbi.nlm.nih.gov/Entrez) to retrieve publications describing schizophrenia susceptibility loci present on those chromosomes. The chromosomal positions of the schizophrenia loci were compared with those of the genes to detect coincidence. For more detailed analysis, the Human Genome Browser (genome.ucsc.edu/cgi-bin/hgGateway) or human Ensembl site (www.ensembl.org/Homo_sapiens/) were used to compare the precise gene locations with locations of markers of maximal significance for a given region of susceptibility.

Results

Locations of genes encoding calcineurin and calcineurin binding proteins. Collectively, the behavioral abnormalities observed in the CN mutants, and described in Example 1, suggested the involvement of calcineurin dysfunction in schizophrenia pathogenesis. To investigate whether mutations in calcineurin genes could contribute to schizophrenia etiology, chromosomal locations of 4 calcineurin subunit genes, PPP3R1, PPP3CA, PPP3CC and PPP3CB, and two genes encoding calcineurin binding proteins, CABIN 1 and CHP were compared with previously identified schizophrenia susceptibility loci. It was observed that the chromosomal locations of five of these genes coincide with previously mapped schizophrenia loci (Table 1).

For example, the PPP3R1 gene, which encodes the calcineurin CNB regulatory subunit, is located at 2p13.3, within a strong susceptibility locus at 2p13-14 identified in the Palauan population in Micronesia [5,7]. The PPP3CC gene, which encodes the calcineurin CNAγ catalytic subunit, is located at 8p21.3 within a major susceptibility locus at 8p21-22 [3,17,20,29]. The CABIN 1 gene, which encodes calcineurin binding protein 1, an inhibitor of calcineurin [23], is located at 22q11.3, coincident with a prominent schizophrenia susceptibility locus at 22q11 [18,34]. This region is also prone to microdeletions that confer an increased risk of schizophrenia [19]. The CHP gene, which encodes calcineurin B homologous protein [25], and which has been shown to inhibit calcineurin activity, is located at 15q15.1, coincident with a major locus at 15q15 for periodic catatonia, a clinical subtype of unsystematic schizophrenia [32].

The PPP3CA and PPP3CB genes, which encode the CNAα and β subunits, respectively, are associated with susceptibility regions of more modest significance. PPP3CA is located at 4q24 within a reported susceptibility locus at 4q13-31, characterized by one marker at 4q24 that achieves peak significance according to a core, recessive model, [17] and also in the vicinity of a susceptibility locus at 4q25 identified in two studies [21,24]. The PPP3CB gene is located at 10q22.2. While this site is not within a susceptibility region, it is in the vicinity of a suggested susceptibility region with peak significance at 10q22.3 [1].

A number of other genes encoding calcineurin binding proteins, including CS-1 (calsarcin-1) [24] [21], CS-3 (calsarcin-3) [17] [28], AKAP-5 (A kinase anchor protein 5) [12] [8] [1] and FKBP-5 (FK506 binding protein-5) [6] [35] (see Table 1) are also located within or proximal to proposed schizophrenia susceptibility loci (see Table 1).

Locations of genes encoding proteins associated with calcineurin signaling. The ryanodine receptor type three (RYR3) interacts with calcineurin and is involved with calcineurin signaling [15]. The RYR3 gene is located at 15q13.3, within a major schizophrenia susceptibility locus at 15q13-14 [34]. Interestingly, RYR3 mutant mice exhibit behavioral and electrophysiological abnormalities similar to CN mutant mice [2,14,22,33]. RYR3 associates with the IP3 receptor type 1, (IPTR1) and this complex interacts with calcineurin [15]. The IPTR1 gene is also located in the vicinity of a schizophrenia susceptibility locus mapped to 3p26.1 [29].

Members of the NFAT family of transcription factors are major substrates of CN [30]. NFAT is activated and translocated to the nucleus following dephosphorylation by CN [37 and references therein]. Interestingly, the ILF2 gene, which encodes a subunit of NFAT, is located at 1q21.3, coincident with a major schizophrenia susceptibility locus mapped to 1q21-22 [4]. Furthermore, the NFATC2 gene, which encodes a distinct calcineurin dependent NFAT subunit, is also coincident with a proposed schizophrenia susceptibility locus at 20q13 [13]. Some additional candidate molecules are listed in Table 1.

TABLE 1

Coincidence of genes encoding calcineurin subunits and calcineurin-interacting proteins with previously identified schizophrenia susceptibility loci.

| Gene name | Description | Gene location | Susceptibility | Ref. No. |
|---|---|---|---|---|
| Calcineurin Subunits | | | | |
| PPP3R1 | calcineurin B subunit | 2p13.3 | 2p13–14 | 4, 5, 25 |
| PPP3CA | calcineurin A alpha subunit | 4q24 | 4q2214 26 | 6, 7, 8, 25 |
| PPP3CC | calcineurin A gamma subunit | 8p21.3 | 8p2114 22 | 9, 6, 10, 11, 25 |
| PPP3CB | calcineurin A beta subunit | 10q21–22 | 10q22–3 | 12 |
| Calcineurin Binding Proteins | | | | |
| CABIN(=CAIN) | calcineurin binding protein 1 | 22q11.23 | 22q11 | 13, 14 |
| CHP | calcium binding protein P22 | 15q15.1/15q14 | 15q15 | 15 |
| CS-1 | calcineurin-binding protein calsarcin-1 | 4q26 | 4q25–26 | 8, 7 |
| CS-3 | calcineurin-binding protein calsarcin-3 | 5q33.2 | 5q33.2 | 6, 16 |
| AKAP5(=AKAP79) | A kinase (PRKA) anchor protein 5 | 14q23.2/14q23.3 | 14q22–24 | 17, 18, 12 |
| FKBP5 (=FKBP51) | FK506 binding protein 5; Binds to calcineurin | 6p21.31/6p21.2 | 6p21.3 | 19, 20 |
| Proteins Functionally Coupled to Calcineurin | | | | |
| ITPR1 | inositol 1,4,5-triphosphate receptor, type 1 (1P3 receptor 1) | 3p26.1 | 3p24–26 | 11 |
| RYR3 | ryanodine receptor type 3 | 15q14–15 | 15q14 | 14 |
| ILF2(=NF45) | Subunit of Nuclear Factor of Activated T-cells (NF-AT) | 1q21.3 | 1q21.3 | 21 |
| CAMLG | calcium modulating ligand | 5q31 | 5q23.3–31.1 | 25, 23, 24 |
| NFATC2 | nuclear factor of activated T-cells, cytoplasmic, calcineurin-dependent 2 | 20q13.2 | 20q13 | 22 |

REFERENCE LIST 1

References for Examples 1 and 2

[1] Bailer, U., Leisch, F., Meszaros, K., Lenzinger, E., Willinger, U., Strobl, R., Gebhardt, C., Gerhard, E., Fuchs, K., Sieghart, W., Kasper, S., Hornik, K. and Aschauer, H. N., Genome scan for susceptibility loci for schizophrenia, *Neuropsychobiology,* 42 (2000) 175-82.

[2] Balschun, D., Wolfer, D. P., Bertocchini, F., Barone, V., Conti, A., Zuschratter, W., Missiaen, L., Lipp, H. P., Frey, J. U. and Sorrentino, V., Deletion of the ryanodine receptor type 3 (RyR3) impairs forms of synaptic plasticity and spatial learning, *Embo J,* 18 (1999) 5264-73.

[3] Blouin, J. L., Dombroski, B. A., Nath, S. K., Lasseter, V. K., Wolyniec, P. S., Nestadt, G., Thornquist, M., Ullrich, G., McGrath, J., Kasch, L., Lamacz, M., Thomas, M. G., Gehrig, C., Radhakrishna, U., Snyder, S. E., Balk, K. G., Neufeld, K., Swartz, K. L., DeMarchi, N., Papadimitriou, G. N., Dikeos, D. G., Stefanis, C. N., Chakravarti, A., Childs, B., Pulver, A. E. and et al., Schizophrenia susceptibility loci on chromosomes 13q32 and 8p21, *Nat Genet,* 20 (1998) 70-3.

[4] Brzustowicz, L. M., Hodgkinson, K. A., Chow, E. W., Honer, W. G. and Bassett, A. S., Location of a major susceptibility locus for familial schizophrenia on chromosome 1q21-q22, *Science,* 288 (2000) 678-82.

[5] Camp, N. J., Neuhausen, S. L., Tiobech, J., Polloi, A., Coon, H. and Myles-Worsley, M., Genomewide multipoint linkage analysis of seven extended Palauan pedigrees with schizophrenia, by a Markov-chain Monte Carlo method, *Am J Hum Genet,* 69 (2001) 1278-89.

[6] Chowdari, K. V., Xu, K., Zhang, F., Ma, C., Li, T., Xie, B. Y., Wood, J., Trucco, M., Tsoi, W. F., Saha, N., Rudert, W. A. and Nimgaonkar, V. L., Immune related genetic polymorphisms and schizophrenia among the Chinese, *Hum Immunol,* 62 (2001) 714-24.

[7] Coon, H., Myles-Worsley, M., Tiobech, J., Hoff, M., Rosenthal, J., Bennett, P., Reimherr, F., Wender, P., Dale, P., Polloi, A. and Byerley, W., Evidence for a chromosome 2p13-14 schizophrenia susceptibility locus in families from Palau, Micronesia, *Mol Psychiatry,* 3 (1998) 521-7.

[8] Craddock, N. and Lendon, C., Chromosome Workshop: chromosomes 11, 14, and 15, *Am J Med Genet,* 88 (1999) 244-54.

[9] Crawley, J. N., Exploratory behavior models of anxiety in mice, *Neurosci Biobehav Rev,* 9 (1985) 37-44.

[10] Crawley, J. N., *What's Wrong With My Mouse? Behavioral Phenotyping of Transgenic and Knockout Mice*, John Wiley & Sons, New York, 2000.

[11] Crowe, R. R. and Vieland, V., Report of the Chromosome 5 Workshop of the Sixth World Congress on Psychiatric Genetics, *Am J Med Genet,* 88 (1999) 229-32.

[12] Faraone, S. V., Matise, T., Svrakic, D., Pepple, J., Malaspina, D., Suarez, B., Hampe, C., Zambuto, C. T., Schmitt, K., Meyer, J., Markel, P., Lee, H., Harkavy Friedman, J., Kaufmann, C., Cloninger, C. R. and Tsuang, M. T., Genome scan of European-American schizophrenia pedigrees: results of the NIMH Genetics Initiative and Millennium Consortium, *Am J Med Genet,* 81 (1998) 290-5.

[13] Freedman, R., Leonard, S., Olincy, A., Kaufmann, C. A., Malaspina, D., Cloninger, C. R., Svrakic, D., Faraone, S. V. and Tsuang, M. T., Evidence for the multigenic inheritance of schizophrenia, *Am J Med Genet,* 105 (2001) 794-800.

[14] Futatsugi, A., Kato, K., Ogura, H., Li, S. T., Nagata, E., Kuwajima, G., Tanaka, K., Itohara, S. and Mikoshiba, K., Facilitation of NMDAR-independent LTP and spatial learning in mutant mice lacking ryanodine receptor type 3, *Neuron,* 24 (1999) 701-13.

[15] Genazzani, A. A., Carafoli, E. and Guerini, D., Calcineurin controls inositol 1,4,5-trisphosphate type 1 receptor expression in neurons, *Proc Natl Acad Sci USA,* 96 (1999) 5797-801.

[16] Goodman, A. B., Elevated risks for amyotrophic lateral sclerosis and blood disorders in Ashkenazi schizophrenic pedigrees suggest new candidate genes in schizophrenia, *Am J Med Genet*, 54 (1994) 271-8.

[17] Gurling, H. M., Kalsi, G., Brynjolfson, J., Sigmundsson, T., Sherrington, R., Mankoo, B. S., Read, T., Murphy, P., Blayeri, E., McQuillin, A., Petursson, H. and Curtis, D., Genomewide genetic linkage analysis confirms the presence of susceptibility loci for schizophrenia, on chromosomes 1q32.2, 5q33.2, and 8p21-22 and provides support for linkage to schizophrenia, on chromosomes 11q23.3-24 and 20q12.1-11.23, *Am J Hum Genet*, 68 (2001) 661-73.

[18] Karayiorgou, M. and Gogos, J. A., A turning point in schizophrenia genetics, *Neuron*, 19 (1997) 967-79.

[19] Karayiorgou, M., Morris, M. A., Morrow, B., Shprintzen, R. J., Goldberg, R., Borrow, J., Gos, A., Nestadt, G., Wolyniec, P. S., Lasseter, V. K. and et al., Schizophrenia susceptibility associated with interstitial deletions of chromosome 22q11, *Proc Natl Acad Sci USA*, 92 (1995) 7612-6.

[20] Kendler, K. S., MacLean, C. J., O'Neill, F. A., Burke, J., Murphy, B., Duke, F., Shinkwin, R., Easter, S. M., Webb, B. T., Zhang, J., Walsh, D. and Straub, R. E., Evidence for a schizophrenia vulnerability locus on chromosome 8p in the Irish Study of High-Density Schizophrenia Families, *Am J Psychiatry*, 153 (1996) 1534-40.

[21] Kennedy, J. L., Basile, V. S. and Macciardi, F. M., Chromosome 4 Workshop Summary: Sixth World Congress on Psychiatric Genetics, Bonn, Germany, Oct. 6-10, 1998, *Am J Med Genet*, 88 (1999) 224-8.

[22] Kouzu, Y., Moriya, T., Takeshima, H., Yoshioka, T. and Shibata, S., Mutant mice lacking ryanodine receptor type 3 exhibit deficits of contextual fear conditioning and activation of calcium/calmodulin-dependent protein kinase II in the hippocampus, *Brain Res Mol Brain Res*, 76 (2000) 142-50.

[23] Lai, M. M., Burnett, P. E., Wolosker, H., Blackshaw, S. and Snyder, S. H., Cain, a novel physiologic protein inhibitor of calcineurin, *J Biol Chem*, 273 (1998) 18325-31.

[24] Levinson, D. F., Mahtani, M. M., Nancarrow, D. J., Brown, D. M., Kruglyak, L., Kirby, A., Hayward, N. K., Crowe, R. R., Andreasen, N. C., Black, D. W., Silverman, J. M., Endicott, J., Sharpe, L., Mohs, R. C., Siever, L. J., Walters, M. K., Lennon, D. P., Jones, H. L., Nertney, D. A., Daly, M. J., Gladis, M. and Mowry, B. J., Genome scan of schizophrenia, *Am J Psychiatry*, 155 (1998) 741-50.

[25] Lin, X., Sikkink, R. A., Rusnak, F. and Barber, D. L., Inhibition of calcineurin phosphatase activity by a calcineurin B homologous protein, *J Biol Chem*, 274 (1999) 36125-31.

[26] McInnes, L. A., Service, S. K., Reus, V. I., Barnes, G., Charlat, O., Jawahar, S., Lewitzky, S., Yang, Q., Duong, Q., Spesny, M., Araya, C., Araya, X., Gallegos, A., Meza, L., Molina, J., Ramirez, R., Mendez, R., Silva, S., Fournier, E., Batki, S. L., Mathews, C. A., Neylan, T., Glatt, C. E., Escamilla, M. A., Luo, D., Gajiwala, P., Song, T., Crook, S., Nguyen, J. B., Roche, E., Meyer, J. M., Leon, P., Sandkuijl, L. A., Freimer, N. B. and Chen, H., Fine-scale mapping of a locus for severe bipolar mood disorder on chromosome 18p 11.3 in the Costa Rican population, *Proc Natl Acad Sci USA*, 98 (2001) 11485-90.

[27] Miyakawa, T., Yamada, M., Duttaroy, A. and Wess, J., Hyperactivity and intact hippocampus-dependent learning in mice lacking the M1 muscarinic acetylcholine receptor, *J Neurosci*, 21 (2001) 5239-50.

[28] Paunio, T., Ekelund, J., Varilo, T., Parker, A., Hovatta, I., Turunen, J. A., Rinard, K., Foti, A., Terwilliger, J. D., Juvonen, H., Suvisaari, J., Arajarvi, R., Suokas, J., Partonen, T., Lonnqvist, J., Meyer, J. and Peltonen, L., Genome-wide scan in a nationwide study sample of schizophrenia families in Finland reveals susceptibility loci on chromosomes 2q and 5q, *Hum Mol Genet*, 10 (2001) 3037-48.

[28] Pulver, A. E., Lasseter, V. K., Kasch, L., Wolyniec, P., Nestadt, G., Blouin, J. L., Kimberland, M., Babb, R., Vourlis, S., Chen, H. and et al., Schizophrenia: a genome scan targets chromosomes 3p and 8p as potential sites of susceptibility genes, *Am J Med Genet*, 60 (1995) 252-60.

[30] Snyder, S. H., Lai, M. M. and Burnett, P. E., Immunophilins in the nervous system, *Neuron*, 21 (1998) 283-94.

[31] Snyder, S. H., Sabatini, D. M., Lai, M. M., Steiner, J. P., Hamilton, G. S. and Suzdak, P. D., Neural actions of immunophilin ligands, *Trends Pharmacol Sci*, 19 (1998) 21-6.

[32] Stober, G., Saar, K., Ruschendorf, F., Meyer, J., Nurnberg, G., Jatzke, S., Franzek, E., Reis, A., Lesch, K. P., Wienker, T. F. and Beckmann, H., Splitting schizophrenia: periodic catatonia-susceptibility locus on chromosome 15q15, *Am J Hum Genet*, 67 (2000) 1201-7.

[33] Takeshima, H., Ikemoto, T., Nishi, M., Nishiyama, N., Shimuta, M., Sugitani, Y., Kuno, J., Saito, I., Saito, H., Endo, M., Iino, M. and Noda, T., Generation and characterization of mutant mice lacking ryanodine receptor type 3, *J Biol Chem*, 271 (1996) 19649-52.

[34] Thaker, G. K. and Carpenter, W. T., Jr., Advances in schizophrenia, *Nat Med*, 7 (2001) 667-71.

[35] Wright, P., Donaldson, P. T., Underhill, J. A., Choudhuri, K., Doherty, D. G. and Murray, R. M., Genetic association of the HLA DRB1 gene locus on chromosome 6p21.3 with schizophrenia, *Am J Psychiatry*, 153 (1996) 1530-3.

[36] Zeng, H., Chattaji, S., Barbarosie, M., Rondi-Reig, L., Philpot, B. D., Miyakawa, T., Bear, M. F. and Tonegawa, S., Forebrain-specific calcineurin knockout selectively impairs bidirectional synaptic plasticity and working/episodic-like memory, *Cell*, 107 (2001) 617-29.

[37] Li, H. and Stark, G., NFκB-dependent signaling pathways, *Exp. Hematol.*, 30 (2002) 285-296.

Example 3

Sequence Analysis of Genes Encoding Calcineurin Subunits and Proteins Associated with Calcineurin Signaling in Schizophrenia Patients Materials and Methods Patient samples. The United States and South African patient samples utilized in this study have been previously described [1, 2]. Detailed information about the adult schizophrenic (AS) sample is provided in Sobin, C., Blundell, M. L., Conry, A., Weiller, F., Gavigan, C., Haiman, C. & Karayiorgou, M. (2001) *Psychiatry Res.* 101, 101-113. The South African sample is part of our ongoing collection of schizophrenia patients of Afrikaner origin and will be described in detail elsewhere (M. K., M. Torrington, C. S., B. R., S. C. H., M. L. B., H. Pretorius, S. Lay, J. A. G., and J. L. R., unpublished work). Probands in both samples met lifetime criteria for Diagnostic and Statistical Manual of Mental Disorders, 4th Ed. (DSM-IV) (American Psychiatric Association. (1994) *Diagnostic and Statistical Manual* (Am. Psychiatric Assoc., Washington, D.C.)) schizophrenia or schizoaffective disorder. Participants were interviewed by specially trained clinicians by using the Diagnostic Interview for Genetic Studies (DIGS) (Nurnberger, J. I., et al. (1994) *Arch. Gen. Psychiatry* 51, 849-859). Detailed information about the COS sample is provided in Usiskin, S. I., et al. (1999) *J. Am. Acad.*

Child Adolesc. Psychiatry 38, 1536-1543 and Nicolson, R., et al. (2000) Am. J Psychiatry 157, 794-800. All COS probands met unmodified criteria for schizophrenia with onset of psychotic symptoms before their 13th birthday and mean age of onset of psychosis at 10.1 (±1.8 yr). The protocol and the consent forms were approved by the Institutional Review Boards (IRBs) at all participating sites. The National Institute of Mental Health (NIMH) samples have been obtained from the NIMH Human Genetics Initiative dataset (zork.wustl.edu/nimh).

PCR/sequencing. PCR primers were designed to amplify genomic fragments spanning exon sequence including coding and non-coding exons, promoter sequence and some intron sequence. (For primer sequences, see Appendix 1.) The human draft sequence available at the UCSC working human draft site, genome.ucsc.edu/ was used for all primer design. Each PCR primer pair consisted of a forward and reverse primer designed to amplify a specific genomic fragment. Forward PCR primers contained 19-21 by of homologous sequence fused on the 5' end to an 18 by forward universal sequencing tag: 5'-TGTAAAACGACGGCCAGT-3' (SEQ ID NO: 1). Reverse PCR primers contained 19-21 by of homologous sequence fused on the 5' end to an 18 by reverse universal sequencing tag: 5'-CAGGAAACAGCTATGACC-3' (SEQ ID NO: 2). This allowed all PCR fragments to be sequenced in both directions, using these two primers to prime all sequencing reactions. PCR reactions were performed using a programmable PCR tetrad machine (MJ Research, Cambridge Mass.). The majority of reactions were performed using OptiPrime 10×PCR buffer 6 (Stratagene, La Jolla, Calif.). Specific sequences were amplified in a 25 ul reaction mixture containing 20 ng genomic DNA, each primer at 400 nM concentration, each dNTP at 200 uM concentration and 1.5 U Taq polymerase (Sigma Chemical Co., St. Louis, Mo.) in appropriate OptiPrime buffer conditions. PCR amplification was as follows: an initial denaturation step at 94° C. for 5 min, followed by 34 amplification cycles: 45 sec at 94° C.; 60 sec at appropriate annealing temperature (usually 62.5° C.): 60 sec elongation at 72° C., followed by a final extension step at 72° C. for 7 min. GC rich fragments were amplified using Advantage GC genomic polymerase mix (Becton Dickenson, Palo Alto, Calif.) in reactions of 25 ul containing 1M GC melt, and 400 nM primer concentration, according to the manufacturer's instructions. GC rich PCR amplification was as follows: an initial denaturation step at 95° C. for 1 min followed by 34 amplification cycles of: 94° C. for 30 sec, 68° C. for 3 min, followed by a final extension step at 68° C. for 7 min. PCR fragments were separated by 2% agarose gel electrophoresis, and purified using the Qiagen Minelute Gel extraction kit (Qiagen, Valencia, Calif.). All sequencing reactions were performed by ACGT Inc. (Northbrook, Ill.).

Sequence analysis. Sequence analysis was performed using DNAStar software. Patient sequences were compared with the human genome draft sequence, available at the UCSC website, genome.ucsc.edu. Contigs including the patient sequences and the human draft sequence were constructed for each fragment, and polymorphisms were identified by comparison.

Genotyping. Polymorphisms used for genotyping were either identified by direct sequencing, or found in SNP databases including the UCSC working human draft site, genome.ucsc.edu or the Weizmann Institute Gene Cards site, bioinfo.weizmann.ac.il/cards/index.html which both link to the NCBI SNP database, www.ncbi.nlm.nih.gov/SNPl; and the Celera database at www.celera.com/. Insertion/deletion polymorphisms were typed by PCR of genomic DNA from individual subjects and identified by altered fragment size as assessed by agarose gel electrophoresis. Single nucleotide polymorphisms (SNPs) that altered restriction endonuclease sites were typed using PCR-Restriction Fragment Length Polymorphism Genotyping [1, 2]. Briefly a fragment spanning the SNP was amplified by PCR from genomic DNA of individual subjects and 10 ul of the PCR product was digested with the relevant restriction enzyme in a 15 ul reaction according to the manufacturer's specifications (New England Biolabs, Beverly, Mass.). Digested products were subjected to 4% agarose gel electrophoresis, visualized by ethidium bromide staining, and photographed with an Eagle Eye apparatus (Stratagene, La Jolla, Calif.). SNPs that do not alter restriction sites were genotyped using fluorescence polarization template-directed dye-terminator incorporation (FP-TDI) genotyping as described in publications referenced in [1, 2] and specifically mentioned above.

Results

To identify potential functional polymorphisms in six genes that could contribute to schizophrenia susceptibility (genes encoding either calcineurin subunits or other proteins associated with calcineurin signaling), as well as polymorphisms that could be used for association studies, we determined the sequence of coding and non-coding exons and some of the promoter region for these genes in genomic DNA isolated from 12 independent schizophrenia patients. The selected genes were: PPP3R1, PPP3CA, PPP3CB, PPP3CC, CAMLG, and FKBP 5. Data presented herein relate to analysis of the first 3 of these genes.

The sequencing strategy consisted of PCR amplification of fragments covering the regions to be sequenced, followed by sequencing of these fragments. PCR primers (Appendix 1) were designed to amplify fragments spanning exon sequence and some promoter sequence from patient genomic DNA, and were tagged with universal sequencing primers so that all fragments could be sequenced in forward and reverse directions with the same two primers. Exon fragments contained at least 100 bp of flanking intron sequence on each side to cover splice donor and recipient sites and in some cases, putative branch sites. The obtained sequence was compared with the human draft sequence to identify polymorphisms.

Identified polymorphisms, and the patient genotypes are listed in Table 2. Each polymorphism is assigned an ID containing an abbreviation indicating the particular gene in which the polymorphism occurs and a number to identify which polymorphism within that gene is being referred to. Abbreviations are as follows: R1=PPP3R1 gene; CA=PPP3CA; CB=PPP3CB; CC=PPP3CC; CG=CAMLG; FK=FKBP 5. For example, an ID of R1-15 indicates that the polymorphism occurs in the PPP3R1 gene and is identified as number 15. The 12 patients are assigned an ID number. A + in the genotype listed under each patient ID indicates that the patient displayed the polymorphism while a − indicates that the patient displayed the wild type (reference) sequence at the polymorphic site. For example, a genotype of ++ indicates that both alleles of the indicated gene displayed the polymorphism.

Sequences of the identified polymorphisms are provided in Appendix 2. In Appendices 2 and 4, the upper case letters that are red are exonic sequence. The black lower case letters are intronic sequence. The sites of the polymorphisms are bolded, colored and underlined, and the reference to them or identification of them in the margin, e.g., SNP A/G is in the same color as the site. The blue and green sequences are the amplification primers.

Nineteen polymorphisms were identified in the PPP3R1 gene. Only one of these, R1-14, is situated in the coding sequence and it does not create a change in the amino acid sequence. Twelve polymorphisms were found in the PPP3CA gene. Two of these, CA-2 and CA-9, are situated in the coding sequence, but neither creates a change in the amino acid sequence. Four polymorphisms were identified in the PPP3CB gene, none of which are in the coding sequence.

Sixteen polymorphisms were found in the PPP3CC gene. One of these, CC-5, is situated in exon 5 and results in a non-conservative change in the amino acid sequence of the encoded protein from a charged arginine residue at position 163 to a neutral glutamine residue. The CC-5 polymorphism was found only in patient 15 among 12 patients. Since it creates a non-conservative amino acid change, it may represent a relatively rare functional mutation. Six polymorphisms were identified in the CAMLG gene. One of these, CG-2 is situated in the coding sequence and results in a conservative change from a valine to an isoleucine residue at position 78 of the protein. Further analysis found the CC-5 polymorphism in three of 210 tested patients and in none of 75 unaffected controls from the Coriell Cell Repository (the significance of this finding is unknown, since patient and control groups are not perfectly matched). Four polymorphisms were found in the FKBP 5 gene, none of which alter the coding sequence.

TABLE 2

Polymorphisms identified from sequencing

| ID number | Description and location of polymorphisms | Gene | Primer ID |
|---|---|---|---|
| R1-1 | 29BP Insertion(329;GCCGGCCCGCGCGCGCCCCCGCCTCCGCC, 100 bases before Exon1) | PPP3R1 | R1-P1 |
| R1-2 | SNP (373;A -> G; promoter) | PPP3R1 | R1-P1 |
| R1-3 | SNP (408; T -> C; before Exon1, Non-CDS) | PPP3R1 | R1-P1 |
| R1-4 | SNP (24; C -> T; Exon1; Non-CDS) | PPP3R1 | R1-01 |
| R1-5 | Insertion (59; A; Intron after Exon1) | PPP3R1 | R1-16 |
| R1-6 | SNP (130; T -> A; Intron after Exon2) | PPP3R1 | R1-14 |
| R1-7 | SNP (314; T -> C; Intron after Exon2) | PPP3R1 | R1-14 |
| R1-8 | TTTT -> AAAA (350; Intron after Exon2) | PPP3R1 | R1-14 |
| R1-9 | TTTT -> TTTA (350; Intron after Exon2) | PPP3R1 | R1-14 |
| R1-10 | TTTT -> TTAA (350; Intron after Exon2) | PPP3R1 | R1-14 |
| R1-11 | SNP (363; A -> T; Intron after Exon2) | PPP3R1 | R1-14 |
| R1-12 | SNP (329; G -> C; Intron after Exon2) | PPP3R1 | R1-15(F) |
| R1-13 | SNP (333; T -> C; Intron after Exon2) | PPP3R1 | R1-15(F) |
| R1-14 | SNP (311; C -> T; Exon3; CDS; No Amino acid change; Lin et al., 1994) | PPP3R1 | R1-05(F)/R1-06(F) |
| R1-15 | SNP (55; T -> G; Intron after Exon3) | PPP3R1 | R1-06 ® |
| R1-16 | Insertion of TTAA (550, Intron after Exon5) | PPP3R1 | R1-08 |
| R1-17 | SNP (49; G -> A; Intron befor Exon 6; P30 (hetero)) | PPP3R1 | R1-10 |
| R1-18 | SNP (370; T -> C; Exon 6; After STOP codon) | PPP3R1 | R1-10 |
| R1-19 | SNP (315; A -> G; 3' untranslated) PPP3R1 | R1-12 | |
| CA-1 | SNP (316; G -> C; Intron after Exon1 | PPP3CA | CA-01c(F) |
| CA-2 | SNP (293; C -> G; Exon1, CDS, No amino acid change) | PPP3CA | CA-01c ® |
| CA-3 | SNP (354, 355; TT -> CG; Intron after Exon1) | PPP3CA | CA-01c ® |
| CA-4 | SNP (206; G -> A; Intron after Exon1; P5) | PPP3CA | CA-02 |
| CA-5 | SNP (99; G -> A; Intron before Exon4) | PPP3CA | CA-05 |
| CA-6 | SNP (545; T -> C; Intron before Exon2) | PPP3CA | CA-18 |
| CA-7 | TTTT -> TTAA (350; Intron after Exon2) | PPP3CA | CA-25 |
| CA-8 | SNP (415; A -> C; Intron after Exon3) | PPP3CA | CA-25 |
| CA-9 | SNP (187; G -> C; Exon10, CDS, No amino acid change) | PPP3CA | CA-11 |
| CA-10 | SNP (289; C -> A; Intron after Exon12) | PPP3CA | CA-13 |
| CA-11 | SNP (330; G -> A; Intron after Exon12) | PPP3CA | CA-13 |
| CA-12 | SNP (58; A -> G; Exon14 after STOP) | PPP3CA | CA-26 ® |
| CB-1 | SNP (209; C -> T; Promoter region before Exon 1) | PPP3CB | CB-19 |
| CB-2 | SNP (19; C -> T; Intron after Exon5) | PPP3CB | CB-05 |
| CB-3 | SNP (152; G -> A; intron 3, just before exon 4) | PPP3CB | CB-21 |
| CB-4 | SNP (461; G -> A; Exon14 after STOP) | PPP3CB | CB-17 |
| CC-1 | SNP (100; C -> T; promoter 10BP before Exon1) | PPP3CC | CC-1a |
| CC-2 | SNP (100; C -> A; promoter 10BP before Exon1) | PPP3CC | CC-1a |
| CC-3 | SNP (130; C -> A; Exon1 before start) | PPP3CC | CC-1a |
| CC-4 | SNP (312; A -> G; Exon 1 5' UTR) | PPP3CC | CC-1a |
| CC-5 | SNP (234; G -> A; Exon5; CDS; Amino acid change(Arg -> Gln) PPP3CC | CC-19 | |
| CC-6 | SNP (315; C -> G; Intron after Exon9) | PPP3CC | CC-20 |
| CC-7 | Deletion(TTTTAGTTG; 340; Intron after Exon10) | PPP3CC | CC-10 |
| CC-8 | SNP (398; G -> C; Intron after Exon10) | PPP3CC | CC-10 |
| CC-9 | SNP (99; T -> A; Intron before Exon11) | PPP3CC | CC-11 |
| CC-10 | SNP (325; T -> G; Intron after Exon11) | PPP3CC | CC-11 |
| CC-11 | SNP (92; T -> C; Intron before Exon12) | PPP3CC | CC-12 |
| CC-12 | SNP (413; G -> C; Exon13 after STOP; Non-CDS) | PPP3CC | CC-13 |
| CC-13 | SNP (152; G -> A; Exon13 after STOP; Non-CDS) | PPP3CC | CC-14 |
| CC-14 | SNP (257; G -> A; Promotor) | PPP3CC | CC-50 |
| CC-15 | SNP (368; T -> G; Promotor) | PPP3CC | CC-50 |
| CC-16 | SNP (392; G -> A; Promotor) | PPP3CC | CC-50 |
| CG-1 | SNP (333; G -> C; Intron before exon 2) | CAMLG | CLG-10 |
| CG-2 | SNP (163; G -> A; Exon2; CDS; Amino acid change(Val -> Ile) | CAMLG | CLG-02 |

TABLE 2-continued

Polymorphisms identified from sequencing

| | | | | |
|---|---|---|---|---|
| CG-3 | SNP (273; C –> A; Intron after exon 2) | | CAMLG | CLG-11 |
| CG-4 | SNP (193; G –> A; Intron before exon 3) | | CAMLG | CLG-12 |
| CG-5 | TTTT –> TTAA (350; Intron after Exon2) | | CAMLG | CLG-12 |
| CG-6 | SNP (269; C –> A; Exon4 after STOP) | | CAMLG | CLG-06 ® |
| FK-1 | SNP (214; A –> G; Intron after Exon1) | | FK-501 | FK-01 |
| FK-2 | SNP (346; G –> A; Intron after Exon1) | | FK-501 | FK-01 |
| FK-3 | SNP (390; G –> T; Intron after Exon2) | | FK-501 | FK-02 |
| FK-4 | SNP (144; G –> T; Exon11) | | FK-501 | FK-14 |
| ? denotes sequence that needs to be confirmed | | | | |

| ID number | P5 | P10 | P15 | P18 | P19 | P29 | P30 | P38 | P41 | P72 | P78 | P53 |
|---|---|---|---|---|---|---|---|---|---|---|---|---|
| R1-1 | ++ | +- | +- | +- | -- | +- | +- | +- | ++ | +- | ++ | ++ |
| R1-2 | -- | -- | -- | -- | -- | -- | -- | -- | -- | -- | +- | -- |
| R1-3 | ++ | +- | +- | +- | -- | +- | +- | +- | ++ | +- | ++ | ++ |
| R1-4 | +- | +- | -- | -- | -- | +- | +- | +- | +- | +- | +- | +- |
| R1-5 | +-? | +-? | +-? | +- | -- | +- | +- | -- | ++ | nd | +-? | +-? |
| R1-6 | ++ | +- | ++ | +- | -- | +- | +- | +- | ++ | +- | ++ | ++ |
| R1-7 | ++ | +- | ++ | +- | -- | +- | +- | +- | ++ | +- | ++ | ++ |
| R1-8 | +- | ++? | -- | +- | -- | +- | +- | -- | ++ | +-? | +-? | +-? |
| R1-9 | +- | -- | +- | -- | -- | -- | -- | +- | -- | -- | nd | nd |
| R1-10 | -- | -- | +- | -- | -- | -- | -- | -- | -- | -- | +-? | +-? |
| R1-11 | ++ | +- | ++ | +- | -- | +- | +- | +- | ++ | +- | ++ | ++ |
| R1-12 | ++ | +- | ++ | +- | -- | +- | +- | +- | ++ | +- | ++ | ++ |
| R1-13 | ++ | +- | ++ | +- | -- | +- | +- | +- | ++ | +- | ++ | ++ |
| R1-14 | -+ | +- | -- | +- | -- | +- | +- | -- | ++ | +- | +- | +- |
| R1-15 | -- | -- | -- | -- | +- | -- | -- | -- | -- | -- | -- | -- |
| R1-16 | ++ | +-? | ++ | +-? | -- | +-? | +-? | +-? | ++ | +-? | ++ | ++ |
| R1-17 | -- | -- | -- | -- | -- | +- | -- | -- | -- | -- | -- | -- |
| R1-18 | -- | +- | -- | +- | -- | +- | +- | -- | +- | -- | +- | +- |
| R1-19 | -- | -- | -- | -- | -- | -- | -- | -- | -- | -- | +- | -- |
| CA-1 | -- | -- | -- | -- | -- | -- | -- | -- | -- | -- | +-? | -- |
| CA-2 | -- | -- | -- | -- | -- | -- | -- | -- | -- | -- | +-? | -- |
| CA-3 | ++ | +- | +- | +- | ++ | +- | ++ | +- | ++ | ++ | -- | +- |
| CA-4 | +- | -- | -- | +- | -- | -- | -- | -- | -- | -- | -- | -- |
| CA-5 | -- | -- | -- | -- | -- | -- | +- | -- | -- | -- | -- | +- |
| CA-6 | +- | -- | -- | -- | -- | +- | -- | -- | +- | -- | -- | -- |
| CA-7 | -- | -- | -- | -- | -- | -- | -- | -- | -- | -- | +- | -- |
| CA-8 | +- | -- | +- | ++ | -- | +- | -- | +- | -- | +- | ?nd | +- |
| CA-9 | +- | -- | -- | -- | -- | -- | -- | -- | -- | -- | -- | -- |
| CA-10 | -- | -- | -- | +- | -- | -- | -- | -- | -- | -- | -- | -- |
| CA-11 | -- | ++ | ++ | +- | ++ | ++ | +- | +- | ++ | +- | +- | ++ |
| CA-12 | -- | -- | +-? | -- | -- | -- | -- | -- | -- | -- | -- | +-? |
| CB-1 | -- | -- | -- | -- | -- | +- | -- | -- | -- | -- | -- | -- |
| CB-2 | -- | -- | -- | -- | -- | -- | +- | -- | -- | -- | -- | -- |
| CB-3 | -- | -- | +- | -- | -- | +- | +- | -- | -- | -- | -- | -- |
| CB-4 | -- | -- | +- | -- | -- | +- | +- | -- | +- | -- | -- | -- |
| CC-1 | -- | -- | -- | -- | -- | +- | +- | -- | -- | -- | +- | +- |
| CC-2 | -- | -- | +- | -- | -- | -- | -- | -- | -- | -- | -- | -- |
| CC-3 | -- | -- | -- | +- | +- | ++ | +- | -- | -- | -- | ++ | +- |
| CC-4 | -- | -- | +- | -- | -- | -- | -- | -- | -- | -- | -- | -- |
| CC-5 | -- | -- | +- | -- | -- | -- | -- | -- | -- | -- | -- | -- |
| CC-6 | -- | +-? | -- | -- | -- | -- | -- | -- | -- | -- | -- | -- |
| CC-7 | -- | -- | +- | -- | -- | -- | -- | -- | -- | -- | -- | -- |
| CC-8 | -- | -- | -- | -- | -- | -- | -- | -- | +- | -- | -- | -- |
| CC-9 | -- | -- | +- | -- | -- | -- | -- | -- | -- | -- | -- | -- |
| CC-10 | +- | -- | ++ | +- | +- | -- | ++ | +- | -- | +- | ++ | +- |
| CC-11 | +- | -- | +- | -- | -- | -- | -- | -- | -- | -- | -- | -- |
| CC-12 | +- | -- | ++ | +- | +- | -- | ++ | +- | -- | +- | ++ | +- |
| CC-13 | -- | -- | ++ | +- | +- | -- | ++ | +- | -- | +- | ++ | +- |
| CC-14 | -- | ++ | -- | -- | -- | -- | nd | nd | nd | nd | nd | nd |
| CC-15 | -- | nd | +- | -- | nd | -- | nd | nd | nd | nd | nd | nd |
| CC-16 | -- | nd | +- | -- | nd | -- | nd | nd | nd | nd | nd | nd |
| CG-1 | -- | -- | -- | -- | -- | -- | -- | -- | -- | -- | -- | -- |
| CG-2 | -- | -- | -- | +- | -- | -- | -- | -- | +- | -- | -- | -- |
| CG-3 | -- | -- | -- | +- | -- | -- | -- | -- | +- | -- | -- | -- |
| CG-4 | -- | -- | -- | -- | -- | -- | -- | +- | -- | -- | -- | -- |
| CG-5 | -- | -- | -- | -- | +-? | -- | -- | -- | -- | -- | -- | -- |
| CG-6 | -- | -- | +-? | -- | -- | -- | -- | -- | -- | -- | -- | -- |
| FK-1 | +- | ++ | +- | +- | ++ | ++ | ++ | ++ | ++ | +- | +-? | ++ |
| FK-2 | -- | +- | +- | -- | +- | -- | ++ | +- | -- | +- | -- | -- |
| FK-3 | +- | ++ | +- | -- | ++ | ++ | ++ | ++ | ++ | +- | +- | ++ |
| FK-4 | +- | ++ | +- | +- | ++? | ++ | ++ | ++ | ++ | -- | +- | ++ |

Example 4

Association Studies of Calcineurin Subunits and Identification of Association Materials and Methods Association analysis. Transmissions of single SNPs, as well as multiple SNP haplotypes, were analyzed by the Transmission Disequilibrium Test using the Transmit program [3]. P values listed represent global significance levels calculated by the transmit program, described at http://www-gene.cimr.cam.ac.uk/clayton/software/transmit.txt. P values were calculated from the global chi square values obtained from the transmit program TDT analysis.

Results

To further investigate the involvement of genes encoding calcineurin subunits and calcineurin interacting proteins in schizophrenia pathogenesis, we are systematically testing for association of the candidate genes listed in Table 1 with disease in samples comprising a large number of affected families. We have currently performed initial association analysis for three of these genes, PPP3R1, PPP3CA and PPP3CC. For this study we utilized some of the polymorphisms that we identified by direct sequencing, supplemented with additional single nucleotide polymorphisms (SNPs) obtained from the NCBI or Celera databases. The polymorphisms used are listed in Table 3, the sequences of the primers used for genotyping reactions are listed in Appendix 3 and the sequence of these polymorphisms is provided in Appendix 4.

First we determined the genotypes for 210 schizophrenia triads (parents and affected proband) collected from the United States population [1, 2], with respect to all of the polymorphisms (referred to as SNPs hereafter for convenience) listed in Table 3. We then employed the transmission disequilibrium test (TDT) using the transmit program with a sliding window strategy to determine if observed transmission of any individual SNP or multiple (2, 3, 4 and 5) SNP combinations deviate from the expected value in this sample.

Results of this analysis are presented in Table 4. The data in Tables 4 and 5 considers all haplotypes having at least 3% frequency. All P values represent global significance calculated from the global chi square values obtained from the TDT analysis. For PPP3R1, significant deviation from expected transmission was not observed for any of the individual or multiple SNP combinations (all P values>0.05 TDT test, transmit program, Table 4). Similarly, for PPP3CA, significant deviation from expected transmission was not observed for any of the individual or multiple SNP combinations (all P values>0.05, Table 4). Analysis of the 3 SNP combination (CAS6, CASFP1, CASFP2) did yield a P value of 0.061, which could represent a trend towards transmission disequilibrium and association with disease for this gene. Failure to detect significant transmission disequilibrium for these genes in this study does not necessarily indicate a lack of association of these genes with schizophrenia. For example, different genes may be associated with schizophrenia in different populations, and it may be the case that studying such populations would reveal association. It may also be necessary to examine more SNPs for these genes, in order to ensure that the entire gene is represented since it is presently unclear whether all haplotype blocks are covered by the analysis to date, as would be desirable. Furthermore, examining more families might reveal association since a sample of 210 families may not have enough power to detect a weaker but significant association. In addition, some genes may be prone to a high level of mutations or genomic instability, e.g., deletions. If this is the case, the mutations might happen so frequently, and are ongoing in the human population so that they will not be associated with a particular haplotype.

For the PPP3CC gene, significant deviation from expected transmission was observed for single SNPs (CC21, P=0.038; CCS3, P=0.041) and 2 SNP (CC21,33, P=0.013; CC33, S3, P=0.003) 3 SNP (CC20,21,33, P=0.031; CC21,33, S3, P=0.024) 4 SNP (CC1a, 20,21,33, P=0.003; CC20,21,33, S3, P=0.0047) and 5 SNP (CC1a, 20,21,33, S3, P=0.016) combinations (Table 4). These results provide evidence for association of the PPP3CC gene with schizophrenia in the US population.

To further investigate the association of the PPP3CC gene with schizophrenia, we determined the genotypes with respect to all 5 PPP3CC SNPs for a sample of 200 additional families from the South African population [1,2], including a collection of triads and several larger pedigrees. We then again employed the TDT using the transmit program with a sliding window strategy to determine if observed transmission of any individual SNP or multiple (2, 3, 4 and 5) SNP combinations deviate from the expected value in the combined US and South African sample comprising 410 families. Results of this analysis are presented in Table 5. Significant transmission disequilibrium was observed in this sample for the single SNP, CC21 (P=0.025) and the SNP pair, CC21,33 (P=0.013). Highly significant transmission disequilibrium was observed in this sample for 2 SNP (CC33, S3, P=0.0004) 3 SNP (CC20,21,33, P=0.0008; CC21,33, S3, P=0.0003) 4 SNP (CC1a, 20,21,33, P=0.005; CC20,21,33, S3, P=0.0001) and 5 SNP (CC1a, 20,21,33, S3, P=0.0027) combinations (Table 5).

Examination of the transmissions of the individual haplotypes indicates that a particular 3 SNP haplotype comprised of CC21, CC33, and CCS3 drives the observed transmission disequilibrium (for example see Table 6). Specifically the haplotype (CC21:allele 1=G, CC33:allele 2=C, CCS3:allele 1=A [CC21,33, S3=1,2,1=G,C,A]) is transmitted with greater than expected frequency with a high degree of statistical significance. These results strongly suggest that variation in the PPP3CC gene is associated with schizophrenia susceptibility and define the CC21,33, S3:G,C,A haplotype as a risk haplotype for schizophrenia. It is of note that we identified a coding sequence mutation (CC-5 Arg->Gln) in this gene in one of the patients (Table 2). Since we have found that this gene is associated with disease susceptibility, we suggest that this SNP represents a relatively rare functional mutation that contributes to disease susceptibility in some patients/families.

Our transmission analysis indicates association of PPP3CC with schizophrenia in the relatively heterogeneous United States population sample in addition to an independent and more demographically restricted sample of affected families from South Africa, suggesting a potential generality in the association of this gene with disease.

Figure 6:
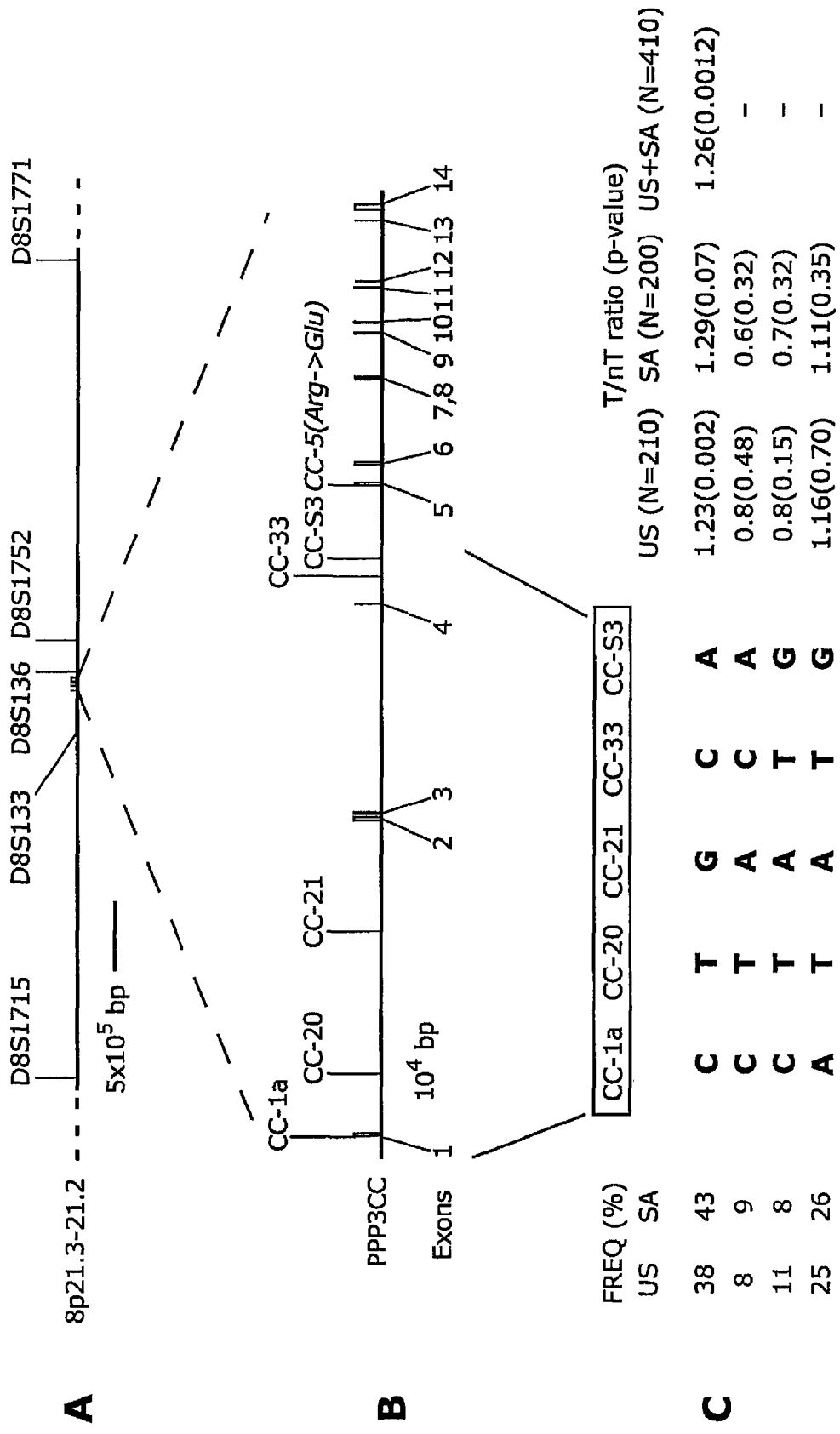
FIG. 6 is a schematic drawing of the PPP3CC gene locus.
Figure 6A:
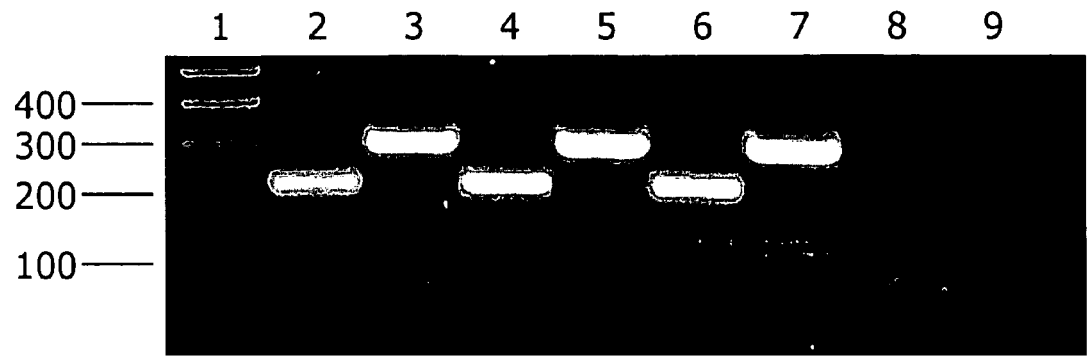
FIG. 6A shows he location of the PPP3CC gene in the 8p21.3 region is depicted in relation to relevant markers from linkage studies.
Figure 6B:
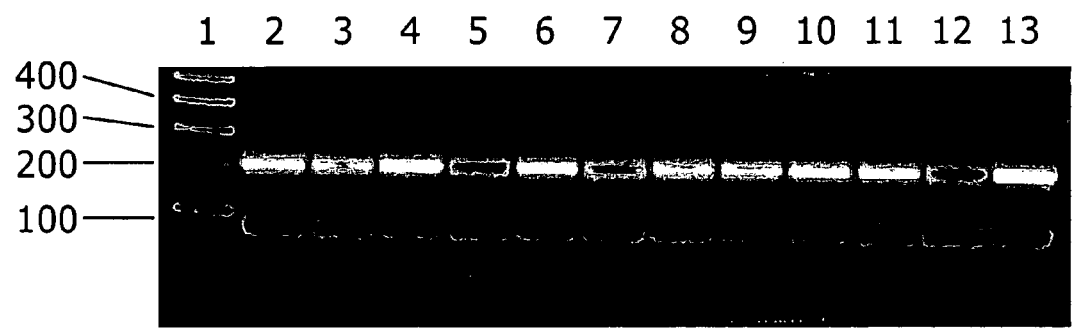
FIG. 6B shows an expanded view of the PPP3CC gene including the exon/intron structure and the locations of the SNPs used for association studies and the coding sequence mutation identified in exon 5. D8S136: Pulver et al., 1995, Brzustowicz et al., 1999; D8S1771: Blouin et al., 1998, Gurling et al., 2001; D8S1752: Blouin et al., 1998; D8S1715, D8S133: Kendler et al., 1996.

The PPP3CC gene is located within chromosome 8p21.3, a region that has been identified as a schizophrenia susceptibility locus by linkage studies in several independent samples derived from different populations. FIG. 6 is a schematic diagram of the PPP3CC locus. The location of the PPP3CC gene in the 8p21.3 region is depicted in relation to relevant markers from linkage studies in FIG. 6A. FIG. 6B presents an expanded view of the PPP3CC gene including the exon/intron structure and the locations of the SNPs used for association studies and the coding sequence mutation identified in exon 5. D8S136: Pulver et al., 1995, Brzustowicz et al., 1999; D8S1771: Blouin et al., 1998, Gurling et al., 2001; D8S1752: Blouin et al., 1998; D8S1715, D8S133: Kendler et al., 1996. Distances and positions in this figure are according to the November 2002, human draft sequence. FIG. 6C shows haplotype distribution and transmission at the PPP3CC locus. Only four haplotypes with frequencies ≧5% were observed in both US and SA samples and are shown here. The most common PPP3CC haplotype is consistently over-transmitted in both samples. T/nT: Transmitted/non-Transmitted.

Our finding of an association between PPP3CC and schizophrenia susceptibility provides strong evidence supporting the involvement of alterations in calcineurin signaling in schizophrenia pathogenesis. These results will be extended as described above to examine the genetic association of the additional genes listed in Table 1 with schizophrenia, and to expand the analysis of the genes already analyzed to include additional population samples. By extending the systematic approach described above, the association of additional loci involved in calcineurin signaling with schizophrenia susceptibility will be determined.

TABLE 3

Polymorphisms used for transmission studies

| Gene | Polymorphism name | Polymorphism type | Our ID (table 1) | NCBI I.D. | Celera I.D. | Genotype method | Genotyping PCR amplification Primers |
|---|---|---|---|---|---|---|---|
| PPP3R1 | R1P1 | 29 bp insertion | R1-1 | not listed | not listed | PCR-FLP | R1P1aF, R1P1R |
| PPP3R1 | R1S1 | SNP C/T | R1-4 | not listed | not listed | PCR-RFLP | R1S1F, R1S1cR |
| PPP3R1 | R1-24 | SNP A/G | — | rs1065248 | hCV8833092 | PCR-RFLP | R1-24F, R1-24R |
| PPP3R1 | R1-28 | SNIP A/G | — | — | hCV1282182 | PCR-RFLP | R1-28F, R1-28R |
| PPP3R1 | R1-S3 | SNIP T/C | R1-18 | rs3730335 | — | PCR-RFLP | R1S3bF, R1S3R |
| PPP3CA | CAS6 | SNP C/G | — | rs2850338 | — | PCR-RFLP | CAS6-F, CAS6-R |
| PPP3CA | CASEP1 | SNP A/C | CA-8 | rs1876267 | — | FP | CA-25F, CA-25R |
| PPP3CA | CASFP2 | SNP G/A | CA-11 | rs2851060 | — | FP | CASFP2-F, CASFP2-R |
| PPP3CA | CA-31 | SNP A/G | — | rs1880942 | — | PCR-RFLP | CA-31F, CA-31R |
| PPP3CC | CC-1a | SNP C/A | CC-3 | rs1049437 | — | PCR-RFLP | CC-1aF, CC-1aR |
| PPP3CC | CC-20 | SNP T/C | — | — | hCV1341797 | PCR-RFLP | CC-20F, CC-20R |
| PPP3CC | CC-21 | SNP G/A | — | — | hCV1341817 | PCR-RFLP | CC-21F, CC-21R |
| PPP3CC | CC-33 | SNP C/T | — | — | hCV3004214 | PCR-RFLP | CC-33F, CC-33R |
| PPP3CC | CC-S3 | SNP A/G | — | rs2461491 | — | PCR-RFLP | CCS3-F, CCS3-R |

TABLE 4

TDT analysis, P values program transmit

| | | US SCZ trios 1,2 (210 families) | | | | |
|---|---|---|---|---|---|---|
| (program Transmit) | | SNP | 2SNPs | 3SNPs | 4SNPs | 5SNPs |
| PPP3RI gene | RIPI | 0.38097 | | | | |
| | | | 0.809974 | | | |
| | RIS1 | 0.648537 | | 0.490052 | | |
| | | | 0.604115 | | 0.362[a] | |
| | P124 | 0.20632 | | 0.704672 | | 0.428[a] |
| | | | 0.603363 | | 0.60 | |
| | P128 | 0.29696 | | 0.540755 | | |
| | | | 0.47079 | | | |
| | RIS3 | 0.97607 | | | | |
| PPP3CA gene | CAS6 | 0.55571 | | | | |
| | | | 0.710112 | | | |
| | casFP1 | 0.470 | | 0.061[c] | | |
| | | | 0.296471 | | 0.289[a] | |
| | casFP2 | 0.22061 | | 0.483986 | | |
| | | | 0.216276 | | | |
| | CA31 | 0.7452 | | | | |
| PPP3CC gene | CC1a | 0.777 | | | | |
| | | | 0.752 | | | |
| | CC20 | 0.380047 | | 0.243[a] | | |
| | | | 0.169[a] | | 0.0032[a] | |
| | CC21 | 0.038 | | 0.031[a] | | 0.016[a] |
| | | | 0.013[a] | | 0.0047[a] | |
| | CC33 | 0.099 | | 0.024[b] | | |
| | | | 0.003[b] | | | |
| | CCS3 | 0.041 | | | | |

[a] one single haplotype is significant at 1 df.
[b] two single haplotypes are significant at 1 df.
[c] three single haplotypes are significant at 1 df.
US SCZ trios 1,2 refers to the United States schizophrenia triads sample
P values represent global significance calculated from the global chi s from the transmit program TDT analysis

TABLE 5

TDT analysis, Pvalues, program transmit

SA trios 1,2 + SA KRO + SA KRN + US SCZ trios 1,2
(410 families total)

| | | 1 SNP | 2 SNPs | 3 SNPs | 4 SNPs | 5 SNPs |
|---|---|---|---|---|---|---|
| PPP3CC gene | CC1a | 0.654 | | | | |
| | | | 0.587 | | | |
| | CC20 | 0.306 | | 0.169 | | |
| | | | 0.054 | | 0.005$^c$ | |
| | CC21 | 0.025 | | 0.0008$^b$ | | 0.00126$^c$ |
| | | | 0.0013$^b$ | | 0..0001$^c$ | |
| | CC33 | 0.055 | | 0.0003$^b$ | | |
| | | | 0.0004$^c$ | | | |
| | CCS3 | 0.060 | | | | |

$^a$one single haplotype is significant at 1 df.
$^b$two single haplotypes are significant at 1 df.
$^c$three single haplotypes are significant at 1 df.
SA trios 1,2 refer to the South african schizophrenia triads sample
US SCZ trios 1,2 refers to the United States schiuzophrenia triads sample
SA KRO and SA KRN refer to South african schizophrenia linkage families
SA- = South african, US = United States
P values represent global significance calculated from the global chi square values from the transmit program TDT analysis

TABLE 6

Output from Transmit program 5 SNP analysis
Transmit-2.5.2
DNA: Satrios 1,2 + US SCZ 1,2 + KRO + KRN
Def of SCZ: Narrow
LOCI: CC1a/CC20/CC21/CC33/CCS3

Estimated haplotype probabilities

| 1.2.1.1.1 | 0.0347786 | 1.2.1.1.2 | 0.00485359 |
|---|---|---|---|
| 1.1.2.1.1 | 0.00181773 | 1.1.2.1.2 | 0.0384754 |
| 1.2.2.1.1 | 0.00724337 | 2.1.2.1.2 | 0.00565494 |
| 2.2.2.1.1 | 0.000654133 | 1.2.2.1.2 | 0.0982981 |
| 1.1.1.2.1 | 0.00408184 | 2.2.2.1.2 | 0.265039 |
| 1.2.1.2.1 | 0.411919 | 1.2.1.2.2 | 0.00406284 |
| 2.1.2.1 | 0.00902496 | 1.1.2.2.2 | 0.00124278 |
| 1.1.2.2.1 | 0.0104217 | 2.1.2.2.2 | 0.00183482 |
| 1.2.2.2.1 | 0.0883283 | 2.2.2.2.2 | 0.00540427 |
| 2.2.2.2.1 | 0.0068655 | | |

Phase 4: Haplotype-based score tests
Number of families with transmissions to affected offspring: 415
1 df tests for individual haplotypes

| Haplotype | Observed | Expected | Var (O-E) | Chisq (1 df) |
|---|---|---|---|---|
| 1.2.1.1.1 | 22.233 | 29.932 | 13.334 | 4.4459 |
| 1.1.1.1.1 | 1.5581 | 1.6029 | 0.52093 | 0.003852 |
| 1.2.2.1.1 | 6.9573 | 6.4368 | 2.6978 | 0.10044 |
| 2.2.2.1.1 | 1.0178 | 0.58086 | 0.23759 | 0.80361 |
| 1.1.1.2.1 | 1.6607 | 4.2217 | 1.881 | 3.4868 |
| 1.2.1.2.1 | 388.95 | 356.65 | 99.625 | 10.471 |
| 2.2.1.2.1 | 10.274 | 7.5368 | 3.4261 | 2.186 |
| 1.1.2.2.1 | 9.7839 | 9.3957 | 3.3282 | 0.045288 |
| 1.2.2.2.1 | 72.014 | 77.115 | 33.096 | 0.7859 |
| 2.2.2.2.1 | 2.2091 | 6.6459 | 3.0028 | 6.5555 |
| 1.2.1.1.2 | 2.6265 | 4.2841 | 1.8665 | 1.472 |
| 1.1.2.1.2 | 29.711 | 33.616 | 14.824 | 1.0288 |
| 2.1.2.1.2 | 3.1441 | 5.5562 | 2.5466 | 2.2847 |
| 1.2.2.1.2 | 75.495 | 84.428 | 34.878 | 2.288 |
| 2.2.2.1.2 | 232.56 | 228.86 | 81.017 | 0.16937 |
| 1.2.1.2.2 | 1.5271 | 3.6122 | 1.5745 | 2.7615 |
| 1.1.2.2.2 | 2.0577 | 1.1055 | 0.45385 | 1.9978 |
| 1.2.2.2.2 | 1.044 | 1.6331 | 0.73685 | 0.47093 |
| 2.2.2.2.2 | 3.1725 | 4.7862 | 2.1693 | 1.2005 |

Global chisquared test, on 18 degrees of freedom = 38.271
Common haplotypes (those with frequencies >= 3%): 1.2.1.1.1, 1.2.1.2.1, 1.2.2.2.1, 1.1.2.1.2, 1.2.2.1.2, 2.2.2.1.2
Chisquared test on 6 degrees of freedom = 20.039

REFERENCE LIST 2

References for Examples 3 and 4 and Table 1

1. Liu H, Heath S C, Sobin C, Roos J L, Galke B L, Blundell M L, Lenane M, Robertson B, Wijsman E M, Rapoport J L, Gogos J A, Karayiorgou M. (2002) Proc Natl Acad Sci USA. March 19; 99(6):3717-22.
2. Liu H, Abecasis G R, Heath S C, Knowles A, Demars S, Chen Y J, Roos J L, Rapoport J L, Gogos J A, Karayiorgou M. (2002) Proc Natl Acad Sci USA. Dec. 24, 1999; (26): 16859-64.
3. Clayton, D., Am J Hum Genet. October 1999; 65(4):1170-7.
4. Camp, N. J., Neuhausen, S. L., Tiobech, J., Polloi, A., Coon, H. and Myles-Worsley, M., Genomewide multipoint linkage analysis of seven extended Palauan pedigrees with schizophrenia, by a Markov-chain Monte Carlo method, *Am J Hum Genet*, 69 (2001) 1278-89.
5. Coon, H., Myles-Worsley, M., Tiobech, J., Hoff, M., Rosenthal, J., Bennett, P., Reimherr, F., Wender, P., Dale, P., Polloi, A. and Byerley, W., Evidence for a chromosome 2p13-14 schizophrenia susceptibility locus in families from Palau, Micronesia, *Mol Psychiatry*, 3 (1998) 521-7.
6. Gurling, H. M., Kalsi, G., Brynjolfson, J., Sigmundsson, T., Sherrington, R., Mankoo, B. S., Read, T., Murphy, P., Blayeri, E., McQuillin, A., Petursson, H. and Curtis, D., Genomewide genetic linkage analysis confirms the presence of susceptibility loci for schizophrenia, on chromosomes 1q32.2, 5q33.2, and 8p21-22 and provides support for linkage to schizophrenia, on chromosomes 11q23.3-24 and 20q12.1-11.23, *Am J Hum Genet*, 68 (2001) 661-73.
7. Kennedy, J. L., Basile, V. S. and Macciardi, F. M., Chromosome 4 Workshop Summary: Sixth World Congress on Psychiatric Genetics, Bonn, Germany, Oct. 6-10, 1998, *Am J Med Genet*, 88 (1999) 224-8.
8. Levinson, D. F., Mahtani, M. M., Nancarrow, D. J., Brown, D. M., Kruglyak, L., Kirby, A., Hayward, N. K., Crowe, R. R., Andreasen, N. C., Black, D. W., Silverman, J. M., Endicott, J., Sharpe, L., Mohs, R. C., Siever, L. J., Walters, M. K., Lennon, D. P., Jones, H. L., Nertney, D. A., Daly, M. J., Gladis, M. and Mowry, B. J., Genome scan of schizophrenia, *Am J Psychiatry*, 155 (1998) 741-50.
9. Blouin, J. L., Dombroski, B. A., Nath, S. K., Lasseter, V. K., Wolyniec, P. S., Nestadt, G., Thornquist, M., Ullrich, G., McGrath, J., Kasch, L., Lamacz, M., Thomas, M. G., Gehrig, C., Radhakrishna, U., Snyder, S. E., Balk, K. G., Neufeld, K., Swartz, K. L., DeMarchi, N., Papadimitriou, G. N., Dikeos, D. G., Stefanis, C. N., Chakravarti, A., Childs, B., Pulver, A. E. and et al., Schizophrenia susceptibility loci on chromosomes 13q32 and 8p21, *Nat Genet*, 20 (1998) 70-3.
10. Kendler, K. S., MacLean, C. J., O'Neill, F. A., Burke, J., Murphy, B., Duke, F., Shinkwin, R., Easter, S. M., Webb, B. T., Zhang, J., Walsh, D. and Straub, R. E., Evidence for a schizophrenia vulnerability locus on chromosome 8p in the Irish Study of High-Density Schizophrenia Families, *Am J Psychiatry*, 153 (1996) 1534-40.
11. Pulver, A. E., Lasseter, V. K., Kasch, L., Wolyniec, P., Nestadt, G., Blouin, J. L., Kimberland, M., Babb, R., Vourlis, S., Chen, H. and et al., Schizophrenia: a genome scan targets chromosomes 3p and 8p as potential sites of susceptibility genes, *Am J Med Genet*, 60 (1995) 252-60.
12. Bailer, U., Leisch, F., Meszaros, K., Lenzinger, E., Willinger, U., Strobl, R., Gebhardt, C., Gerhard, E., Fuchs, K., Sieghart, W., Kasper, S., Hornik, K. and Aschauer, H. N., Genome scan for susceptibility loci for schizophrenia, *Neuropsychobiology*, 42 (2000) 175-82

13. Karayiorgou, M. and Gogos, J. A., A turning point in schizophrenia genetics, *Neuron*, 19 (1997) 967-79.
14. Thaker, G. K. and Carpenter, W. T., Jr., Advances in schizophrenia, *Nat Med*, 7 (2001) 667-71.
15. Stober, G., Saar, K., Ruschendorf, F., Meyer, J., Nurnberg, G., Jatzke, S., Franzek, E., Reis, A., Lesch, K. P., Wienker, T. F. and Beckmann, H., Splitting schizophrenia: periodic catatonia-susceptibility locus on chromosome 15q15, *Am J Hum Genet*, 67 (2000) 1201-7.
16. Paunio, T., Ekelund, J., Varilo, T., Parker, A., Hovatta, I., Turunen, J. A., Rinard, K., Foti, A., Terwilliger, J. D., Juvonen, H., Suvisaari, J., Arajarvi, R., Suokas, J., Partonen, T., Lonnqvist, J., Meyer, J. and Peltonen, L., Genome-wide scan in a nationwide study sample of schizophrenia families in Finland reveals susceptibility loci on chromosomes 2q and 5q, *Hum Mol Genet*, 10 (2001) 3037-48.
17. Faraone, S. V., Matise, T., Svrakic, D., Pepple, J., Malaspina, D., Suarez, B., Hampe, C., Zambuto, C. T., Schmitt, K., Meyer, J., Markel, P., Lee, H., Harkavy Friedman, J., Kaufmann, C., Cloninger, C. R. and Tsuang, M. T., Genome scan of European-American schizophrenia pedigrees: results of the NIMH Genetics Initiative and Millennium Consortium, *Am J Med Genet*, 81 (1998) 290-5.
18. Craddock, N. and Lendon, C., Chromosome Workshop: chromosomes 11, 14, and 15, *Am J Med Genet*, 88 (1999) 244-54.
19. Chowdari, K. V., Xu, K., Zhang, F., Ma, C., Li, T., Xie, B. Y., Wood, J., Trucco, M., Tsoi, W. F., Saha, N., Rudert, W. A. and Nimgaonkar, V. L., Immune related genetic polymorphisms and schizophrenia among the Chinese, *Hum Immunol*, 62 (2001) 714-24.
20. Wright, P., Donaldson, P. T., Underhill, J. A., Choudhuri, K., Doherty, D. G. and Murray, R. M., Genetic association of the HLA DRB1 gene locus on chromosome 6p21.3 with schizophrenia, *Am J Psychiatry*, 153 (1996) 1530-3.
21. Brzustowicz, L. M., Hodgkinson, K. A., Chow, E. W., Honer, W. G. and Bassett, A. S., Location of a major susceptibility locus for familial schizophrenia on chromosome 1q21-q22, *Science*, 288 (2000) 678-82.
22. Freedman, R., Leonard, S., Olincy, A., Kaufmann, C. A., Malaspina, D., Cloninger, C. R., Svrakic, D., Faraone, S. V. and Tsuang, M. T., Evidence for the multigenic inheritance of schizophrenia, *Am J Med Genet*, 105 (2001) 794-800.
23. Schwab, S. G., Eckstein, G. N., Hallmayer, J., Lerer, B., Albus, M., Borrmann, M., Lichtermann, D., Ertl, M. A., Maier, W., and Wildenauer, D. B., *Mol. Psychiatry*. March (1997); 2(2):156-60.
24. Crowe, R. R. and Vieland, V., *Am J Med Genet* Jun. 18, (1999); 88(3):229-32.
25. Straub, R. E., MacLean, C. J., Ma, Y., Webb, B. T., Myakishev, M. V., Harris-Kerr, C., Wormley, B., Sadek, H., Kadambi, B., O'Neill, F. A., Walsh, D. and Kendler, K. S. Mol Psychiatry. 2002; 7(6):542-59.
26. Baumgrass, R., et al., *Reversible inhibition of calcineurin by the polyphenolic aldehyde gossypol*. J Biol Chem, 2001. 276(51): p. 47914-21.
27. Boss, V., D. J. Talpade, and T. J. Murphy, *Induction of NFAT-mediated transcription by Gq-coupled receptors in lymphoid and non-lymphoid cells*. J Biol Chem, 1996. 271(18): p. 10429-32.
28. Sambasivarao, D., et al., A novel immunosuppressive factor in bovine colostrum blocks activation of the interleukin 2 gene enhancer at the NFAT site. Biochem Cell Biol, 1996. 74(4): p. 585-93.
29. Snyder, G. L., et al., *Phosphorylation of DARPP-32 and protein phosphatase inhibitor-1 in rat choroid plexus: regulation by factors other than dopamine*. J Neurosci, 1992. 12(8): p. 3071-83.
30. Czernik, A. J., et al., *Production of phosphorylation state-specific antibodies*. Methods Enzymol, 1991. 201: p. 264-83.
31. Mondragon, A., Griffith, E. C., Sun, L., Xiong, F., Armstrong, C. and Liu, J. O. *Biochemistry* Apr. 22, 1997; 36(16):4934-42
32. Boute N, Jockers R, Issad T. *Trends Pharmacol Sci.* August 2002; 23(8):351-4.
33. Chumakov I, Blumenfeld M, Guerassimenko O, Cavarec L, Palicio M, Abderrahim H, Bougueleret L, Barry C, Tanaka H, La Rosa P, Puech A, Tahri N, Cohen-Akenine A, Delabrosse S, Lissarrague S, Picard F P, Maurice K, Essioux L, Millasseau P, Grel P, Debailleul V, Simon A M, Caterina D, Dufaure I, Malekzadeh K, Belova M, Luan J J, Bouillot M, Sambucy J L, Primas G, Saumier M, Boubkiri N, Martin-Saumier S, Nasroune M, Peixoto H, Delaye A, Pinchot V, Bastucci M, Guillou S, Chevillon M, Sainz-Fuertes R, Meguenni S, Aurich-Costa J, Cherif D, Gimalac A, Van Duijn C, Gauvreau D, Ouellette G, Fortier I, Raelson J, Sherbatich T, Riazanskaia N, Rogaev E, Raeymaekers P, Aerssens J, Konings F, Luyten W, Macciardi F, Sham P C, Straub R E, Weinberger D R, Cohen N, Cohen D, Ouelette G, Realson J., *Proc Natl Acad Sci USA*. Oct. 15, 2002; 99(21):13675-80.
34. Lewontin R C (1988) On measures of gametic disequilibrium. Genetics 120:849-852

Example 5

Expression of PPP3CC in Human Brain Regions

Materials and Methods

PCR on cDNA. Adult total human brain, fetal total human brain, and human testis cDNA consisted of marathon-ready cDNAs purchased from Clontech (Palo Alto, Calif.). The adult human brain region panel was purchased from Origene (Rockville, Md.).

Primer pair one consists of a forward primer from PPP3CC exon 1, 5'-GCGCTTCCACCTCTCCACC-3' (SEQ ID NO: 3) and a reverse primer from PPP3CC exon 2, 5'-CTATCATAGTCTTCTCTTGCCTC-3' (SEQ ID NO: 4). Primer pair 2 consists of a forward primer, 5'-CCCATTCATGACTTAGAGTCC-3' (SEQ ID NO: 5) and a reverse primer, CCCCTTTATAGCACAAGACTTC-3' (SEQ ID NO: 6) from PPP3CC exon 14 (3' UTR). These primers were designed to differ from PPP3CA and PPP3CB sequence, particularly at the 3' end, in order to be PPP3CC specific. Primer pair 1 amplifies a 218 bp fragment extending from exon 1 to exon 2. Primer pair 2 amplifies a 298 bp fragment from exon 14 consisting of 3'UTR sequence.

Fragments were amplified in a 25 ul reaction mixture containing approximately 0.25 ng cDNA (Clontech) or 1.0 ng cDNA (Origene), each primer at 400 nM concentration, each dNTP at 200 uM concentration and 1.5 U Taq polymerase (Sigma Chemical Co., St. Louis, Mo.) in OptiPrime (Stratagene, La Jolla, Calif.) buffer 6 conditions. Reactions were performed by touchdown PCR amplification as follows: an initial denaturation step at 94° C. for 2 min, followed by 20 amplification cycles: 30 sec at 94° C.; 45 sec at 68° initially, 45 sec at 72° (−1 degree each cycle) followed by 15 amplification cycles: 30 sec at 94° C.; 45 sec at 53°, 45 sec at 72°, followed by a final extension step of 72° C. for 7 min.

The entire PCR amplification products were run on a 2% agarose gel and visualized by ethidium bromide staining.

Results

Figure 7:
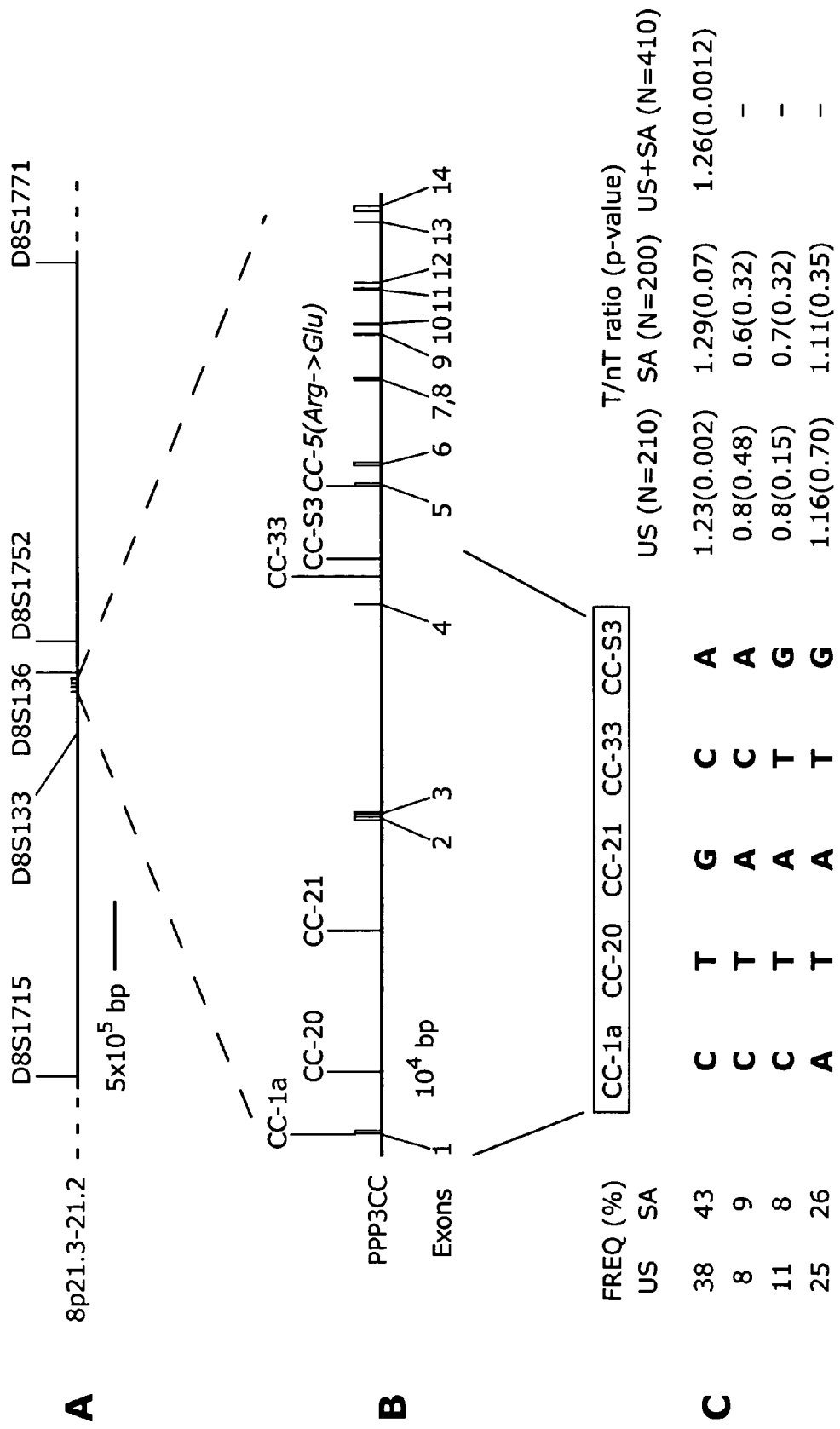
FIG. 7A is a photo of an agarose gel showing products of PCR amplification of cDNA from human adult total brain, fetal total brain and testis and demonstrating PPP3CC expression in human brain.
FIG. 7B is a photo of an agarose gel showing products of PCR amplification of cDNA from human adult brain regions
Figure 7A:
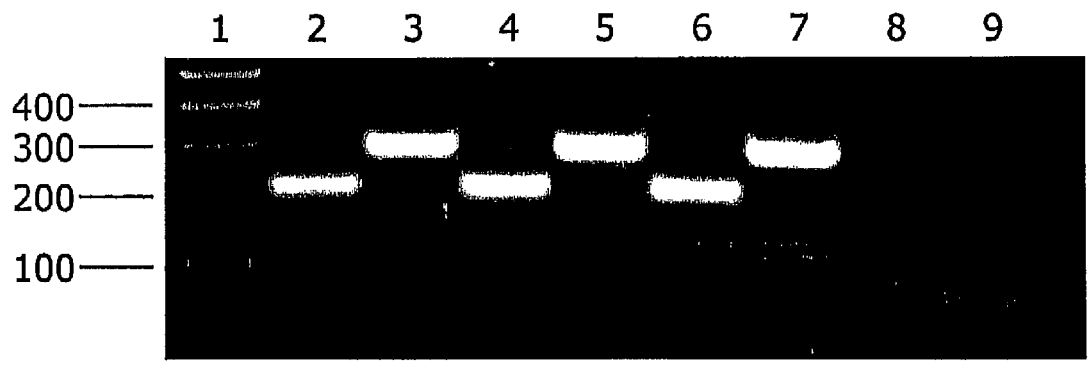

PPP3CC has been designated a testis-specific calcineurin catalytic subunit gene based primarily on its initial characterization in the mouse. To determine whether PPP3CC is expressed in the human brain, we first performed PCR amplification of cDNA from human total adult brain and from total fetal brain with PPP3CC-specific primers. As shown in FIG. 7A, PCR reactions with two different primer pairs indicate that PPP3CC is expressed in the human adult and fetal brain.

Figure 7B:
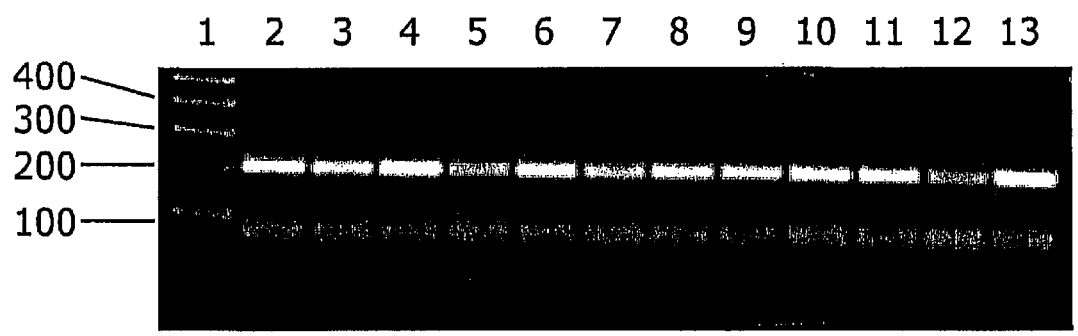

To further analyze the expression of PPP3CC in the human brain, we performed PCR amplification of a panel of CNS region-specific cDNAs with one of the PPP3CC-specific primer pairs. As shown in FIG. 7B, PPP3CC expression is detected in multiple regions of adult human brain including, frontal and temporal lobes, hippocampus, amygdala, thalamus, striatum, substantia nigra, hypothalamus, cerebellum, pons and medulla. PPP3CC expression is also detected in spinal cord Lane order of FIG. 7A: 1—100 bp marker; 2—adult brain, primers 1; 3—adult brain, primers 2; 4—fetal brain primers 1; 5—fetal brain primers 2, 6—testis, primers 1; 7—testis, primers 2; 8—no DNA control, primers 1; 9—no DNA control, primers 2. The products less than 100 bp in size are present in the no DNA control and are most likely primer-related amplification artifacts.

Lane order of FIG. 7B: 1—100 bp marker, 2—frontal lobe, 3—temporal lobe, 4—cerebellum, 5—hippocampus, 6—substantia nigra, 7—caudate nucleus, 8—amygdala, 9—thalamus, 10—hypothalamus, 11—pons, 12—medulla, 13—spinal cord.

TABLE 7

Abbreviations and references for protein and gene names and gene accession numbers discussed herein CNB—calcineurin B regulatory subunit, PPP3R1, acc# NM_000945
CNAα—calcineurin A catalytic subunit α, PPP3CA, acc# NM_000944
CNAβ—calcineurin A catalytic subunit β, PPP3CB, acc# NM_021132
CNAγ—calcineurin A catalytic subunit γ, PPP3CC, acc# NM_005605
Calcineurin B homologous protein, calcium binding protein P22, CHP acc# NM_007236 [31]
Down's syndrome critical region protein 1 -(member of calcipressins), DSCR1, acc# NM_004414
Cabin—calcineurin binding protein 1, KIAA0330, acc# NM_012295, [32, 33]
Calcineurin binding protein calsarcin-1, CS-1, MYOZ2, acc# NM_016599 [34]
calcineurin binding protein, calsarcin-3, CS-3, acc# NM_133371 [34]
A kinase anchor protein 5, AKAP5 (also AKAP79), acc# NM_004857, [35-37]
FK506 binding protein 5, FKBP-5 (also FKBP-51), acc# NM_004117 [38-40]
IP3 receptor type 1, ITPR1, acc# NM_002222, [41, 42]
ryanodine receptor type 3, RYR3, acc# NM_001036 [41, 42]
adenylate cyclase activating polypeptide, PACAP, ADCYAP1, acc# NM_001117 [1, 3]
calcium-signal modulating cyclophilin ligand, calcium modulating ligand, CAMLG, acc# NM_001745 [2]
Interleukin enhancer binding factor 2, 45 kD, NF45 subunit of nuclear factor of activated t cells, ILF2, acc# NM_004515 [43, 44]
Nuclear factor of activated T cells, cytoplasmic, calcineurin dependent 2, NFATC2, acc# NM_012340, [45-47]
Mouse PPP3R1 NM_024459
Mouse PPP3CC NM_008915

GENERAL REFERENCE LIST

1. Lee, H. W., et al., *Pituitary adenylate cyclase-activating polypeptide regulation of vasoactive intestinal polypeptide transcription requires Ca2+ influx and activation of the serine/threonine phosphatase calcineurin.* J Neurochem, 1999. 73(4): p. 1769-72.
2. Bram, R. J. and G. R. Crabtree, *Calcium signalling in T cells stimulated by a cyclophilin B-binding protein.* Nature, 1994. 371(6495): p. 355-8.
3. Hashimoto, H., et al., *Altered psychomotor behaviors in mice lacking pituitary adenylate cyclase-activating polypeptide (PACAP).* Proc Natl Acad Sci USA, 2001. 98(23): p. 13355-60.
4. Otto, C., et al., *Altered emotional behavior in PACAP-type-I-receptor-deficient mice.* Brain Res Mol Brain Res, 2001. 92(1-2): p. 78-84.
5. Hodgkiss, J. P. and J. S. Kelly, *Only 'de novo' long-term depression (LTD) in the rat hippocampus in vitro is blocked by the same low concentration of FK506 that blocks LTD in the visual cortex.* Brain Res, 1995. 705(1-2): p. 241-46.
6. Ikegami, S., et al., *A facilitatory effect on the induction of long-term potentiation in vivo by chronic administration of antisense oligodeoxynucleotides against catalytic subunits of calcineurin.* Brain Res Mol Brain Res, 1996. 41(1-2): p. 183-91.
7. Isaac, J., *Protein Phosphatase 1 and LTD. Synapses Are the Architects of Depression.* Neuron, 2001. 32(6): p. 963-6.
8. Kato, K., [*The role of calcineurin on the induction of synaptic plasticity*]. Nihon Shinkei Seishin Yakurigaku Zasshi, 2000. 20(5): p. 189-98.
9. Mulkey, R. M., et al., *Involvement of a calcineurin/inhibitor-1 phosphatase cascade in hippocampal long-term depression.* Nature, 1994. 369(6480): p. 486-8.
10. Torii, N., et al., *An inhibitor for calcineurin, FK506, blocks induction of long-term depression in rat visual cortex.* Neurosci Lett, 1995. 185(1): p. 1-4.
11. Zeng, H., et al., *Forebrain-specific calcineurin knockout selectively impairs bidirectional synaptic plasticity and working/episodic-like memory.* Cell, 2001. 107(5): p. 617-29.
12. Zhuo, M., et al., *A selective role of calcineurin aalpha in synaptic depotentiation in hippocampus.* Proc Natl Acad Sci USA, 1999. 96(8): p. 4650-5.
13. Amital, H. and Y. Shoenfeld, *Autoimmunity and schizophrenia: an epiphenomenon or an etiology?* Isr J Med Sci, 1993. 29(9): p. 593-7.
14. Ganguli, R., et al., *Autoimmunity in schizophrenia: a review of recent findings.* Ann Med, 1993. 25(5): p. 489-96.
15. Ganguli, R., J. S. Brar, and B. S. Rabin, *Immune abnormalities in schizophrenia: evidence for the autoimmune hypothesis.* Harv Rev Psychiatry, 1994. 2(2): p. 70-83.
16. Kirch, D. G., *Infection and autoimmunity as etiologic factors in schizophrenia: a review and reappraisal.* Schizophr Bull, 1993. 19(2): p. 355-70.
17. Noy, S., A. Achiron, and N. Laor, *Schizophrenia and autoimmunity—a possible etiological mechanism?* Neuropsychobiology, 1994. 30(4): p. 157-9.
18. Rothermundt, M., V. Arolt, and T. A. Bayer, *Review of immunological and immunopathological findings in schizophrenia.* Brain Behav Immun, 2001. 15(4): p. 319-39.
19. Rubinstein, G., *Schizophrenia, rheumatoid arthritis and natural resistance genes.* Schizophr Res, 1997. 25(3): p. 177-81.
20. Sakic, B., H. Szechtman, and J. A. Denburg, *Neurobehavioral alterations in autoimmune mice.* Neurosci Biobehav Rev, 1997. 21(3): p. 327-40.
21. Schwartz, M. and H. Silver, *Lymphocytes, autoantibodies and psychosis—coincidence versus etiological factor: an update.* Isr J Psychiatry Relat Sci, 2000. 37(1): p. 32-6.

22. Baumgrass, R., et al., *Reversible inhibition of calcineurin by the polyphenolic aldehyde gossypol.* J Biol Chem, 2001. 276(51): p. 47914-21.
23. Boss, V., D. J. Talpade, and T. J. Murphy, *Induction of NFA T-mediated transcription by Gq-coupled receptors in lymphoid and non-lymphoid cells.* J Biol Chem, 1996. 271 (18): p. 10429-32.
24. Sambasivarao, D., et al., *A novel immunosuppressive factor in bovine colostrum blocks activation of the interleukin 2 gene enhancer at the NFAT site.* Biochem Cell Biol, 1996. 74(4): p. 585-93.
25. Mohn, A. R., et al., *Mice with reduced NMDA receptor expression display behaviors related to schizophrenia.* Cell, 1999. 98(4): p. 427-36.
26. Snyder, G. L., et al., *Phosphorylation of DARPP-32 and protein phosphatase inhibitor-1 in rat choroid plexus: regulation by factors other than dopamine.* J Neurosci, 1992. 12(8): p. 3071-83.
27. Czemik, A. J., et al., *Production of phosphorylation state-specific antibodies.* Methods Enzymol, 1991. 201: p. 264-83.
28. Klinger, M., et al., *Suramin and the suramin analogue NF307 discriminate among calmodulin-binding sites.* Biochem J, 2001. 355(Pt 3): p. 827-33.
29. Misra, U. K., G. Gawdi, and S. V. Pizzo, *Cyclosporin A inhibits inositol 1,4,5-trisphosphate binding to its receptors and release of calcium from intracellular stores in peritoneal macrophages.* J Immunol, 1998. 161(11): p. 6122-7.
30. Misra, U. K., G. Gawdi, and S. V. Pizzo, *Chloroquine, quinine and quinidine inhibit calcium release from macrophage intracellular stores by blocking inositol 1,4,5-trisphosphate binding to its receptor.* J Cell Biochem, 1997. 64(2): p. 225-32.
31. Manfroid, I., J. A. Martial, and M. Muller, *Inhibition of protein phosphatase PP1 in GH3B6, but not in GH3 cells, activates the MEK/ERK/c-fos pathway and the human prolactin promoter, involving the coactivator CPB/p300.* Mol Endocrinol, 2001. 15(4): p. 625-37.
32. Alberts, A. S., et al., *Expression of a peptide inhibitor of protein phosphatase 1 increases phosphorylation and activity of CREB in NIH 3T3 fibroblasts.* Mol Cell Biol, 1994. 14(7): p. 4398-407.
33. Lefebvre, P., et al., *Protein phosphatases 1 and 2A regulate the transcriptional and DNA binding activities of retinoic acid receptors.* J Biol Chem, 1995. 270(18): p. 10806-16.
34. Lin, X., et al., *Inhibition of calcineurin phosphatase activity by a calcineurin B homologous protein.* J Biol Chem, 1999. 274(51): p. 36125-31.
35. Sun, L., et al., *Cabin 1, a negative regulator for calcineurin signaling in T lymphocytes.* Immunity, 1998. 8(6): p. 703-11.
36. Lai, M. M., et al., *Cain, a novel physiologic protein inhibitor of calcineurin.* J Biol Chem, 1998. 273(29): p. 18325-31.
37. Frey, N., J. A. Richardson, and E. N. Olson, *Calsarcins, a novel family of sarcomeric calcineurin-binding proteins.* Proc Natl Acad Sci USA, 2000. 97(26): p. 14632-7.
38. Coghlan, V. M., et al., *Association of protein kinase A and protein phosphatase 2B with a common anchoring protein.* Science, 1995. 267(5194): p. 108-1.
39. Kashishian, A., et al., *AKAP79 inhibits calcineurin through a site distinct from the immunophilin-binding region.* J Biol Chem, 1998. 273(42): p. 27412-9.
40. Klauck, T. M., et al., *Coordination of three signaling enzymes by AKAP79, a mammalian scaffold protein.* Science, 1996. 271(5255): p. 1589-92.
41. Baughman, G., et al., *FKBP51, a novel T-cell-specific immunophilin capable of calcineurin inhibition.* Mol Cell Biol, 1995. 15(8): p. 4395-402.
42. Baughman, G., et al., *Tissue distribution and abundance of human FKBP51, and FK506-binding protein that can mediate calcineurin inhibition.* Biochem Biophys Res Commun, 1997. 232(2): p. 437-43.
43. Li, T. K., et al., *Calcium-and FK506-independent interaction between the immunophilin FKBP51 and calcineurin.* J Cell Biochem, 2002. 84(3): p. 460-71.
44. Cameron, A. M., et al., *Calcineurin associated with the inositol 1,4,5-trisphosphate receptor-FKBP12 complex modulates Ca2+ flux.* Cell, 1995. 83(3): p. 463-72.
45. Genazzani, A. A., E. Carafoli, and D. Guerini, *Calcineurin controls inositol 1,4,5-trisphosphate type 1 receptor expression in neurons.* Proc Natl Acad Sci USA, 1999. 96(10): p. 5797-801.
46. Marcoulatos, P., et al., *Mapping interleukin enhancer binding factor 2 gene (ILF2) to human chromosome 1 (1q11-qter and 1p11-p12) by polymerase chain reaction amplification of human-rodent somatic cell hybrid DNA templates.* J Interferon Cytokine Res, 1996. 16(12): p. 1035-8.
47. Kao, P. N., et al., *Cloning and expression of cyclosporin A-and FK506-sensitive nuclear factor of activated T-cells: NF45 and NF90.* J Biol Chem, 1994. 269(32): p. 20691-9.
48. Horsley, V. and G. K. Pavlath, *Nfat: ubiquitous regulator of cell differentiation and adaptation.* J Cell Biol, 2002. 156(5): p. 771-4.
49. Graef, I. A., F. Chen, and G. R. Crabtree, *NFAT signaling in vertebrate development.* Curr Opin Genet Dev, 2001. 11(5): p. 505-12.
50. Plyte, S., et al., *Identification and characterization of a novel nuclear factor of activated T-cells-1 isoform expressed in mouse brain.* J Biol Chem, 2001. 276(17): p. 14350-8.
51. Kissinger, C R, et al., *Crystal structures of human calcineurin and the human FKBP12-FK506-calcineurin complex,* Nature, 1995. 378(6557):641-4.
52. Griffith, J P, et al., *X-ray structure of calcineurin inhibited by the immunophilin-immunosuppressant FKBP12-FK506 complex,* Cell Aug. 11, 1995; 82(3):507-22.
53. Ausubel et al., *Current Protocols in Molecular Biology,* John Wiley & Sons, New York, 2000.

We claim:

1. A method for identifying a candidate compound for treatment of schizophrenia comprising steps of
performing an assay to identify a calcineurin activator; and
testing the calcineurin activator in at least one schizophrenia disease model to determine if the calcineurin activator ameliorates at least one symptom in the schizophrenia disease model.

2. The method of claim 1, further comprising the steps of modifying the calcineurin activator and testing the modified calcineurin activator to select a modified calcineurin activator that has increased solubility, absorbability or bioavailability as compared to the calcineurin activator prior to modification.

3. The method of claim 1, further comprising the steps of modifying the calcineurin activator and testing the modified calcineurin activator to select a modified calcineurin activator that has enhanced ability to cross the blood-brain barrier as compared to the calcineurin activator prior to modification.

4. The method of claim 1, wherein the step of performing an assay comprises:
providing a biological system comprising phosphorylated calcineurin substrate and calcineurin;
contacting the biological system with a compound;
comparing the extent or rate of dephosphorylation of the substrate with the extent or rate of dephosphorylation occurring in the absence of the compound; and
identifying the compound as a candidate compound that increases calcineurin activity if the extent or rate of dephosphorylation in the presence of the compound is increased compared to the extent or rate of dephosphorylation that occurs in the absence of the compound.

5. The method of claim 1, further comprising a step of testing the candidate compound in a human subject suffering from schizophrenia.

* * * * *

UNITED STATES PATENT AND TRADEMARK OFFICE
CERTIFICATE OF CORRECTION

| | | Page 1 of 1 |
|---|---|---|
| PATENT NO. | : 7,935,500 B2 | |
| APPLICATION NO. | : 10/400348 | |
| DATED | : May 3, 2011 | |
| INVENTOR(S) | : David J. Gerber | |

It is certified that error appears in the above-identified patent and that said Letters Patent is hereby corrected as shown below:

Please delete the paragraph titled 'GOVERNMENT SUPPORT' encompassing column 1, lines 18-24:

"The United States Government has provided grant support utilized in the development of the present invention. In patricular, P50-MH58880, awarded by the National Institute of Health; R01-MH61399, awarded by the National Institute of Health have supported development of this invention. The United States Government may have certain rights in the invention."

and replace with:

--This invention was made with government support under Grant No. 5-P50-MH58880-03 awarded by the National Institutes of Health. The government has certain rights in this invention.--

Signed and Sealed this
Twenty-third Day of October, 2012

David J. Kappos
*Director of the United States Patent and Trademark Office*